US009605024B2

(12) United States Patent
Kornacker et al.

(10) Patent No.: US 9,605,024 B2
(45) Date of Patent: *Mar. 28, 2017

(54) PAR4 AGONIST PEPTIDES

(71) Applicant: Bristol-Myers Squibb Company, Princeton, NJ (US)

(72) Inventors: Michael G. Kornacker, Seattle, WA (US); Claudio Mapelli, Langhorne, PA (US); Douglas J. Riexinger, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/051,067

(22) Filed: Feb. 23, 2016

(65) Prior Publication Data

US 2016/0304560 A1 Oct. 20, 2016

Related U.S. Application Data

(63) Continuation of application No. 14/554,387, filed on Nov. 26, 2014, now Pat. No. 9,303,065, which is a continuation of application No. 13/869,093, filed on Apr. 24, 2013, now Pat. No. 8,927,688.

(60) Provisional application No. 61/781,538, filed on Mar. 14, 2013, provisional application No. 61/638,577, filed on Apr. 26, 2012.

(51) Int. Cl.
| | |
|---|---|
| *A61K 38/00* | (2006.01) |
| *A61K 38/08* | (2006.01) |
| *A61K 38/10* | (2006.01) |
| *C07K 7/06* | (2006.01) |
| *C07K 14/705* | (2006.01) |
| *C07D 487/04* | (2006.01) |
| *C07D 513/04* | (2006.01) |

(52) U.S. Cl.
CPC .............. *C07K 7/06* (2013.01); *C07D 487/04* (2013.01); *C07D 513/04* (2013.01); *C07K 14/705* (2013.01); *A61K 38/00* (2013.01)

(58) Field of Classification Search
CPC ........ A61K 38/00; A61K 38/08; A61K 38/10; C07K 14/705; C07K 7/06
USPC ................................................. 530/328, 329
See application file for complete search history.

(56) References Cited

U.S. PATENT DOCUMENTS

2005/0096362 A1   5/2005   Kuo et al.

FOREIGN PATENT DOCUMENTS

| EP | 0 667 345 A1 | 8/1995 |
| EP | 1 166 785 A1 | 1/2002 |
| WO | WO 01/58930 A1 | 8/2001 |
| WO | WO 01/94411 A1 | 12/2001 |
| WO | WO 03/033515 A1 | 4/2003 |

OTHER PUBLICATIONS

Allen, L.V., Jr., ed., *Remington: The Science and Practice of Pharmacy*, 22nd Edition, Pharmaceutical Press, London, UK, 2012.
Atherton, E. et al., "The Fluorenylmethoxycarbonyl Amino Protecting Group", *The Peptides: Analysis, Synthesis, Biology*, vol. 9: "Special Methods in Peptide Synthesis, Part C", pp. 1-38, Undenfriend, S. et al., eds., Academic Press, San Diego, publ., 1987.
Barany, G. et al., *The Peptides: Analysis, Synthesis, Biology*, vol. 2: "Special Methods in Peptide Synthesis, Part A", pp. 3-284, Gross, E. et al., eds., Academic Press, NY, 1980.
Blom, J.W. et al., "Malignancies, Prothrombotic Mutations, and the Risk of Venous Thrombosis", JAMA, vol. 293(6), pp. 715-722, 2005.
Bundgaard, H., "Means to Enhance Penetration" Advanced Drug Delivery Reviews, vol. 8, pp. 1-38, 1992.
Bundgaard, H. et al., Chapter 5, "Design and Application of Prodrugs", Krosgaard-Larsen, P. et al., eds., *A Textbook of Drug Design and Development*, pp. 113-191 Harwood Academic Publishers, 1991.
Bundgaard, H. et al., "Glycolamide Esters as Biolabile Prodrugs of Carboxylic Acid Agents: Synthesis, Stability, Bioconversion, and Physicochemical Properties", J. of Pharmaceutical Sciences, vol. 77(4), p. 285, 1988.
Bundgaard, H., ed., *Design of Prodrugs*, Elsevier, 1985.
Chen, Hua-Sin et al., "Synthesis and antiplatelet activity of ethyl 4-(1-benzyl-1 H-indazol-3-yl)benzoate (YD-3) derivatives", Bioorganic & Medicinal Chemistry, vol. 16, pp. 1262-1278, 2008.
Coughlin, Shaun R., "Thrombin signaling and protease-activated receptors", Nature, vol. 407, pp. 258-264, 2000.
Faruqi, T.R., et al., "Structure-Function Analysis of Protease-activated Receptor 4 Tethered Ligand Peptides", The Journal of Biological Chemistry, vol. 275126), pp. 19728-19734, 2000.
Fritz-Langhals, E., "Alkali Metal Fluorides as Efficient Fluorinating Agents. Enantiocontrolled Synthesis of 2-Fluoroalkyl Carboxylates and 1-Fluoroalkyl Benzenes", Tetrahedron: Asymmetry, vol. 5(6), pp. 981-986, 1994.
Gennaro, Alfonso R., *Remington's Pharmaceutical Sciences*, 18th Edition, Mack Publishing Company Easton, PA, 1990.
Gennaro, Alfonso R., ed., *Remington: The Science and Practice of Pharmacy*, 20th Edition, Mack Publishing Co., Easton Pa., 2000.
Green, J. et al., "Studies on the Acylation of Hydroxy-Functionalized Resins Using Fmoc Amino Acids Activated Using Diisopropylcarbodiimide/HOBt or as Acid Fluorides" Tetrahedron, vol. 49: (20) pp. 4141-4146, 1993.
Hadfield, A. et al., "Practical, Large-Scale Synthesis of 2,2-Dimethyl-5-Hydroxy-4-0xo-Benzo-1,4-Dioxin", Synthetic Communications, vol. 24(7), pp. 1025-1028, 1994.
Kahn, Mark L et al., "A dual thrombin receptor system for platelet activation", Nature, vol. 394 (6694), pp. 690-694, 1994.
Kamisuki, S. et al., "Total synthesis of dehydroaltenusin", Tetrahedron, vol. 60, pp. 5695-5700, 2004.
Kakeya, N. et al., "Studies on Prod rugs of Cephalosporins. I. Synthesis and Biological Properties of Glycyloxybenzoyloxymethyl and Glycylaminobenzoyloxymethyl Esters of 7β-[2-(2-Aminothiazol-4yl)-(Z)-2-methoxyiminoacetamido]-3-methyl-3-cephem-4-carboxylic Acid", Chem. Parm. Bulletin, vol. 32(2), pp. 692-698, 1984.

(Continued)

Primary Examiner — Julie Ha
(74) *Attorney, Agent, or Firm* — Bing Hai

(57) ABSTRACT

Protease activated receptor 4 (PAR4) agonist peptides are disclosed. These peptides are useful for developing robust PAR4 receptor assays.

16 Claims, 1 Drawing Sheet

(56) References Cited

OTHER PUBLICATIONS

King, D.S. et al., "A cleavage method which minimizes side reactions following Fmoc solid phase peptide synthesis", Int. J. Peptide Protein Res., vol. 36, pp. 255-266, 1990.

King F.D., ed., Medicinal Chemistry: Principles and Practice, The Royal Society of Chemistry, Cambridge, UK (2nd Edition, reproduced, 2006.

Lee, Fang-Yu et al., "Synthesis of 1-Benzyl-3-(5'-hydroxymethyl-2'-furyl)indazole Analogues as Novel Antiplatelet Agents" J. Med. Chem., vol. 44, pp. 3746-3749, 2001.

Levine, Mark et al., "A Comparison of Low-Molecular-Weight Heparin Administered Primarily at Home with Unfractionated Heparin Administered in the Hospital for Proximal Deep-Vein Thrombosis", The New England Journal of Medicine, vol. 334(11), No. 677-681, 1996.

Lewis, R.J., ed., *Hawley's Condensed Chemical Dictionary*, 13th Edition, John Wiley & Sons, Inc. New York, 1997.

Rautio, J. (Editor). *Prodrugs and Targeted Delivery* (*Methods and Principles in Medicinal Chemistry*) vol. 47, Wiley-VCH, 2011.

Reddy, D.S. et al., "Synthesis and Conformational Studies of Dipeptides Constrained by Disubstituted 3-(Aminoethoxy)propionic Acid Linkers", JOC, vol. 69, pp. 1716-1719, 2004.

Seiler, S.M., "Thrombin Receptor Antagonists", Seminars in Thrombosis and Hemostasis, vol. 22(3), pp. 223-232, 1996.

Soslau, G. et al., "Unique Pathway of Thrombin-induced Platelet Aggregation Mediated by Glycoprotein 1b", The Journal of Biological Chemistry, vol. 276(24), pp. 21173-21183, 2001.

Stanjek, V. et al., Biosynthesis of Angular Furanocoumarins: Mechanism and Stereochemistry of the Oxidative Dealkylation of Columbianetin to Angelicin in *Heracleum mantegazzianum* (Apiaceae). Helvetica Chimica Acta, vol. 81, pp. 1596-1607, 1998.

Stewart, J.M. et al., Solid-Phase Peptide Synthesis, 2nd Edition, Pierce Chemical Co., Rockford, IL, Published, 1980.

Testa, B. et al., *Hydrolysis in Drug and Prodrug Metabolism. Chemistry, Biochemistry and Enzymology*, VHCA and Wiley-VCH, Zurich, Switzerland, 2003.

Tricoci, P. et al., "Thrombin-Receptor Antagonist Vorapaxar in Acute Coronary Syndromes", The New England Journal of Medicine, vol. 366 (1), pp. 20-33, 2012.

Wermuth, C.G., ed., *The Practice of Medicinal Chemistry*, 3rd Edition, Academic Press, San Diego, CA, 2008.

Widder, K. et al., eds., *Methods in Enzymology*, vol. 112, pp. 309-396, Academic Press, 1985.

Wong, P.C. et al., "Nonpeptide Factor Xa Inhibitors II. Antithrombotic Evaluation in a Rabbit Model of Electrically Induced Carotid Artery Thrombosis", The Journal of Pharmacology and Experimental Therapeutics, vol. 295(1), pp. 212-218, 2000.

Wu, Chin-Chung et al., "Selective Inhibition of Protease-activated Receptor 4-dependent Platelet Activation by YD-3", Thromb Haemost vol. 87, pp. 1026-1033, 2002.

Wuts et al., *Greene's Protective Groups in Organic Synthesis*, 4th Edition, Wiley-Interscience, 2006.

Zheng, K.B. et al., "Synthesis and antitumor activity of N-acetylamino-(5-alkyl/aryl-1,3,4-thiadiazole-2-yl)-5-fluorouracil derivatives", Chinese Chemical Letters, vol. 19 pp. 1281-1284, 2008.

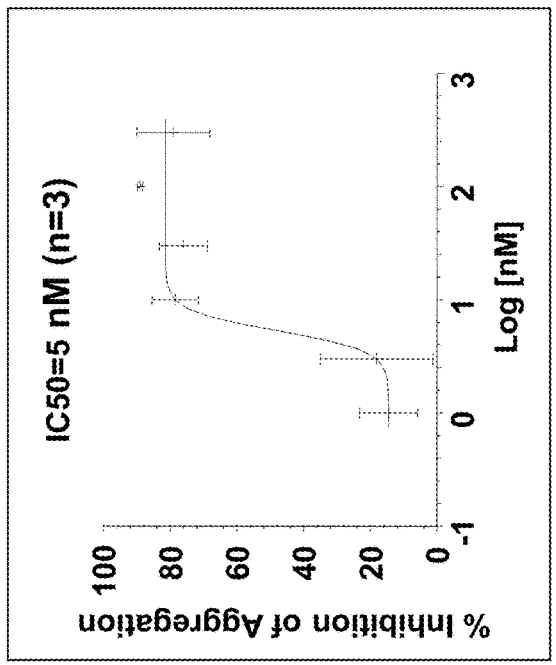
Fig 1B. Inhibition of Platelet Aggregation Dose-Response Curve
Example 3
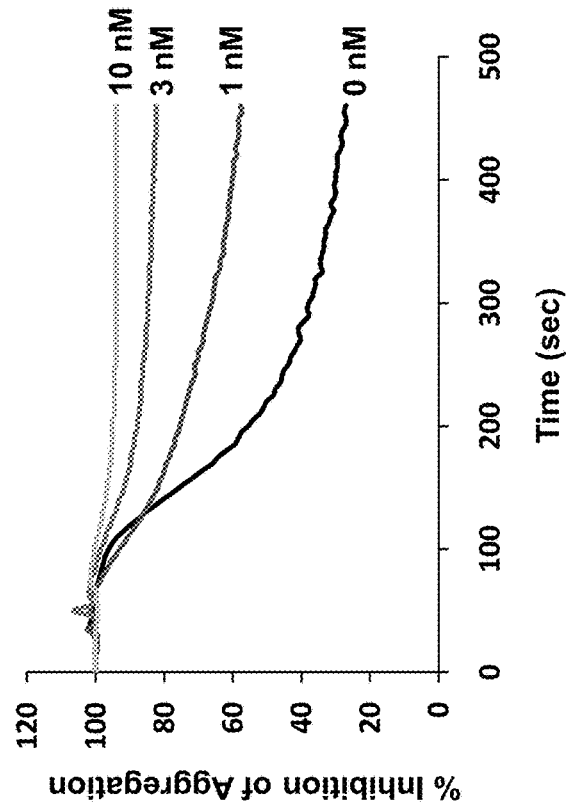
Fig 1A. Human Washed Platelet Aggregation Induced by 1.5 nM Alpha-Thrombin
Example 3

SEQUENCE LISTING

<160> NUMBER OF SEQ ID NOS: 35

<210> SEQ ID NO 1
<211> LENGTH: 6
<212> TYPE: PRT
<213> ORGANISM: Artificial Sequence
<220> FEATURE:
<223> OTHER INFORMATION: Description of Artifical Sequence Synthetic

```
      Peptide

<400> SEQUENCE: 1

Ala Tyr Pro Gly Lys Phe
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artifical Sequence Synthetic
      Peptide

<400> SEQUENCE: 2

Ala Tyr Pro Gly Trp Leu Val Lys Asn Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))

<400> SEQUENCE: 3

Ala Xaa Pro Gly Trp Leu Val Lys Asn Gly
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))

<400> SEQUENCE: 4

Ala Xaa Pro Gly Trp Leu Val Lys Asn
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is(S)-2-amino-3-(4-fluorophenyl)propanoic
      acid (abbreviated as Phe(4-F))

<400> SEQUENCE: 5

Ala Xaa Pro Gly Trp Leu Val Lys
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))

<400> SEQUENCE: 6

Ala Xaa Pro Gly Trp Leu Val
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))

<400> SEQUENCE: 7

Ala Xaa Pro Gly Trp Leu
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))

<400> SEQUENCE: 8

Ala Xaa Pro Gly Trp
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))

<400> SEQUENCE: 9

Ala Xaa Pro Gly
1

<210> SEQ ID NO 10
<211> LENGTH: 4
<212> TYPE: PRT
```

```
<213> ORGANISM: Artificial Sequence
<220> FEATURE:
<223> OTHER INFORMATION: Description of Artifical Sequence Synthetic
      Peptide

<400> SEQUENCE: 10

Ala Tyr Pro Gly
1

<210> SEQ ID NO 11
<211> LENGTH: 10
<212> TYPE: PRT
<213> ORGANISM: Artificial Sequence
<220> FEATURE:
<223> OTHER INFORMATION: Description of Artifical Sequence Synthetic
      Peptide

<400> SEQUENCE: 11

Ala Tyr Pro Gly Gln Val Cys Ala Asn Asp
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa is (S)-2-amino-3-(5-hydroxy-1H-indol-3-yl)
      propanoic acid (abbreviated as Trp(5-OH))

<400> SEQUENCE: 12

Ala Xaa Pro Gly Xaa Leu Val
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa is 2-amino-3-(5-bromo-1H-indol-3-
      yl)propanoic acid (abbreviated as (D,L)-Trp(5-Br))

<400> SEQUENCE: 13

Ala Xaa Pro Gly Xaa Leu Val
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artifical Sequence Synthetic
```

```
        Peptide
<220> FEATURE:
<221> NAME/KEY: MISC_FEATURE
<222> LOCATION: (2)..(2)
<223> OTHER INFORMATION: Xaa is (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa is D-Tryptophan (abbreviated as D-Trp)

<400> SEQUENCE: 14

Ala Xaa Pro Gly Xaa Leu Val
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(benzo[b]thiophen-3-yl)
      propanoic acid (abbreviated as Bzt)

<400> SEQUENCE: 15

Ala Xaa Pro Gly Xaa Leu Val
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2,3,4,9-tetrahydro-1H-pyrido[3,4-b]
      indole-3-carboxylic (abbreviated as Tpi) acid

<400> SEQUENCE: 16

Ala Xaa Pro Gly Xaa Leu Val
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))

<400> SEQUENCE: 17
```

```
Ala Xaa Pro Gly His Leu Val
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(thiazol-4-yl)propanoic
      acid (abbreviated as Tza)

<400> SEQUENCE: 18

Ala Xaa Pro Gly Xaa Leu Val
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(thiophen-3-yl)propanoic
      acid (abbreviated as 3-Thi)

<400> SEQUENCE: 19

Ala Xaa Pro Gly Xaa Leu Val
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(furan-3-yl)propanoic acid
      (abbreviated as 3-Fur)

<400> SEQUENCE: 20

Ala Xaa Pro Gly Xaa Leu Val
1               5

<210> SEQ ID NO 21
<211> LENGTH: 7
```

```
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = Nt-benzyl-L-histidine (abbreviated as
      His(Bzl))

<400> SEQUENCE: 21

Ala Xaa Pro Gly Xaa Leu Val
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))

<400> SEQUENCE: 22

Ala Xaa Pro Gly Phe Leu Val
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))

<400> SEQUENCE: 23

Ala Xaa Pro Gly Tyr Leu Val
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(perfluorophenyl)propanoic
      acid (abbreviated as Phe(penta-F))

<400> SEQUENCE: 24
```

```
Ala Xaa Pro Gly Xaa Leu Val
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(pyridin-2-yl)propanoic
      acid (abbreviated as 2-Pya)

<400> SEQUENCE: 25

Ala Xaa Pro Gly Xaa Leu Val
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(pyridin-3-yl)propanoic
      acid (abbreviated as 3-Pya)

<400> SEQUENCE: 26

Ala Xaa Pro Gly Xaa Leu Val
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(pyridin-4-yl)propanoic
      acid (abbreviated as 4-Pya)

<400> SEQUENCE: 27

Ala Xaa Pro Gly Xaa Leu Val
1               5

<210> SEQ ID NO 28
<211> LENGTH: 7
```

```
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3,3-diphenylpropanoic acid
      (abbreviated as Dpa)

<400> SEQUENCE: 28

Ala Xaa Pro Gly Xaa Leu Val
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(6-(o-tolyl)pyridin-3-yl)
      propanoic acid (abbreviated as 3-Pya(4-Tolyl))

<400> SEQUENCE: 29

Ala Xaa Pro Gly Xaa Leu Val
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(2'-methyl-[1,1'-biphenyl]-
      4-yl)propanoic (abbreviated as Bip(2-Methyl)) acid

<400> SEQUENCE: 30

Ala Xaa Pro Gly Xaa Leu Val
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
```

```
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(naphthalen-1-yl)propanoic
      acid (abbreviated as 1-Naphthyl-Ala)

<400> SEQUENCE: 31

Ala Xaa Pro Gly Xaa Leu Val
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(naphthalen-2-yl)propanoic
      acid (abbreviated as 2-Naphthyl-Ala)

<400> SEQUENCE: 32

Ala Xaa Pro Gly Xaa Leu Val
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S)-2-amino-3-(4-(benzyloxy)
      phenyl)propanoic acid (abbreviated as Tyr(Bzl))

<400> SEQUENCE: 33

Ala Xaa Pro Gly Xaa Leu Val
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artifical Sequence Synthetic
      Peptide
<220> FEATURE:
<221> NAME/KEY: MISC_FEATURE
<222> LOCATION: (2)..(2)
<223> OTHER INFORMATION: Xaa = (S)-2-amino-3-(4-fluorophenyl)propanoic
      acid (abbreviated as Phe(4-F))
<220> FEATURE:
<221> NAME/KEY: MISC_FEATURE
<222> LOCATION: (5)..(5)
<223> OTHER INFORMATION: Xaa = (S,E)-2-amino-5-phenylpent-4-enoic acid
```

(abbreviated as Styryl-Ala)

<400> SEQUENCE: 34

Ala Xaa Pro Gly Xaa Leu Val
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artifical Sequence Synthetic
      Peptide

<400> SEQUENCE: 35

Ser Phe Phe Leu Arg Arg
1               5

PAR4 AGONIST PEPTIDES

RELATED APPLICATIONS

This present application is a continuation of U.S. patent application Ser. No. 14/554,387, filed Nov. 26, 2014, which is a continuation of U.S. patent application Ser. No. 13/869,093, filed Apr. 24, 2013, now U.S. Pat. No. 8,927,688, which claims priority benefit to U.S. Provisional Application No. 61/638,577, filed Apr. 26, 2012 and U.S. Provisional Application No. 61/781,538, filed Mar. 14, 2013, the contents of all of which are herein incorporated by reference in their entirety.

FIELD OF THE INVENTION

The present invention provides novel peptides that bind to the PAR4 receptor and have agonist or partial agonist activity. The peptides can be used to develop robust PAR4 receptor assays.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", J. Med. Chem., 4-((22):3746-3749 (2001) discloses in the abstract that the compound

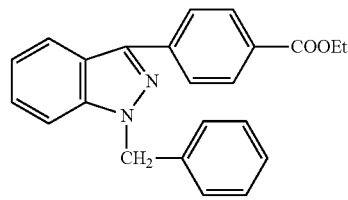

58

"was found to be a selective and potent inhibitor or protease-activated receptor type 4 (PAR4)-dependent platelet activation."

Compound 58 is also referred to as YD-3 in Wu, C-C. et al., "Selective Inhibition of Protease-activated Receptor 4-dependent Platelet Activation by YD-3", Thromb. Haemost., 87:1026-1033 (2002). Also, see Chen, H. S. et al., "Synthesis and platelet activity", J. Bioorg. Med. Chem., 16:1262-1278 (2008).

EP1166785 A1 and EP0667345 disclose various pyrazole derivatives which are useful as inhibitors of platelet aggregation.

SUMMARY OF THE INVENTION

Some embodiments of the present invention relate to peptides that modulate the PAR4 receptor as agonists or partial agonists of the receptor. These peptides exhibit improved biological activity relative to a native PAR4 agonist sequence known in the art, thus making them ideal candidates for PAR4 receptor assay development.

In some embodiments, the peptide is an isolated peptide comprising an amino acid sequence of Formula I:

Ala-Xaa$_1$-Pro-Gly-Xaa$_2$-Leu-Val  (Formula I)

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus is amidated.

In some embodiments, the PAR4 agonist peptide comprises a peptide selected from SEQ ID NOS: 1-8, 12-16 and 18-34. In other embodiments, the PAR4 agonist peptide comprises a peptide selected from SEQ ID NOS: 2-7, 12, 13, 15, 18-24 and 26-34. In other embodiments, the PAR4 agonist peptide comprises the peptide of SEQ ID NO: 3.

In some embodiments, the PAR4 agonist peptide comprises an amino acid sequence of Formula I and further comprises a Lys after Val. In other embodiments, the PAR4 agonist peptide comprises an amino acid sequence of Formula I and further comprises Lys-Asn after Val. In other embodiments, the PAR4 agonist peptide comprises an amino acid sequence of Formula I and further comprises Lys-Asn-Gly after Val.

In other embodiments, the PAR4 agonist peptide further comprises a Lys after Val, as shown below in Formula II:

Ala-Xaa$_1$-Pro-Gly-Xaa$_2$-Leu-Val-Lys  (Formula II)

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe (penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and the C-terminus is amidated.

In other embodiments, the PAR4 agonist peptide further comprises Lys-Asn after Val, as shown below in Formula III:

Ala-Xaa$_1$-Pro-Gly-Xaa$_2$-Leu-Val-Lys-Asn     (Formula III)

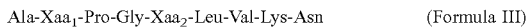

wherein, the amino terminus of the peptide is free;

X$_{aa1}$ is selected from Tyr and Phe(4-F);

X$_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and the C-terminus is amidated.

In other embodiments, the PAR4 agonist peptide further comprises Lys-Asn-Gly after Val, as shown below in Formula IV:

Ala-Xaa$_1$-Pro-Gly-Xaa$_2$-Leu-Val-Lys-Asn-Gly     (Formula IV)

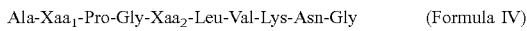

wherein, the amino terminus of the peptide is free;

X$_{aa1}$ is selected from Tyr and Phe(4-F);

X$_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and the C-terminus is amidated.

It has been found that imidazothiadiazole and imidazopyridazine compounds in accordance with the present invention are PAR4 antagonists which inhibit platelet aggregation in an alpha-thrombin induced platelet aggregation assay.

Accordingly, the present invention provides novel imidazothiadiazole analogues and imidazopyridazine analogues which are PAR4 antagonists and are useful as selective inhibitors of platelet aggregation, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other features and advantages of the invention will be apparent from the following detailed description and claims.

BRIEF DESCRIPTION OF THE FIGURES

FIG. 1A is a graph which shows the effectiveness of the Example 3 compound in inhibiting aggregation of human washed platelets stimulated by 1.5 nM alpha-thrombin; and FIG. 1B is a graph which shows the IC$_{50}$ of the Example 3 compound in inhibiting alpha-thrombin-induced platelet aggregation.

DETAILED DESCRIPTION

PAR4 Agonist Peptides

An embodiment of the present invention provides PAR4 agonist peptides having improvement in potency relative to a known PAR4 agonist peptide, AYPGKF (SEQ ID NO: 1). See Faruqi, T. R., et al. J Biol Chem, 2000. 275(26): p. 19728-34. In some embodiments of the present invention, the PAR4 agonist peptides have up to a up to a 20-fold improvement in potency relative to SEQ ID NO: 1. In other embodiments, the PAR4 peptides have up to a 60-fold improvement in potency relative to SEQ ID NO: 1. In other embodiments, the PAR4 peptides have up to a 100-fold improvement in potency relative to SEQ ID NO: 1. As a result of the improved potency, the PAR4 agonist peptides of the present invention can be used to develop robust PAR4 receptor assays with improved sensitivity and specificity.

The definitions provided herein apply, without limitation, to the terms as used throughout this specification, unless otherwise limited in specific instances.

As used herein, the term "PAR4 agonist peptide" means a peptide that can fully or partially activate the PAR4 receptor and elicit signaling events and or functional responses associated with PAR4 receptor activation. Exemplary PAR4 agonist peptides are SEQ ID NOS: 1-8, 12-16 and 18-34, shown in Table 1, wherein the N-termini of the sequences are free and the C-termini of the sequences are amidated. In Table 1, the numbers 1-10 at the top of the chart reflect the position of the amino acid within the peptide, with position 1 starting at the N-terminus.

TABLE 1

| SEQ ID NO. | 1 | 2 | 3 | 4 | 5 | 6 | 7 | 8 | 9 | 10 |
|---|---|---|---|---|---|---|---|---|---|---|
| 1 | A | Y | P | G | K | F | | | | |
| 2 | A | Y | P | G | W | L | V | K | N | G |
| 3 | A | Phe(4-F) | P | G | W | L | V | K | N | G |
| 4 | A | Phe(4-F) | P | G | W | L | V | K | N | |
| 5 | A | Phe(4-F) | P | G | W | L | V | K | | |
| 6 | A | Phe(4-F) | P | G | W | L | V | | | |
| 7 | A | Phe(4-F) | P | G | W | L | | | | |
| 8 | A | Phe(4-F) | P | G | W | | | | | |
| 9 | A | Phe(4-F) | P | G | | | | | | |
| 10 | A | Y | P | G | | | | | | |
| 11 | A | Y | P | G | Q | V | C | A | N | D |
| 12 | A | Phe(4-F) | P | G | Trp(5-OH) | L | V | | | |
| 13 | A | Phe(4-F) | P | G | (D, L)-Trp(5-Br) | L | V | | | |
| 14 | A | Phe(4-F) | P | G | D-Trp | L | V | | | |
| 15 | A | Phe(4-F) | P | G | Bzt | L | V | | | |
| 16 | A | Phe(4-F) | P | G | Tpi | L | V | | | |
| 17 | A | Phe(4-F) | P | G | H | L | V | | | |
| 18 | A | Phe(4-F) | P | G | Tza | L | V | | | |
| 19 | A | Phe(4-F) | P | G | 3-Thi | L | V | | | |
| 20 | A | Phe(4-F) | P | G | 3-Fur | L | V | | | |

TABLE 1-continued

| SEQ ID NO. | 1 | 2 | 3 | 4 | 5 | 6 | 7 | 8 | 9 | 10 |
|---|---|---|---|---|---|---|---|---|---|---|
| 21 | A | Phe(4-F) | P | G | His(Bzl) | L | V | | | |
| 22 | A | Phe(4-F) | P | G | F | L | V | | | |
| 23 | A | Phe(4-F) | P | G | Y | L | V | | | |
| 24 | A | Phe(4-F) | P | G | Phe(penta-F) | L | V | | | |
| 25 | A | Phe(4-F) | P | G | 2-Pya | L | V | | | |
| 26 | A | Phe(4-F) | P | G | 3-Pya | L | V | | | |
| 27 | A | Phe(4-F) | P | G | 4-Pya | L | V | | | |
| 28 | A | Phe(4-F) | P | G | Dpa | L | V | | | |
| 29 | A | Phe(4-F) | P | G | 3-Pya(4-Tolyl) | L | V | | | |
| 30 | A | Phe(4-F) | P | G | Bip(2-Methyl) | L | V | | | |
| 31 | A | Phe(4-F) | P | G | 1-Naphthyl-Ala | L | V | | | |
| 32 | A | Phe(4-F) | P | G | 2-Naphthyl-Ala | L | V | | | |
| 33 | A | Phe(4-F) | P | G | Tyr(Bzl) | L | V | | | |
| 34 | A | Phe(4-F) | P | G | Styryl-Ala | L | V | | | |

In some embodiments, a PAR4 agonist peptide has an ED50<100 μM. In other embodiments, a PAR4 agonist peptide has an ED50<10 μM. Exemplary assays for measuring PAR4 agonist activity include, but are not limited to, the platelet aggregation assay described in Example G and the FLIPR assay described in Example H.

In some embodiments, the peptide is an isolated peptide comprising an amino acid sequence of Formula I:

Ala-$Xaa_1$-Pro-Gly-$Xaa_2$-Leu-Val    (Formula I)

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe (penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus is amidated.

In some embodiments, the PAR4 agonist peptide comprises a peptide selected from SEQ ID NOS: 1-8, 12-16 and 18-34. In other embodiments, the PAR4 agonist peptide comprises a peptide selected from SEQ ID NOS: 2-7, 12, 13, 15, 18-24 and 26-34. In other embodiments, the PAR4 agonist peptide comprises the peptide of SEQ ID NO: 3.

In some embodiments, the PAR4 agonist peptide comprises an amino acid sequence of Formula I and further comprises a Lys after Val. In other embodiments, the PAR4 agonist peptide comprises an amino acid sequence of Formula I and further comprises Lys-Asn after Val. In other embodiments, the PAR4 agonist peptide comprises an amino acid sequence of Formula I and further comprises Lys-Asn-Gly after Val.

In other embodiments, the PAR4 agonist peptide further comprises a Lys after Val, as shown below in Formula II:

Ala-$Xaa_1$-Pro-Gly-$Xaa_2$-Leu-Val-Lys    (Formula II)

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe (penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus is amidated.

In other embodiments, the PAR4 agonist peptide further comprises a Lys-Asn after Val, as shown below in Formula III:

Ala-$Xaa_1$-Pro-Gly-$Xaa_2$-Leu-Val-Lys-Asn    (Formula III)

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe (penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and the C-terminus is amidated.

In other embodiments, the PAR4 agonist peptide further comprises a Lys-Asn-Gly after Val, as shown below in Formula IV:

Ala-$Xaa_1$-Pro-Gly-$Xaa_2$-Leu-Val-Lys-Asn-Gly    (Formula IV)

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Bzt, Tpi, His, Tza, 3-Thi, 3-Fur, His(Bzl), Phe, Tyr, Phe (penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus is amidated.

An amino acid includes a compound represented by the general structure:

$$\begin{array}{cc} \text{COOH} & \text{COOH} \\ H_2N - \underset{R'}{\overset{|}{C}} - R & R - \underset{R'}{\overset{|}{C}} - NH_2 \\ \text{L- or S-}\alpha\text{-amino acid} & \text{D- or R-}\alpha\text{-amino acid} \\ \text{(if R = H)} & \text{(if R = H)} \end{array}$$

where R and R' are as discussed herein. Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "a" carbon is commonly referred to as the "L" or "natural" configuration, with the exception of L-Cysteine, which possesses an absolute "R" configuration. In the case where both the "R" and the "R'" (prime) substituents equal hydrogen, the amino acid is glycine and is not chiral. The amino acids recited herein are in the "L" configuration unless noted otherwise.

Amino acids may be referred to herein by either their commonly known three-letter symbols or by the one-letter symbols recommended by the IUPAC-IUB Biochemical Nomenclature Commission. A PAR4 agonist peptide of the present invention may include naturally encoded amino acids (common amino acids) as well as non-naturally encoded amino acids. A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. Exemplary non-naturally encoded amino acids that may be present in the PAR4 agonist peptides are shown below.

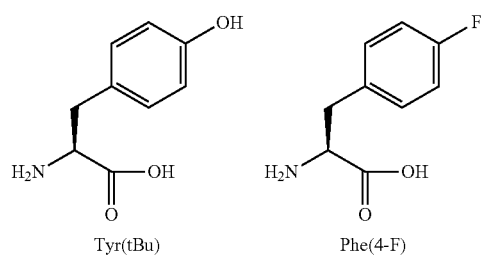
Tyr(tBu)  Phe(4-F)
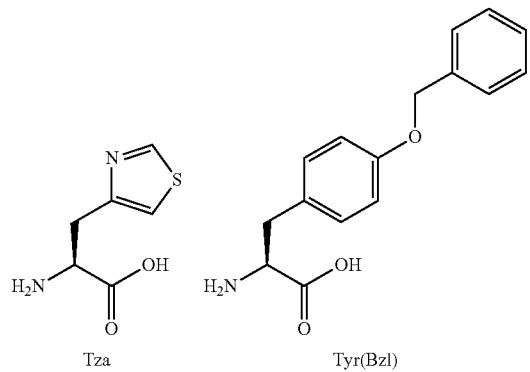
Tza  Tyr(Bzl)
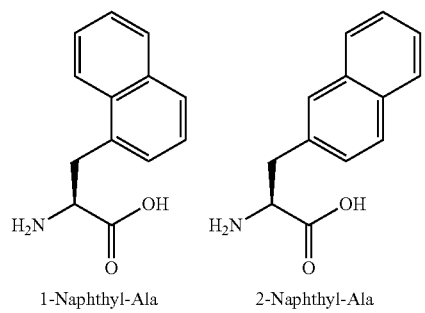
1-Naphthyl-Ala  2-Naphthyl-Ala
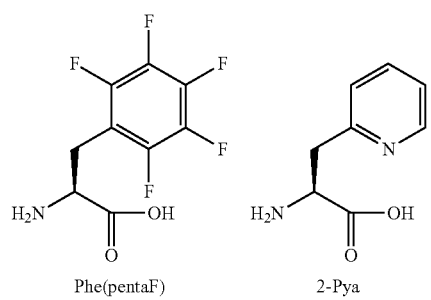
Phe(pentaF)  2-Pya
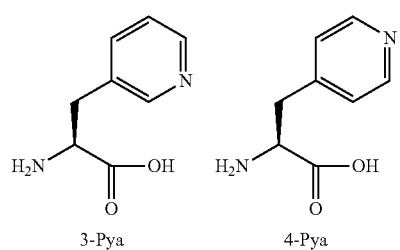
3-Pya  4-Pya
-continued
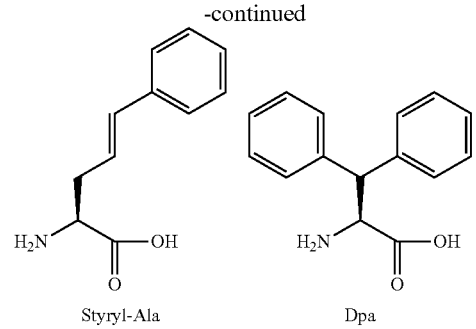
Styryl-Ala  Dpa
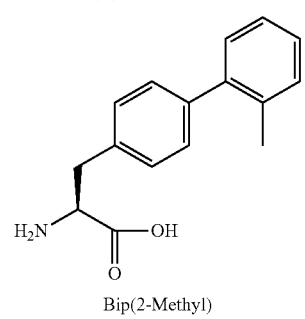
Bip(2-Methyl)
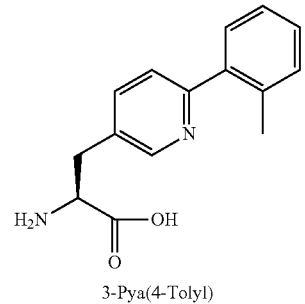
3-Pya(4-Tolyl)
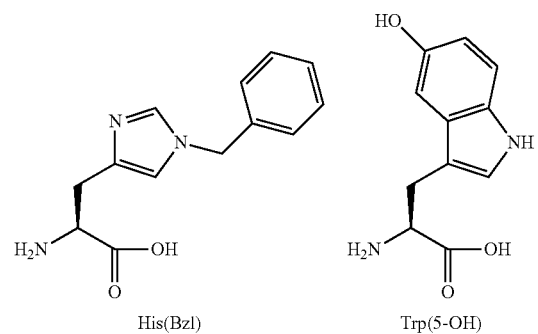
His(Bzl)  Trp(5-OH)
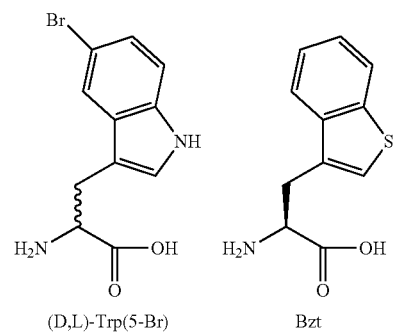
(D,L)-Trp(5-Br)  Bzt

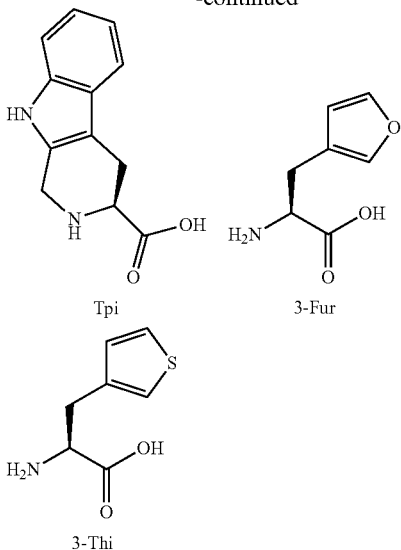

Tpi    3-Fur

3-Thi

The PAR4 agonist peptides disclosed herein show improved affinity for the PAR-4 receptor and may be used as agonists to activate the PAR-4 receptor in PAR4 receptor assays.

The peptides described herein may be produced by chemical synthesis using various solid-phase techniques such as those described in Barany, G. et al., *The Peptides: Analysis, Synthesis, Biology*, Volume 2: "Special Methods in Peptide Synthesis, Part A", pp. 3-284, Gross, E. et al., eds., Academic Press, New York, publ. (1980); and in Stewart, J. M. et al., *Solid-Phase Peptide Synthesis*, 2nd Edition, Pierce Chemical Co., Rockford, Ill., publ. (1984). The desired strategy is based on the Fmoc (9-Fluorenylmethyl methyloxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in *The Peptides: Analysis, Synthesis, Biology*, Volume 9: "Special Methods in Peptide Synthesis, Part C", pp. 1-38, Undenfriend, S. et al., eds., Academic Press, San Diego, publ. (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively. Alternatively, in cases where a C-terminal amino alcohol is present, the C-terminal residue may be attached to 2-Methoxy-4-alkoxybenzyl alcohol resin (SASRIN™, Bachem Bioscience, Inc., King of Prussia, Pa.) as described herein and, after completion of the peptide sequence assembly, the resulting peptide alcohol is released with LiBH4 in THF (see Stewart, J. M. et al., supra, p. 92).

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBT or HOAT active esters produced from DIC/HOBT, HBTU/HOBT, BOP, PyBOP, or from DIC/HOAT, HATU/HOAT, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the PAR4 agonist peptides described herein can be carried out by using a peptide synthesizer, such as an Advanced ChemTech Multiple Peptide Synthesizer (MPS396Ω) or an Advanced ChemTech Model 90 synthesizer or an Applied Biosystems Inc. peptide synthesizer (ABI 433A). The MPS396Ω synthesizer was used to prepare up to 96 peptides simultaneously. The Advanced ChemTech Model 90 Synthesizer was used to prepare common peptide sequences on a large scale (up to 5 mmol of resin). The ABI 433A synthesizer was used to prepare individual peptides on a scale up to 0.25 mmol. In all cases, the stepwise solid phase peptide synthesis was carried out utilizing the Fmoc/t-butyl protection strategy described herein. Exemplary orthogonally protected amino acids that can be used in solid phase synthesis are shown below.

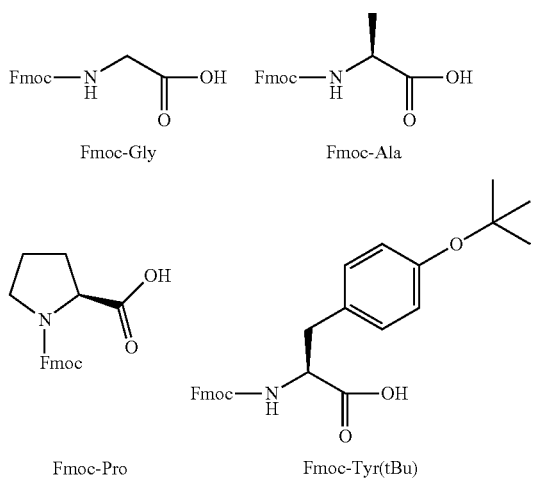

Fmoc-Gly    Fmoc-Ala

Fmoc-Pro    Fmoc-Tyr(tBu)

-continued

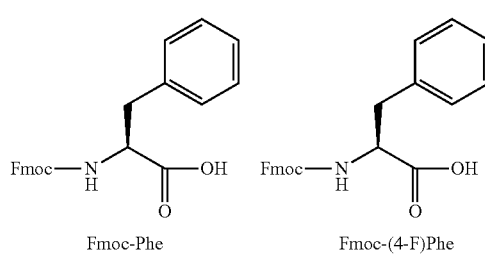

Fmoc-Phe    Fmoc-(4-F)Phe

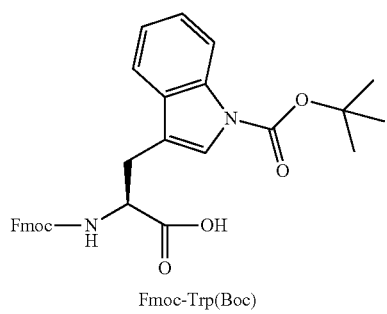

Fmoc-Trp(Boc)

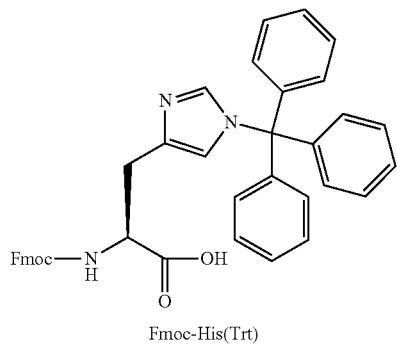

Fmoc-His(Trt)

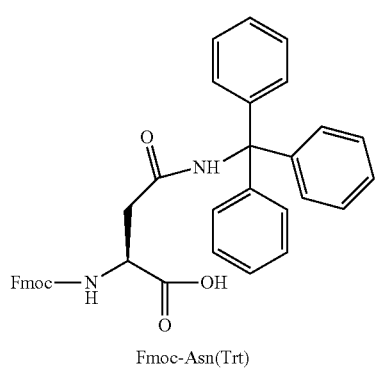

Fmoc-Asn(Trt)

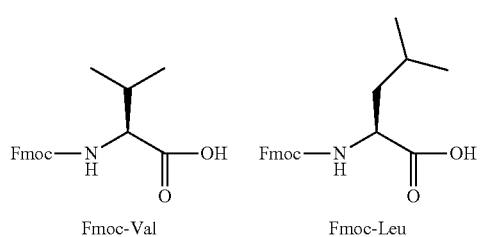

Fmoc-Val    Fmoc-Leu

-continued

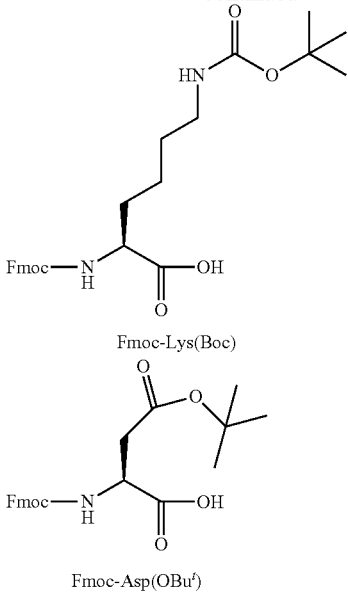

Fmoc-Lys(Boc)

Fmoc-Asp(OBu$^t$)

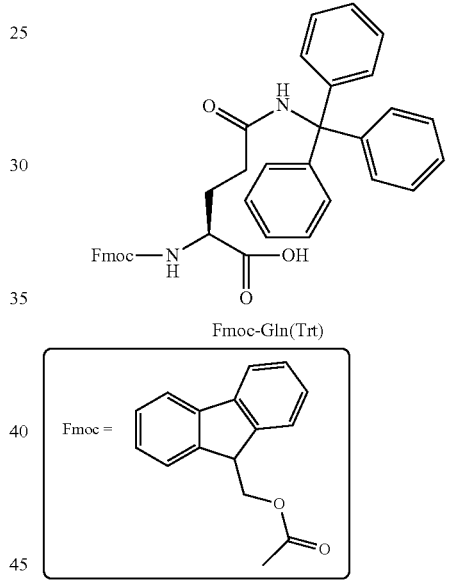

Fmoc-Gln(Trt)

Fmoc =

The peptidyl-resin precursors for their respective peptides may be cleaved and deprotected using any standard procedure (see, for example, King, D. S. et al., *Int. J. Peptide Protein Res.*, 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with Et$_2$O or is redissolved directly into DMSO or 50% aqueous acetic acid for purification by preparative HPLC. Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

The following abbreviations are employed in the Examples and elsewhere herein:
Ph=phenyl
Bz or Bnz=benzyl
i-Bu=iso-butyl
i-Pr=iso-propyl
Me=methyl
Et=ethyl
Pr=n-propyl
Bu=n-butyl
t-Bu=tert-butyl
Trt=trityl
TMS=trimethylsilyl
TIS=Triisopropylsilane
Et$_2$O=diethyl ether
HOAc or AcOH=acetic acid
AcCN or CH$_3$CN=acetonitrile
DMF=N,N-dimethylformamide
EtOAc=ethyl acetate
TFA=trifluoroacetic acid
NMM=N-methylmorpholine
NMP=N-methylpyrrolidone
DCM=dichloromethane
TEA=triethylamine
min=minute(s)
h or hr=hour(s)
L=liter
mL or ml=milliliter
μL=microliter
g=gram(s)
mg=milligram(s)
mol=mole(s)
mmol=millimole(s)
meq=milliequivalent
rt or RT=room temperature
aq.=aqueous
BOP reagent=benzotriazol-1-yloxy-tris-dimethylamino-phosphonium hexafluorophosphate (Castro's reagent)
PyBOP reagent=benzotriazol-1-yloxy-tripyrrolidino phosphonium hexafluorophosphate
HBTU=2-(1H-Benzotriazol-1-yl)-1,1,3,3-tetramethyl-uronim hexafluorophosphate
HATU=O-(7-Azabenzotriazol-1-yl)-1,1,3,3-tetramethyl-uronim hexafluorophosphate
HCTU=2-(6-Chloro-1-H-benzotriazol-1-yl)-1,1,3,3-tetramethyluronium hexafluorophosphate
DIEA=Diisopropylethylamine
Fmoc or FMOC=fluorenylmethyloxycarbonyl
Boc or BOC=tert-butyloxycarbonyl
HOBT or HOBT●H$_2$O=1-hydroxybenzotriazole hydrate
Cl-HOBt=6-Chloro-benzotriazole
HOAT=1-hydroxy-7-azabenzotriazole
HPLC=high performance liquid chromatography
LC/MS=high performance liquid chromatography/mass spectrometry
NMR=nuclear magnetic resonance Imidazothiadiazole and Imidazopyridazine Compounds of the Invention In a first aspect, the present invention provides imidazothiadiazole or imidazopyridazine compound of Formula I having the structure:

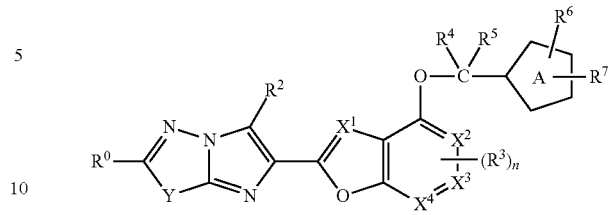

or a stereoisomer, tautomer, pharmaceutically acceptable salt, solvate or prodrug ester thereof, wherein:
R$^0$ is R$^1$ or R$^{1a}$;
Y is S or —CR$^8$=CR$^9$—, so that

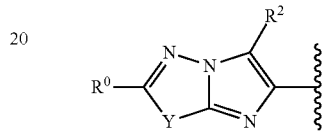

is an 8- or 9-membered bicyclic heteroaryl ring which contains one nitrogen in each ring and one bridgehead nitrogen, namely

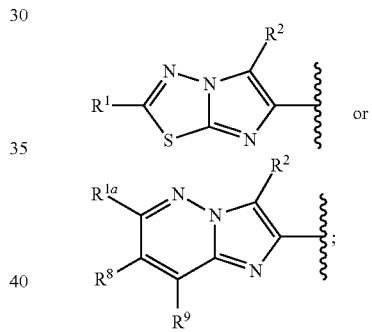

R$^1$ is selected from:
halo, such as F, Cl, Br or I,
C$_1$-C$_4$ alkyl, such as methyl, ethyl, n-propyl or isopropyl,
C$_1$-C$_4$ alkoxy, for example, CH$_3$O,
halo-C$_1$-C$_2$-alkyl, which contains 1 to 5 halogens, where halo is, for example, F or Cl, including, for example, CF$_3$, CF$_3$CF$_2$, —CF$_2$CH$_3$,

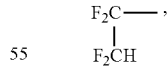

F$_2$C(Cl)—, and CHFCH$_3$, and
C$_1$-C$_4$ alkylthio, such as CH$_3$S;
R$^{1a}$ is selected from:
H,
halo, such as F, Cl, Br or I,
C$_1$-C$_4$ alkyl, such as CH$_3$, C$_2$H$_5$, n-C$_3$H$_7$, or i-C$_3$H$_7$,
C$_1$-C$_4$ alkoxy, such as CH$_3$O,
halo-C$_1$-C$_2$-alkyl, which contains 1 to 5 halogens, where halo is, for example, F or Cl, such as CF$_3$, CF$_3$CF$_2$, —CF$_2$CH$_3$,

F$_2$C(Cl), CHF$_2$, and CHFCH$_3$, and
C$_1$-C$_4$ alkylthio, such as CH$_3$S;
R$^8$ and R$^9$ are independently selected from:
H,
C$_1$-C$_4$ alkyl, such as CH$_3$,
halo, such as Cl or F,
C$_1$-C$_4$ alkoxy, such as CH$_3$O,
CF$_3$,
CF$_3$O,
CHF$_2$, and
OH;
provided that at least one of R$^{1a}$, R$^8$ and R$^9$ is other than H;
R$^2$ is selected from:
H,
halo, such as F or Cl,
C$_1$-C$_4$ alkyl,
C$_1$-C$_4$ alkoxy, such as methoxy, and
cyano;
X$^1$ is CH, N or CR$^{10}$,
X$^2$, X$^3$ and X$^4$ are independently selected from CR$^3$ or N;
R$^3$ is H, C$_1$-C$_4$ alkoxy, such as CH$_3$O, C$_1$-C$_4$ alkylthio, such as CH$_3$S, halo, such as F or Cl, CF$_3$O, CHF$_2$O, or halo-C$_1$-C$_2$-alkyl, which contains 1 to 5 halogens, such as CF$_3$ or CHF$_2$;
R$^4$ and R$^5$ are independently selected from H and C$_1$-C$_4$ alkyl, such as methyl, or can be taken together with the carbon to which they are attached to form a C$_3$-C$_7$ cycloalkyl ring, such as cyclopropyl;

is a 5-membered heteroaryl ring containing at least one O, N or S atom, such as one or two N atoms and one S atom, or two or three N atoms;
R$^6$ is selected from H, halo, such as F, Cl, Br or I, OCF$_3$, CF$_3$, CHF$_2$, OCHF$_2$, OH, CN, NO$_2$, NR$^{11}$R$^{12}$, COOH, C$_1$-C$_4$ alkoxycarbonyl, (C=O)NR$^{11}$R$^{12}$, C$_1$-C$_4$ alkylsulfonyl, S(=O)$_2$NR$^{11}$R$^{12}$, C$_1$-C$_4$ alkyl substituted by 0 to 3 groups independently selected from halo, such as F, Br, Cl or I, CF$_3$, OCF$_3$, OH, hydroxy-C$_1$-C$_4$-alkyl, C$_1$-C$_4$ alkoxy, (di-C$_1$-C$_4$-alkoxy-C$_1$-C$_4$-alkyl)-C$_1$-C$_4$-alkyl, C$_1$-C$_4$ alkylthio, and di-C$_1$-C$_4$-alkylaminophenyl-C$_1$-C$_4$-alkyl; or
R$^6$ is A-D-, where:
D is a linker, which is selected from:
a single bond,
—O—,
—S—,

C$_1$-C$_4$ alkylene, such as —CH$_2$—,
C$_1$-C$_4$ alkyleneoxy, such as —CH$_2$O—,
C$_1$-C$_4$ alkylenethio, such as —CH$_2$S—,
C$_1$-C$_4$ alkyleneoxy-C$_1$-C$_4$-alkylene, such as —CH$_2$OCH$_2$—,
C$_1$-C$_4$-alkylenethio-C$_1$-C$_4$-alkylene, such as —CH$_2$SCH$_2$—,
—S—C$_1$-C$_4$-alkylene, such as —S—CH$_2$—, or
—O—C$_1$-C$_4$-alkylene, such as —O—CH$_2$—; and
A is selected from:
C$_6$-C$_{10}$ aryl (namely, phenyl or naphthyl) substituted by 0 to 3 groups independently selected from halo, such as F or Cl, C$_1$-C$_4$ alkoxy, C$_1$-C$_4$ alkyl, cyclopropyl, CF$_3$, OCF$_3$, or CF$_2$CH$_3$,
5- to 10-membered heteroaryl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl or C$_1$-C$_4$ alkyl,
4- to 10-membered heterocyclyl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl, C$_6$-C$_{10}$ aryl or C$_1$-C$_4$ alkyl, or
C$_3$-C$_6$ cycloalkyl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl, C$_6$-C$_{10}$ aryl or C$_1$-C$_4$ alkyl;
R$^{11}$ and R$^{12}$ are independently, at each occurrence, selected from:
H,
C$_1$-C$_4$ alkyl, such as CH$_3$,
—(CH$_2$)$_n{}^1$-phenyl substituted by 0 to 3 groups independently selected from halo, C$_1$-C$_4$ alkoxy, C$_1$-C$_4$ alkyl, cyclopropyl, CF$_3$, OCF$_3$, OCHF$_2$, and cyano,
—(CH$_2$)$_n{}^1$-C$_3$-C$_6$-cycloalkyl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl or C$_1$-C$_4$ alkyl,
—(CH$_2$)$_n{}^1$-4- to 10-membered-heterocyclyl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl or C$_1$-C$_4$ alkyl,
—(CH$_2$)$_n{}^1$-5- to 10-membered-heteroaryl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl or C$_1$-C$_4$ alkyl,
di-C$_1$-C$_4$-alkylamino-C$_1$-C$_4$-alkyl,
C$_1$-C$_4$-alkylcarbonylamino-C$_1$-C$_4$-alkyl,
di-C$_1$-C$_4$-alkoxy-C$_1$-C$_4$-alkyl,
di-C$_1$-C$_4$-alkylaminophenyl,
cyano-C$_1$-C$_4$-alkyl,
C$_1$-C$_4$-alkoxy-C$_1$-C$_4$-alkyl,
alternatively, R$^{11}$ and R$^{12}$, when attached to the same nitrogen, combine to form a 4- to 6-membered heterocyclic ring containing carbon atoms and 0 to 2 additional heteroatoms selected from N, NR$^{13}$, O and S(O)$_p$;
R$^{13}$ is independently, at each occurrence, selected from H, C$_1$-C$_4$ alkyl and —(CH$_2$)phenyl;
R$^7$ is selected from H, halo, such as F or Cl, and C$_1$-C$_4$ alkyl, such as CH$_3$;
R$^{10}$ is selected from C$_1$-C$_4$ alkyl, such as CH$_3$, halo, which is F, Cl, Br, or I, C$_1$-C$_4$ alkoxy, for example, CH$_3$O, and halo-C$_1$-C$_2$-alkyl, which can contain 1 to 5 halogens, where halo is F or Cl;
n, at each occurrence, is selected from 0, 1, 2 and 3;
n$^1$ is selected from 0, 1, 2, 3, 4 or 5; and
p, at each occurrence, is selected from 0, 1 and 2.
Thus, R$^6$ can be:
C$_3$-C$_6$ cycloalkyl substituted by 0 to 3 groups independently selected from halo, such as F, Br, Cl or I, CF$_3$, OCF$_3$, 5- or 6-membered heteroaryl, OH, hydroxy-C$_1$-C$_4$-alkyl or C$_1$-C$_4$ alkyl;

5- to 10-membered heteroaryl substituted by 0 to 3 groups independently selected from halo, such as F, Br, $C_1$ or I, $CF_3$, $OCF_3$, 5- or 6-membered heteroaryl, OH, hydroxy-$C_1$-$C_4$-alkyl or $C_1$-$C_4$ alkyl;

4- to 10-membered heterocyclyl substituted by 0 to 3 groups independently selected from halo, such as F, Br, $C_1$ or I, $CF_3$, $OCF_3$, 5- or 6-membered heteroaryl, OH, hydroxy-$C_1$-$C_4$-alkyl or $C_1$-$C_4$ alkyl;

$C_3$-$C_6$ cycloalkyloxy substituted by 0 to 3 groups independently selected from halo, such as F, Br, $C_1$ or I, $CF_3$, $OCF_3$, 5- or 6-membered heteroaryl, OH, hydroxy-$C_1$-$C_4$-alkyl or $C_1$-$C_4$ alkyl;

aryl, such as phenyl or naphthyl, substituted by 0 to 3 groups independently selected from halo, such as F or Cl, halo-$C_1$-$C_2$-alkyl, which contains 1 to 5 halogens, such as F, for example, $CF_3$ and —$CF_2CH_3$, $C_1$-$C_4$ alkoxy, $C_1$-$C_4$ alkyl, cyclopropyl, and $OCF_3$;

aryloxy, such as phenyloxy, wherein the aryl is substituted by 0 to 3 groups independently selected from halo, $C_1$-$C_4$ alkoxy, $C_1$-$C_4$ alkyl, cyclopropyl, $CF_3$, $OCF_3$, $OCHF_2$, and cyano;

arylthio, such as phenylthio, wherein the aryl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;

aryl-$C_1$-$C_4$-alkoxy, such as phenylalkoxy, wherein the aryl is substituted by 0 to 3 groups independently selected from halo, $C_1$-$C_4$ alkoxy, $C_1$-$C_4$ alkyl, cyclopropyl, $CF_3$, $OCF_3$, $OCHF_2$, and cyano;

5- to 10-membered heteroaryl-$C_1$-$C_4$-alkyl, wherein the heteroaryl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;

5- to 10-membered heteroaryl-$C_1$-$C_4$-alkoxy, wherein the heteroaryl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;

aryl-$C_1$-$C_4$-alkyl, such as phenylalkyl, wherein the aryl is substituted by 0 to 3 groups independently selected from halo, $C_1$-$C_4$ alkoxy, $C_1$-$C_4$ alkyl, cyclopropyl, $CF_3$, $OCF_3$, $OCHF_2$, and cyano;

di-$C_1$-$C_4$-alkylaminophenyl-$C_1$-$C_4$-alkyl;

OH;

CN;

$NO_2$;

$NR^{11}R^{12}$;

carboxy;

$C_1$-$C_4$ alkoxycarbonyl;

C(=O)$NR^{11}R^{12}$;

$C_1$-$C_4$ alkylsulfonyl; and

S(=O)$_2NR^{11}R^{12}$.

In some embodiments of the compounds of the invention of Formula I:

Y is S or CH=CH;

$X^1$ is CH or N;

$X^2$, $X^3$ and $X^4$ are each independently $CR^3$;

$R^0$ is $R^1$ or $R^{1a}$;

$R^1$ and $R^{1a}$ are selected from:

$C_1$-$C_4$ alkyl, such as $CH_3$, $C_1$-$C_4$ alkylthio, such as $CH_3S$, $C_1$-$C_4$ alkoxy, such as $CH_3O$, and halo-$C_1$-$C_2$-alkyl, which can contain 1 to 5 halo atoms, such as F and Cl;

$R^2$ is H;

$R_3$ is selected from:

$C_1$-$C_4$ alkoxy, such as $CH_3O$,

H, and halo, such as F or Cl;

n is 1; and $R^4$ and $R^5$ are each H.

Thus, the compounds of the invention may have the structures:

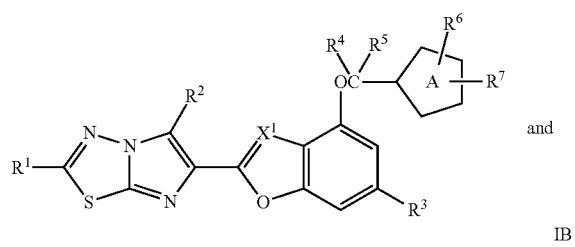

IA

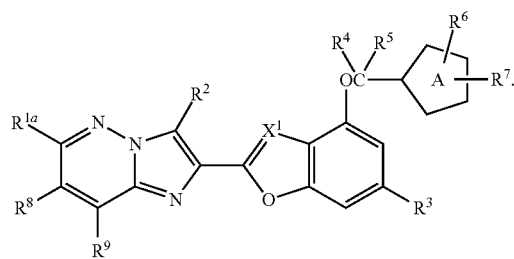

IB

In some embodiments, the present invention includes compounds having the structures:

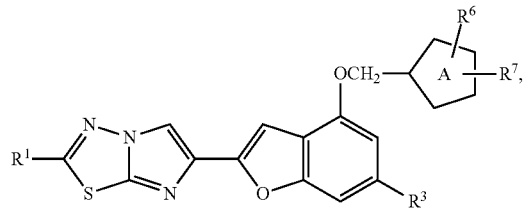

IC

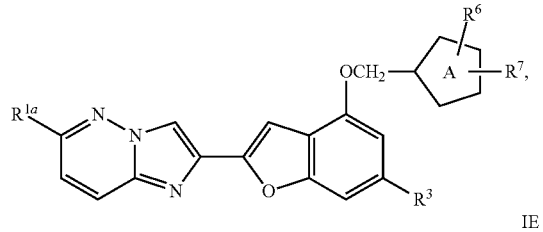

ID

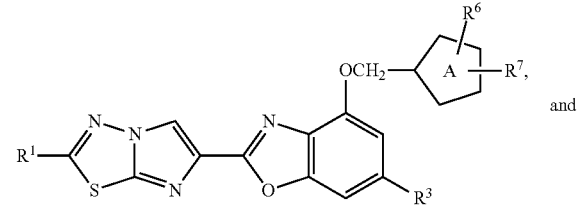

IE and

-continued

IF
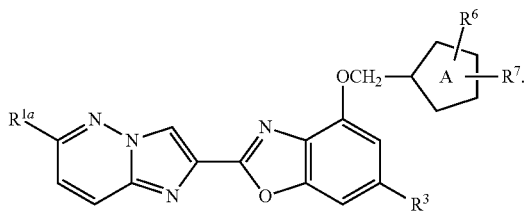

In some embodiments, the present invention includes compounds within the scope of Formula I where $R^6$ is

or $R^{6a}$ which have the structures:

IG
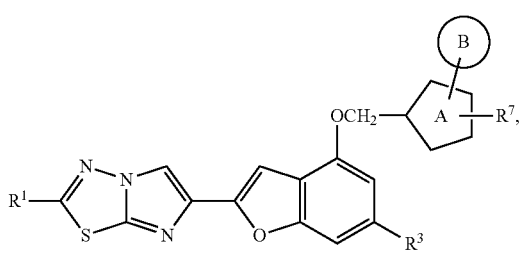

IH
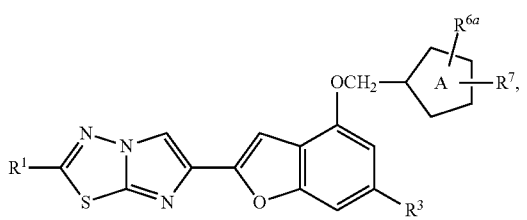

IJ
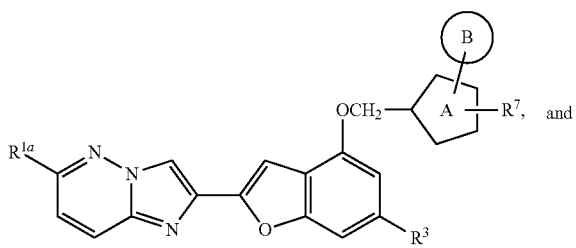 and

IK
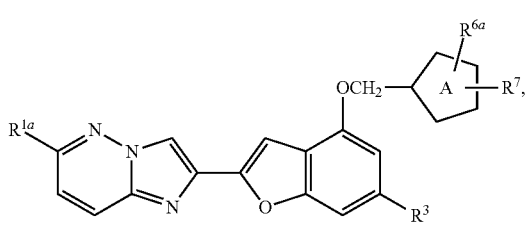

wherein:

is:
- $C_6$-$C_{10}$ aryl (namely, phenyl or naphthyl) substituted by 0 to 3 groups independently selected from halo, such as F or Cl, $C_1$-$C_4$ alkoxy, $C_1$-$C_4$ alkyl, cyclopropyl, $CF_3$, $OCF_3$, or $CF_2CH_3$,
- 5- to 10-membered heteroaryl substituted by 0 to 3 groups independently selected from halo, such as F, Br, $C_1$ or I, $CF_3$, $OCF_3$, 5- or 6-membered heteroaryl, OH, hydroxy-$C_1$-$C_4$-alkyl, such as $HOCH_2CH_2$—, $C_1$-$C_4$ alkyl, such as $CH_3$, $C_1$-$C_4$ alkoxy, such as $CH_3O$, or di-$C_1$-$C_4$-alkylamino, such as $(CH_3)_2N$,
- 4- to 10-membered heterocyclyl substituted by 0 to 3 groups independently selected from halo, such as F, Br, $C_1$ or I, $CF_3$, $OCF_3$, 5- or 6-membered heteroaryl, OH, hydroxy-$C_1$-$C_4$-alkyl, such as $HOCH_2CH_2$—, $C_1$-$C_4$ alkyl, such as $CH_3$, $C_1$-$C_4$ alkoxy, such as $CH_3O$, or di-$C_1$-$C_4$-alkylamino, such as $(CH_3)_2N$,
- $C_3$-$C_6$ cycloalkyl substituted by 0 to 3 groups independently selected from halo, such as F, Br, $C_1$ or I, $CF_3$, $OCF_3$, 5- or 6-membered heteroaryl, OH, hydroxy-$C_1$-$C_3$-alkyl, $C_1$-$C_4$ alkyl, such as $CH_3$, $C_1$-$C_4$ alkoxy, such as $CH_3O$, or di-$C_1$-$C_4$-alkylamino, such as $(CH_3)_2N$; and $R^{6a}$ is H, halo, $OCF_3$ $OCHF_2$, $C_1$-$C_4$ alkyl, halo-$C_1$-$C_4$-alkyl substituted with 1 to 5 fluorines, $CF_3$, $CHF_2$, $C_1$-$C_4$ alkoxy, $C_1$-$C_4$ alkylthio, $C_3$-$C_6$ cycloalkoxy, OH, CN, $NO_2$, $NR^{11}R^{12}$, carboxy, $C_1$-$C_4$ alkoxycarbonyl, $C(=O)NR^{11}R^{12}$, $C_1$-$C_4$ alkylsulfonyl, $S(=O)_2NR^{11}R^{12}$, phenyloxy, phenylthio, phenyl-$C_1$-$C_4$-alkoxy, heteroaryl-$C_1$-$C_4$-alkoxy, phenyl-$C_1$-$C_4$-alkyl, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, or $C_1$-$C_4$-alkoxy-$C_1$-$C_4$-alkoxy-$C_1$-$C_4$-alkyl; and $R^7$ is H, F, $C_1$ or $CH_3$.

Examples of the 5-membered heteroaryl ring

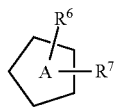

present in the compounds of Formula I include, but are not limited to,

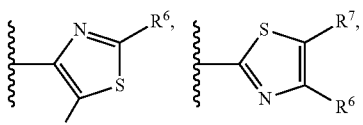

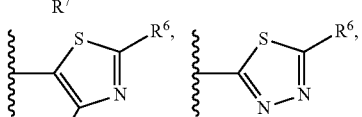

and

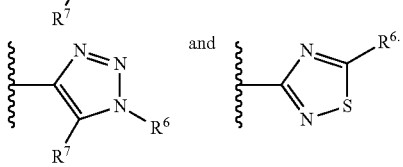

Examples of R⁶ groups present in the compounds of Formula I include, but are not limited to:

substituted phenyl, such as

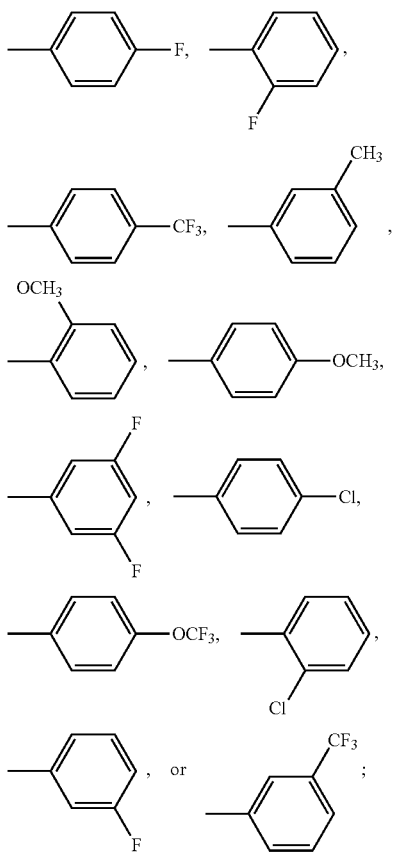

heterocyclyl, such as

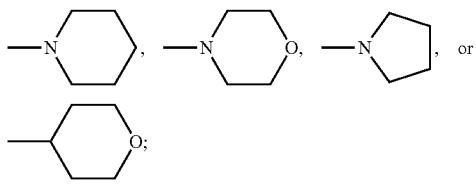

substituted heterocyclyl, such as

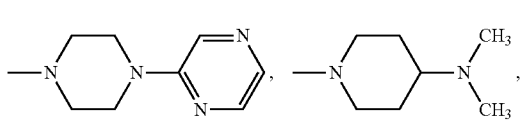

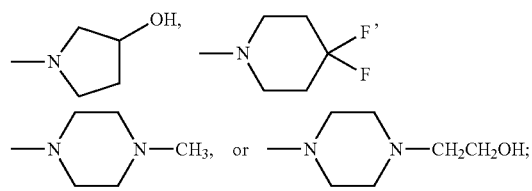

cycloalkyl, such as

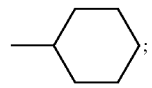

heteroaryl, such as

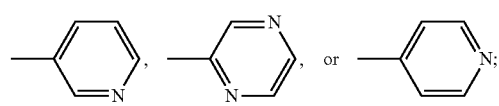

substituted heteroaryl, such as

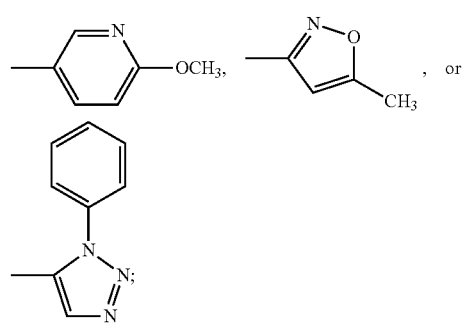

heteroaryl-$C_1$-$C_4$-alkyl, such as

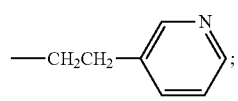

haloalkyl, such as $CF_3$, halo, such as Br, $C_1$-$C_4$-alkoxy-$C_1$-$C_4$-alkyloxy-$C_1$-$C_4$-alkyl, such as $CH_3OCH_2CH_2OCH_2$—, $C_1$-$C_4$ alkyl, such as —$CH_2CH_3$ or $CH_3$, aryl-$C_1$-$C_4$-alkyl, such as

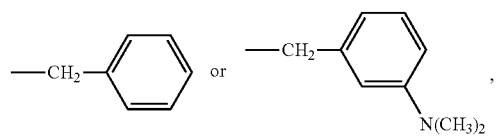

or
H;
—NR$^{11}$R$^{12}$, such as

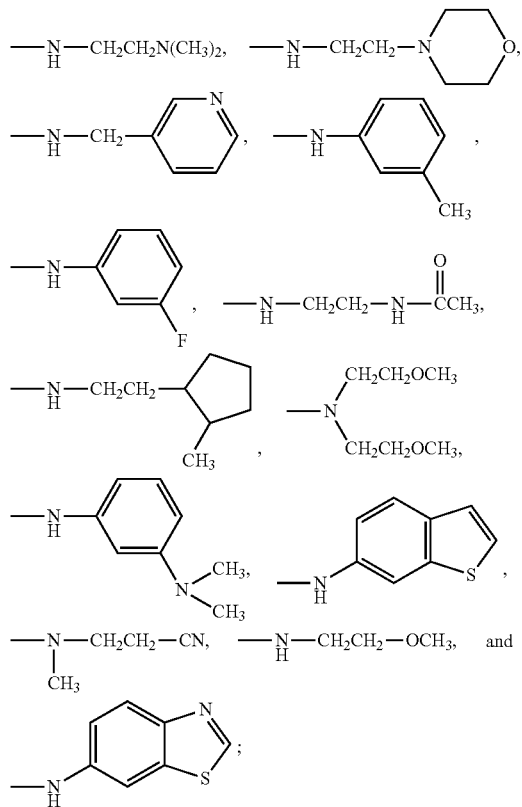

and
R$^7$ is selected from H and C$_1$-C$_4$ alkyl, such as CH$_3$.
Examples of R$^0$ groups suitable for use in the compounds of Formula I include, but are not limited to:
H;
C$_1$-C$_4$ alkyl, such as CH$_3$;
C$_1$-C$_4$ alkylthio, such as CH$_3$S;
C$_1$-C$_4$ alkoxy, such as CH$_3$O; and
halo-C$_1$-C$_4$-alkyl, such as F(CH$_3$)CH—, F$_2$(CH$_3$)C—, or CF$_3$.
Examples of R$^3$ groups suitable for use in the compounds of Formula I include, but are not limited to:
C$_1$-C$_4$ alkoxy, such as CH$_3$O;
H; and
halo, such as Cl.
R$^2$ is preferably H.
Y is preferably S or —CH=CH—.
In some embodiments, the present invention includes compounds of Formula I wherein:
Y is S or —CH=CH—;
X$^1$ is CH;
X$^2$ is CH;
X$^3$ is CR$^3$;
X$^4$ is CH;
R$^3$ is CH$_3$O, F or Cl;
R$^2$ is H; and
R$^4$ and R$^5$ are each H.

In some embodiments, the present invention includes compounds of Formula I wherein:
Y is S or —CH=CH—;
X$^1$ is CH;
X$^2$ is CH;
X$^3$ is CR$^3$;
X$^4$ is CH;
R$^4$ and R$^5$ are each H;
R$^0$ is R$^1$ and R$^{1a}$;
R$^1$ and R$^{1a}$ are independently selected from CH$_3$O, CH$_3$S, CH$_3$, or halo-C$_1$-C$_2$-alkyl, such as F(CH$_3$)CH— or F$_2$(CH$_3$)C—;
R$^2$ is H; and
R$^3$ is CH$_3$O, F, or Cl.
In some embodiments, the present invention includes compounds of Formula I wherein:
R$^0$ is R$^1$ and R$^{1a}$;
R$^1$ and R$^{1a}$ are independently selected from CH$_3$O, CH$_3$S, CH$_3$, or halo-C$_1$-C$_2$-alkyl, such as F(CH$_3$)CH—;
R$^2$ is H;
R$_3$ is CH$_3$O, F, or Cl; and

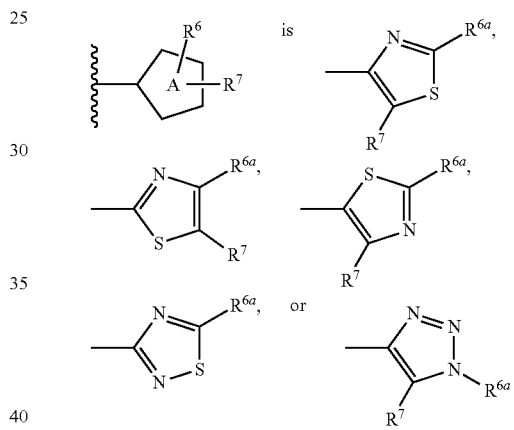

where R$^{6a}$ is defined as hereinbefore and can be:
H,
halo-C$_1$-C$_4$-alkyl substituted with 1 to 5 fluorines, such as CF$_3$ or CHF$_2$,
halo, such as Br,
OCF$_3$,
OCHF$_2$,
heteroaryl-C$_1$-C$_3$-alkyl, such as

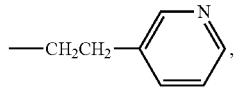

C$_3$-C$_6$ cycloalkoxy,
OH,
CN,
NO$_2$,
S(=O)$_2$NR$^{11}$R$^{12}$,
NR$^{11}$R$^{12}$,
COOH,
C$_1$-C$_4$ alkoxycarbonyl,
C(=O)NR$^{11}$R$^{12}$, $C_1$-$C_4$ alkylsulfonyl,
di-$C_1$-$C_4$-alkylaminophenyl-$C_1$-$C_4$-alkyl, such as

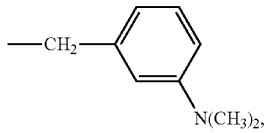

(di-$C_1$-$C_4$-alkoxy-$C_1$-$C_4$-alkyl)$C_1$-$C_4$-alkyl, such as

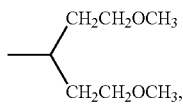

$C_1$-$C_4$-alkoxy-$C_1$-$C_4$-alkyloxy-$C_1$-$C_4$-alkyl, such as $CH_3OCH_2CH_2OCH_2$—,
$C_1$-$C_4$ alkyl, such as $CH_3$ or $C_2H_5$,
$C_1$-$C_4$ alkoxy, such as $CH_3O$,
aryl-$C_1$-$C_4$-alkyl, such as

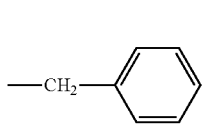 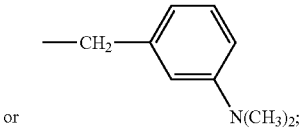

and
$R^7$ is H or $C_1$-$C_4$ alkyl, such as $CH_3$.

In some embodiments, the present invention includes compounds of Formula I wherein:

$R^0$ is $R^1$ or $R^{1a}$;
$R^1$ and $R^{1a}$ are independently selected from $CH_3O$, $CH_3S$, $CH_3$, or halo-$C_1$-$C_2$-alkyl, such as $F(CH_3)CH$—;
$R^2$ is H;
$R_3$ is $CH_3O$, F, or Cl;

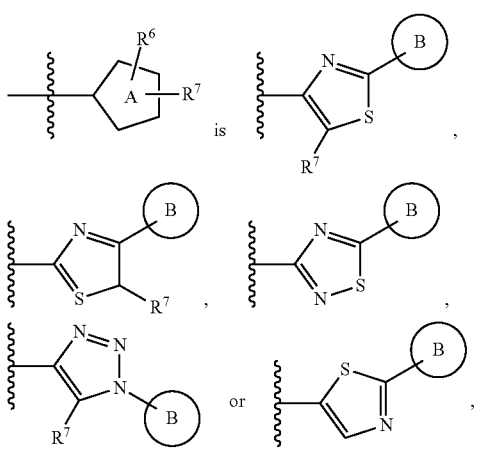

where

is:

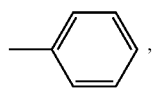

substituted phenyl, such as

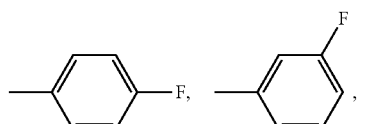

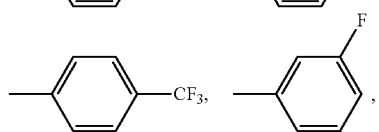

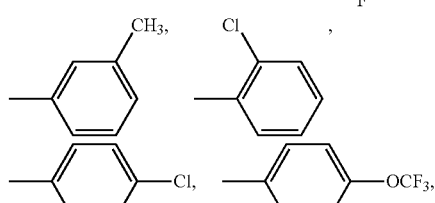

heteroaryl, such as

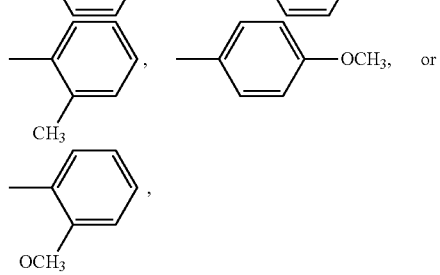

heterocyclyl, such as

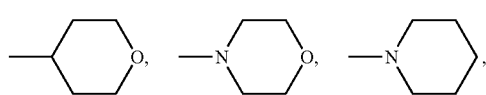

-continued

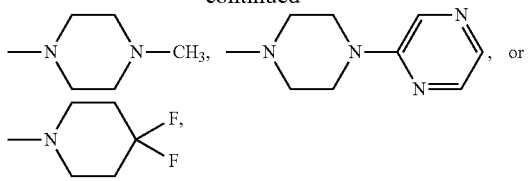

and
cycloalkyl, such as

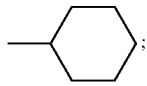

and
$R^7$ is H or $C_1$-$C_4$ alkyl, such as $CH_3$.

In some embodiments, the present invention includes compounds of Formula I wherein:
$Y$ is S;
$X^1$ is CH;
$X^2$ is CH;
$X^3$ is $CR^3$;
$X^4$ is CH;
$R^2$ is H;
$R^4$ and $R^5$ are each H;
$R^0$ is $R^1$;
$R^1$ is $CH_3O$ or $F(CH_3)CH$—;
$R^3$ is $CH_3O$;
$R^4$ and $R^5$ are each H;

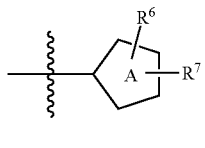 is 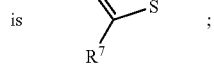;

$R^6$ is

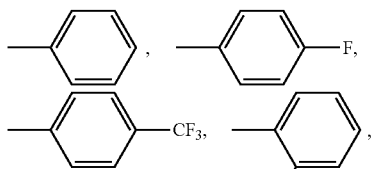

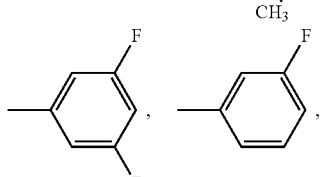

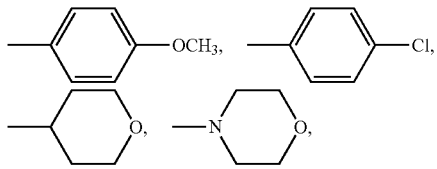

-continued

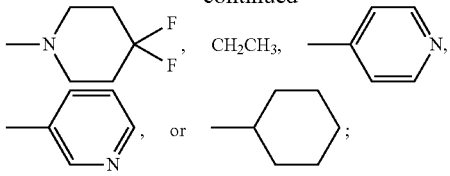

and
$R^7$ is H or $CH_3$.

In some embodiments, the present invention includes compounds of Formula I wherein:
$Y$ is CH=CH;
$X^1$ is CH;
$X^2$ is CH;
$X^3$ is $CR^3$;
$X^4$ is CH;
$R^2$ is H;
$R^4$ and $R^5$ are each H;
$R^0$ is $R^{1a}$;
$R^{1a}$ is $CH_3$;
$R^3$ is $CH_3O$;

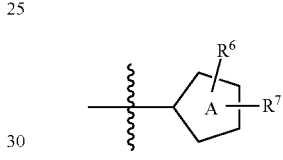

$R^6$ is

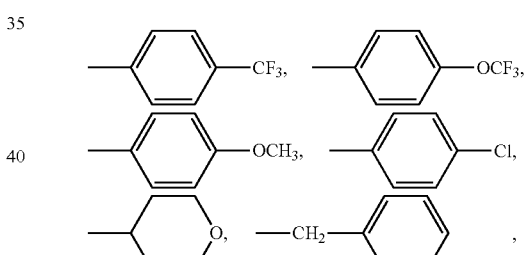

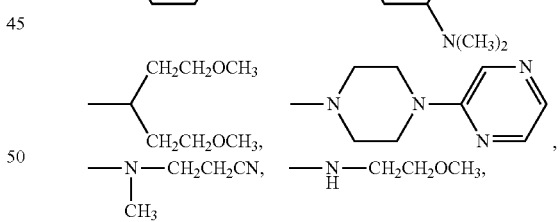

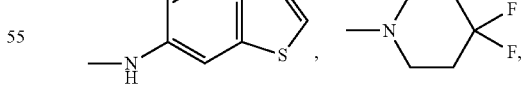

and $CH_2CH_3$; and
$R^7$ is H.

In some embodiments, the present invention includes compounds of Formula I, wherein:
$R^0$ is $C_1$-$C_4$ alkoxy, such as $CH_3O$, $C_1$-$C_4$ alkyl, such as methyl, ethyl, and isopropyl, or halo, such as Br or Cl;
$R^2$ is H;
$R^3$ is $C_1$-$C_4$ alkoxy, such as $CH_3O$, or halo, such as F or Cl;

$R^4$ is H; and $R^5$ is H.

In some embodiments, the present invention includes compounds of Formula I, wherein:

$X^1$ is CH;

$R^0$ is $C_1$-$C_2$ alkoxy, such as methoxy, or halo, such as F;

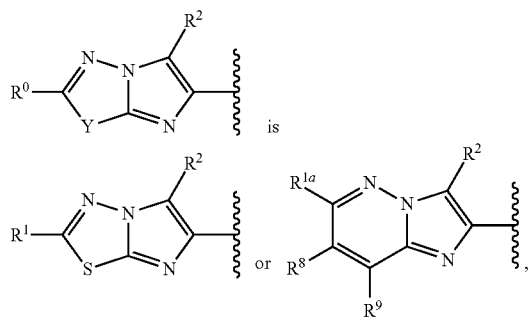 is where $R^1$ or $R^{1a}$ is independently selected from $C_1$-$C_4$ alkyl, such as $CH_3$, $C_2H_5$ or i-$C_3H_7$, or $C_1$-$C_3$ alkoxy, such as $CH_3O$;

$R^8$ and $R^9$ are each H; and $R^2$ is H.

In some embodiments, the present invention includes compounds of Formula I, wherein:

$X^1$ is CH or N;

$R^3$ is $OCH_3$ or halo, such as F; and $R^6$ is phenyl, and phenyl substituted with 0 to 3 substituents selected from 1 or 2 halo groups, such as F, halo-$C_1$-$C_2$ alkyl which contains 1 to 5 halogens, such as $CF_3$, $C_1$-$C_3$ alkyl, such as $CH_3$, and $C_1$-$C_3$ alkoxy, or $R^6$ is $C_1$-$C_3$ alkyl, such as $CH_3$, or halo-$C_1$-$C_2$-alkyl, such as $CF_3$.

In some embodiments, the present invention includes compounds of Formula I wherein

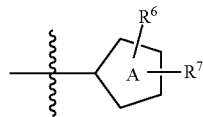

is a 5-membered heteroaryl ring containing one or two N atoms and one S atom or three N atoms.

In some embodiments, the present invention includes compounds of Formula I wherein:

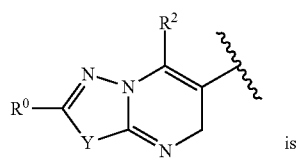 is

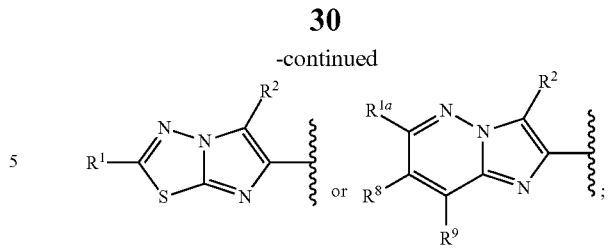

$X^1$ is CH;

$R^1$ is $CH_3O$, $CH_3$, $C_2H_5$ or i-$C_3H_7$;

$R^{1a}$ is $CH_3$;

$R^2$ is H;

$R^3$ is CHO or F;

$R^6$ is $CH_3$, $CF_3$, phenyl,

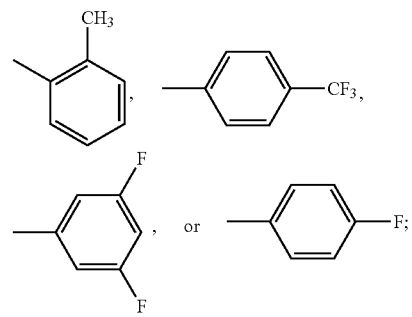

and $R^8$ and $R^9$ are each H.

In some embodiments, the present invention includes compounds of Formula I wherein:

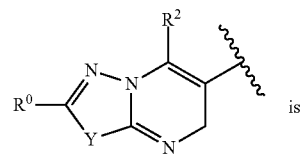 is

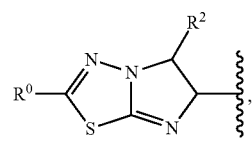, where $R^1$ is $C_1$-$C_3$ alkoxy, such as $CH_3O$, or $C_1$-$C_4$ alkyl, such as i-$C_3H_7$, $R^2$ is H, $X^1$ is CH, $R^3$ is $C_1$-$C_3$ alkoxy, such as $CH_3O$, or halo, such as F, and $R^6$ is $CF_3$, phenyl, phenyl substituted with 1 or 2 halogens, such as F or Cl, for example, p-F—$C_6H_4$, or 2,4-di-F—$C_6H_3$, or phenyl substituted with $CF_3$, such as p-$CF_3$—$C_6H_4$, or R[8] and R[9] are each H; and
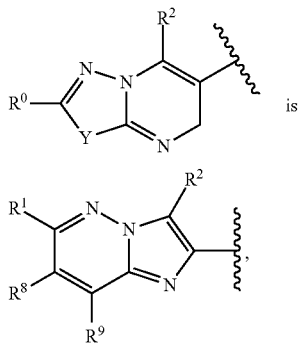
is
where
- R[1] is $C_1$-$C_3$ alkyl, such as $CH_3$,
- X[1] is CH,
- R[2] is H,
- R[3] is $C_1$-$C_3$ alkoxy, such as $CH_3O$,
- R[6] is phenyl substituted with $CF_3$, such as p-$CF_3$—$C_6H_4$, and
- R[8] and R[9] are each H.
In some embodiments, the present invention includes compounds of the invention having the structure:

33
-continued
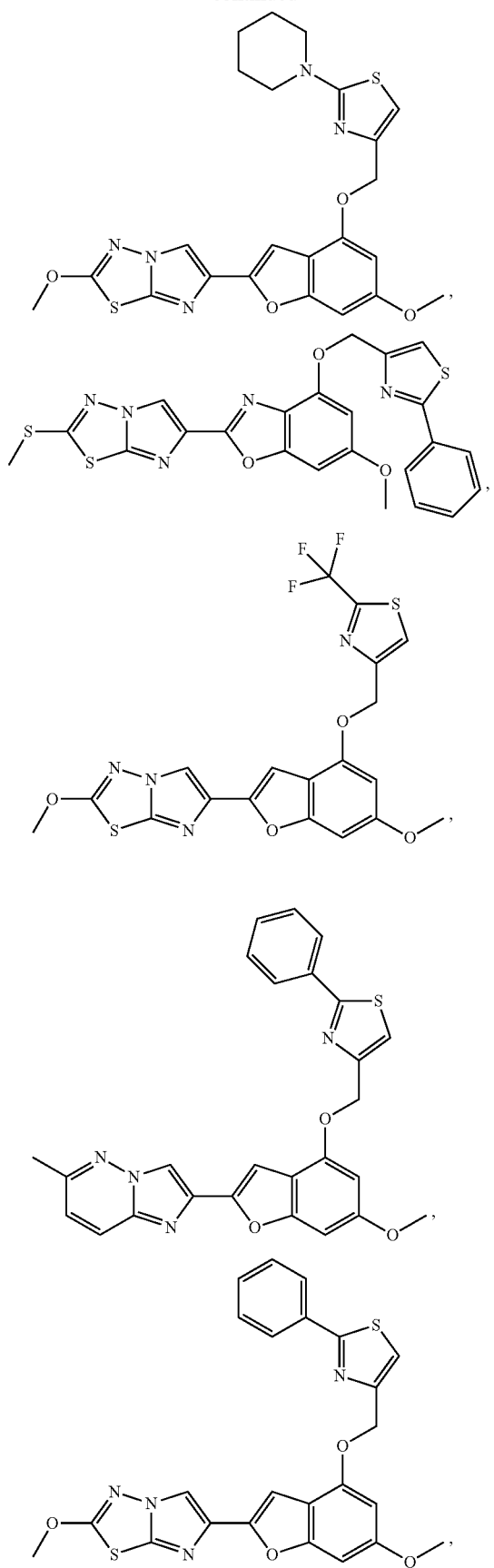
34
-continued
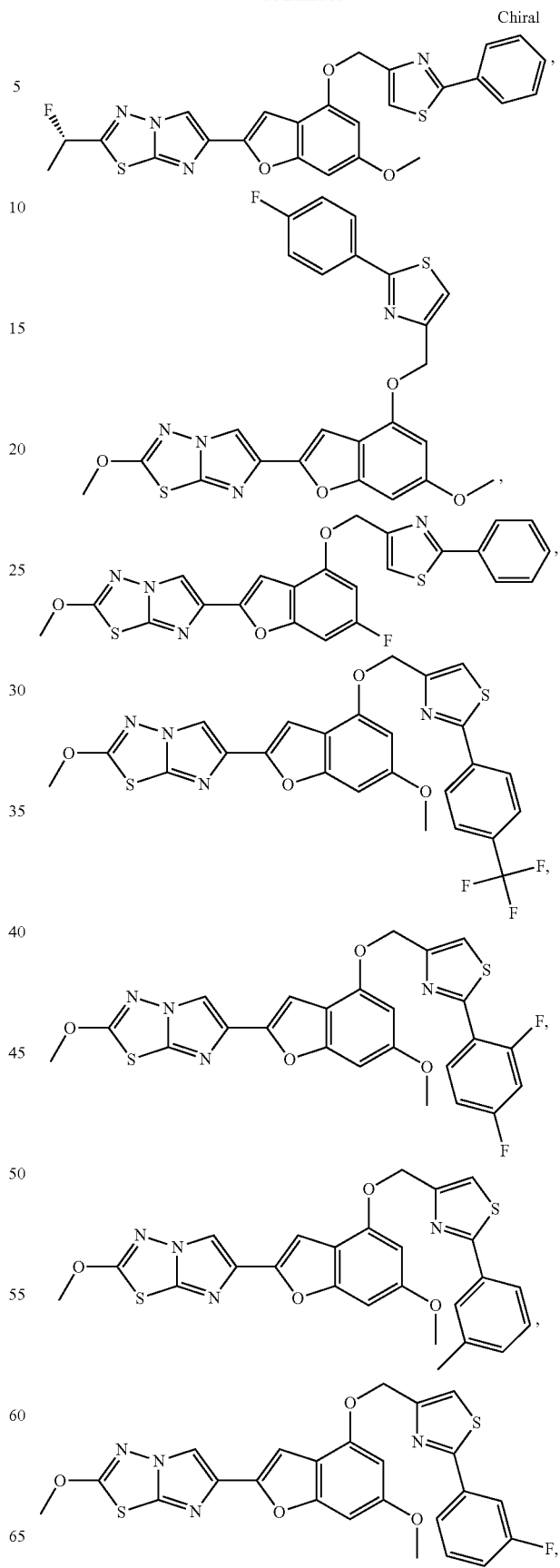

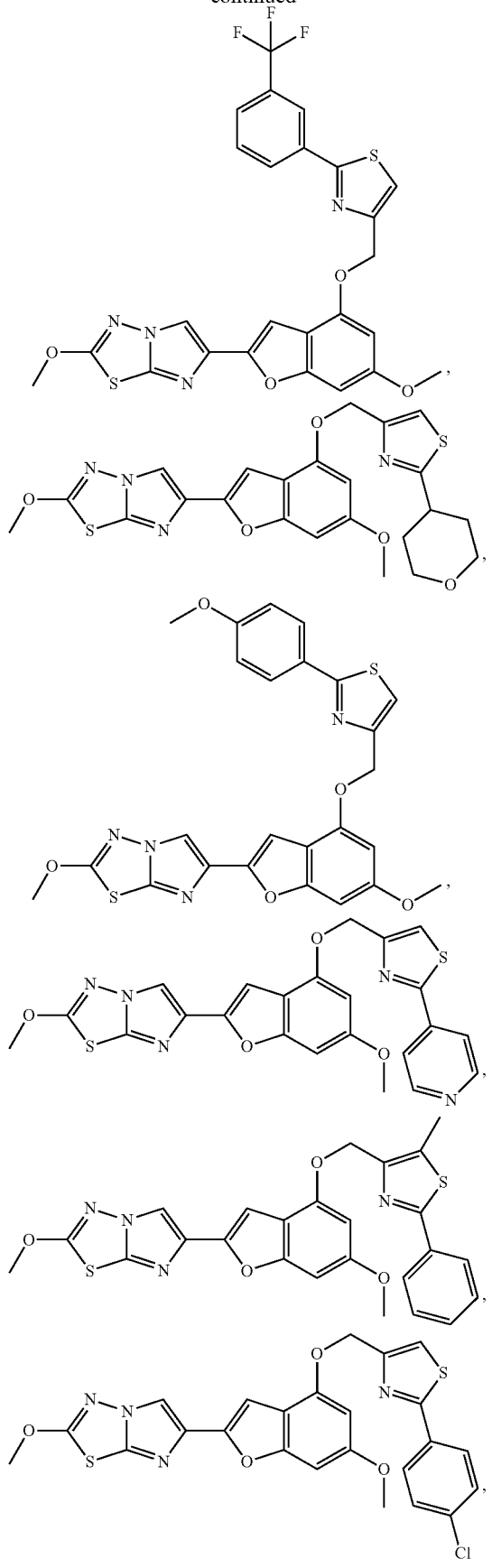
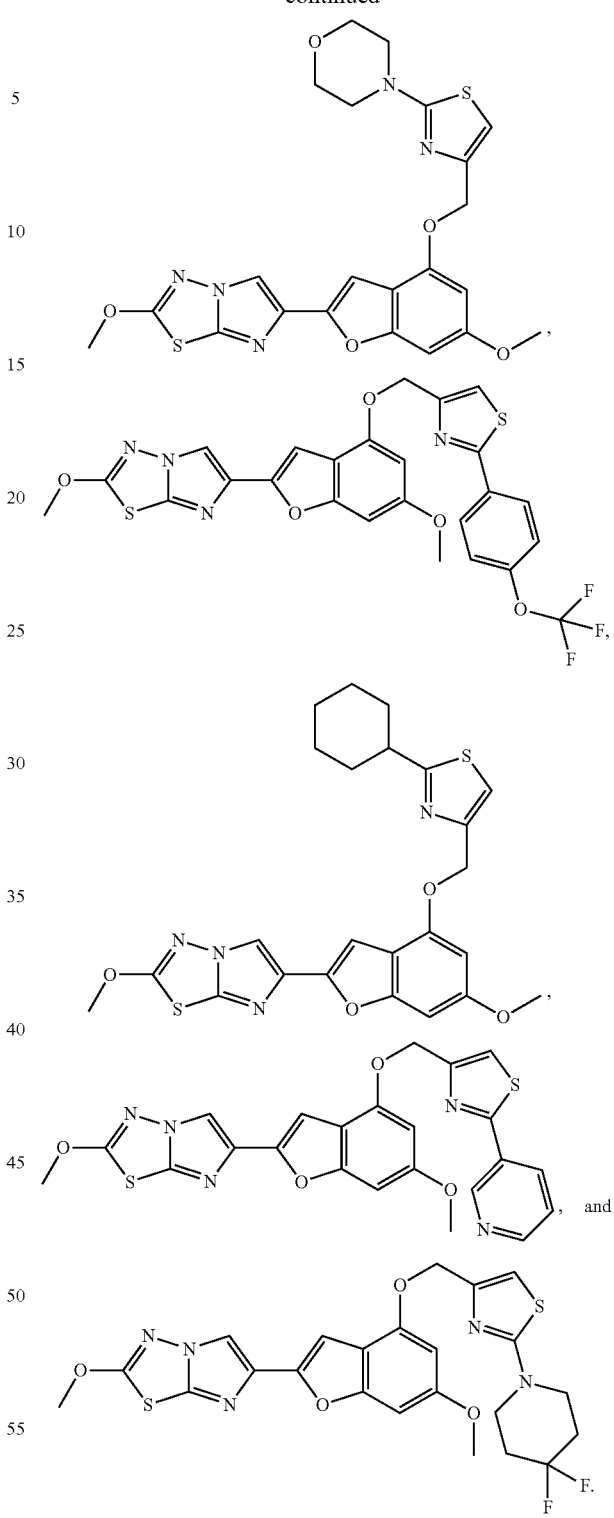
Preferably, PAR4 compounds of the invention have IC$_{50}$s in the FLIPR Assay (described hereinafter) of 5 μM or less, more preferably 500 nM or less, and even more preferably 10 nM or less. Examples of such preferred PAR4 compounds are those reported in the specific Working Examples herein. Activity data for a number of these compounds is presented in the Table of Example F.

In some embodiments, the present invention provides at least one compound of the present invention or a stereoisomer, tautomer, pharmaceutically acceptable salt, solvate, or prodrug ester thereof.

In some embodiments, the present invention provides a pharmaceutical composition, which includes a pharmaceutically acceptable carrier and a therapeutically effective amount of a compound of Formula I, or stereoisomers, tautomers, pharmaceutically acceptable salts, prodrug esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors or thrombin inhibitors. Preferably, the FXa inhibitors are apixaban or rivaroxaban. Preferably, the thrombin inhibitor is dabigatran.

In some embodiments, the present invention provides a method for the treatment or prophylaxis of a thromboembolic disorder which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug esters thereof.

In some embodiments, the present invention includes a method for the treatment of a thromboembolic disorder or the primary prophylaxis of a thromboembolic disorder, which includes the steps of administering to a patient (for example, a human) in need thereof a therapeutically effective amount of a compound of Formula I, or stereoisomers, tautomers, pharmaceutically acceptable salts, prodrug esters, or solvates thereof, wherein the thromboembolic disorder is selected from arterial cardiovascular thromboembolic disorders, venous cardiovascular thromboembolic disorders, thromboembolic disorders in the chambers of the heart or in the peripheral circulation, arterial cerebrovascular thromboembolic disorders and venous cerebrovascular thromboembolic disorders.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I of the invention.

Other Embodiments Of The Invention

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials.

All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), $-NR_aR_b$, $-N(alkyl)_3^+$, $-NR_aSO_2$, $-NR_aSO_2R_c$, $-SO_2R_c-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_1$-$C_4$ alkylene)N-$R_aR_b$, $-C(=O)NR_a(SO_2)R_b$, $-CO_2(C_1$-$C_4$ alkylene) $NR_aR_b$, $-NR_aC(=O)R_b$, $-NR_aCO_2R_b$, $-NR_a(C_1$-$C_4$ alkylene)$CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of ($C_1$-$C_6$)alkyl, ($C_2$-$C_6$)alkenyl, hydroxy, halogen, cyano, nitro, $CF_3$, $O(C_1$-$C_6$ alkyl), $OCF_3$, $C(=O)H$, $C(=O)(C_1$-$C_6$ alkyl), $CO_2H$, $CO_2(C_1$-$C_6$ alkyl), $NHCO_2(C_1$-$C_6$ alkyl), $-S(C_1$-$C_6$ alkyl), $-NH_2$, $NH(C_1$-$C_6$ alkyl), $N(C_1$-$C_6$ alkyl)$_2$, $N(CH_3)_3^+$, $SO_2(C_1$-$C_6$ alkyl), $C(=O)(C_1$-$C_4$ alkylene)$NH_2$, $C(=O)(C_1$-$C_4$ alkylene)NH(alkyl), $C(=O)(C_1$-$C_4$ alkylene)$N(C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

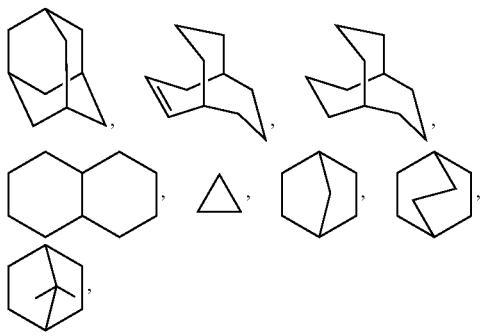

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$-10 aryl" refers to phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle", "heterocyclo" or "heterocyclic" group is intended to mean a stable 5-, 6-, or 7-membered monocyclic or bicyclic or 7-, 8-, 9-, 10-, 11-, 12-, 13-, or 14-membered bicyclic heterocyclic ring that is saturated or partially unsaturated, and that contains carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, $C(=O)CH_3$, $SCH_3$, $S(=O)CH_3$, $S(=O)_2CH_3$, $C_1$-$C_3$ alkyl, $CO_2H$ and $CO_2CH_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

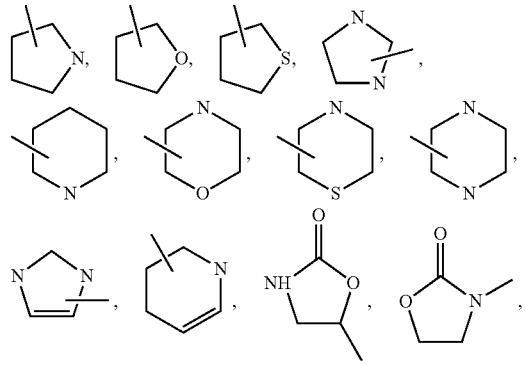

and

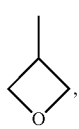

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, =O, C(=O)$CH_3$, $SCH_3$, S(=O)$CH_3$, S(=O)$_2CH_3$, $C_1$-$C_3$ alkyl, $CO_2H$ and $CO_2CH_3$. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2). Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Preferred heteroaryl groups include

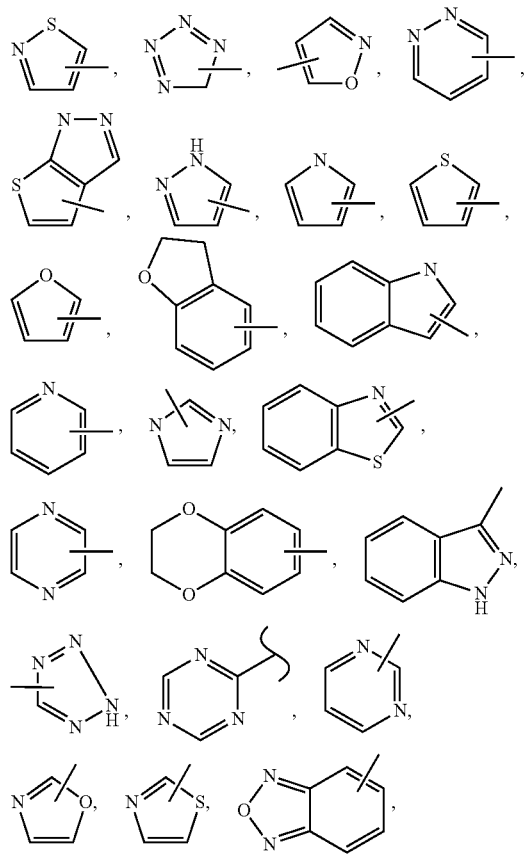

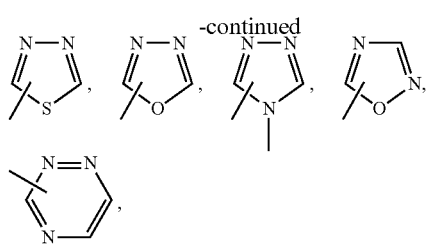

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group C(=O)$R_e$, as well as the bivalent groups —C(=O)— or —C(=O)$R_e$—, which are linked to organic radicals. The group Re can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation "〜" or

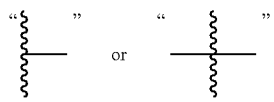

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug ester forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) King, F. D., ed., Medicinal Chemistry: Principles and Practice, The Royal Society of Chemistry, Cambridge, UK (1994).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "¹H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| $Et_2O$ | diethyl ether |
| i-PrOH or IPA | isopropanol |
| HOAc | acetic acid |
| BOP reagent | benzotriazol-1-yloxytris(dimethyl-amino)phosphonium hexafluorophosphate |
| $BBr_3$ | boron tribromide |
| Boc | tert-butyloxycarbonyl |
| cDNA | complimentary DNA |
| $CDCl_3$ | deuterated chloroform |
| $CH_2Cl_2$ | dichloromethane |
| $CH_3CN$ | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC•HCl) or EDCI (or EDCI•HCl) or EDAC | 3-ethyl-3'-(dimethylamino)propyl-carbodiimide hydrochloride or 1-(3-dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperaxine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidinophosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| $K_3PO_4$ | potassium phosphate |
| $MgSO_4$ | magnesium sulfate |
| NaCl | sodium chloride |
| NaH | sodium hydride |
| $NaHCO_3$ | sodium bicarbonate |
| NaOH | sodium hydroxide |
| $Na_2SO_3$ | sodium sulfite |
| $Na_2SO_4$ | sodium sulfate |
| $NH_3$ | ammonia |
| $NH_4Cl$ | ammonium chloride |
| $NH_4OH$ | ammonium hydroxide |
| OTs | tosylate, para-toluenesulfonate |
| $PBr_3$ | phosphorous tribromide |
| $Pd(PPh_3)_4$ | tetrakis(triphenylphosphine)palladium (0) |
| (S,S)-EtDuPhosRh(I) | (+)-1,2-bis((2S,5S)-2,5-diethylphospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

Compounds of formula I of this invention can be obtained by condensation of an amine of formula III with a ketone of formula IV which contains a leaving group Z such as a bromide, iodide or tosylate and a protecting group PG such as benzyl as shown in Scheme 1. Both compounds of formula III and IV are commercially available or can be prepared by means known to one skilled in the art. This condensation is promoted by heating, either thermally or preferably by microwave irradiation. The protecting group can be removed by methods known in the art, such as $BCl_3$ at −78° C. in the presence of pentamethylbenzene. Subsequent alkylation using either an alcohol VI under Mitsunobu conditions or a bromide VII in the presence of base such as potassium carbonate provides the compounds of Formula I. Alcohols and bromides VI and VII are commercially available or can be prepared by methods known in the art.

Scheme 1

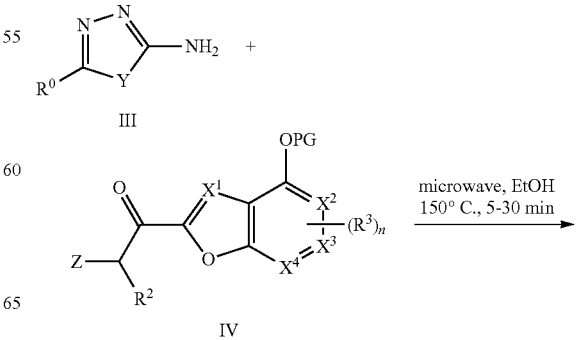

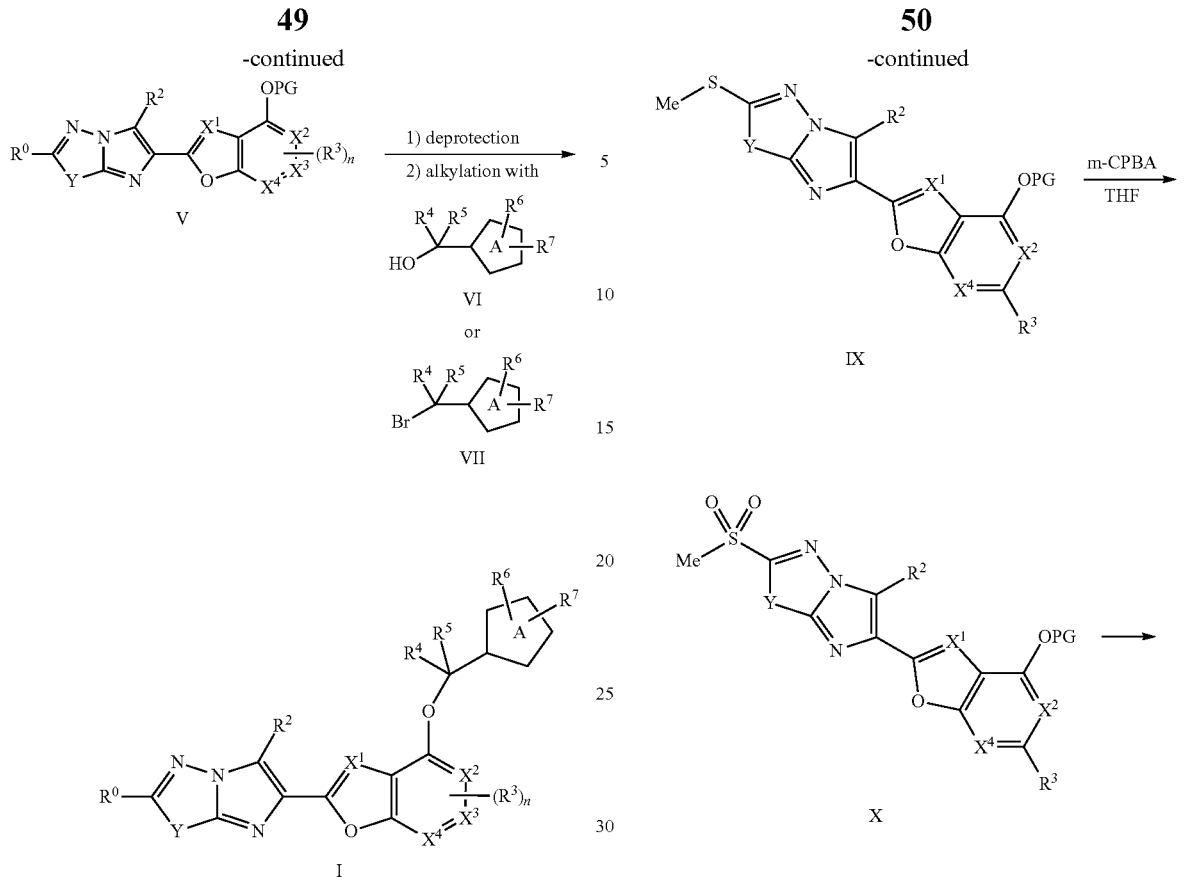

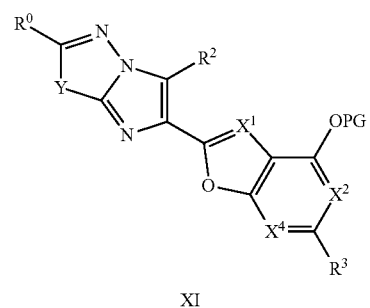

Alternatively, compounds of Formula I can be prepared from compounds of formula IX upon activation of the thiomethyl group by oxidation to a sulfone VII as shown in Scheme 2. This allows introduction of a variety of nucleophiles as groups $R^0$ such as alcohols, thiols and amines in the presence of a base such as potassium carbonate or sodium hydride either neat or in a polar, aprotic solvent such as dimethylformamide to give compounds XI. Compounds XI can be converted to compounds of Formula I by removal of the protecting group (PG) and alkylation as discussed in Scheme 1.

Scheme 2

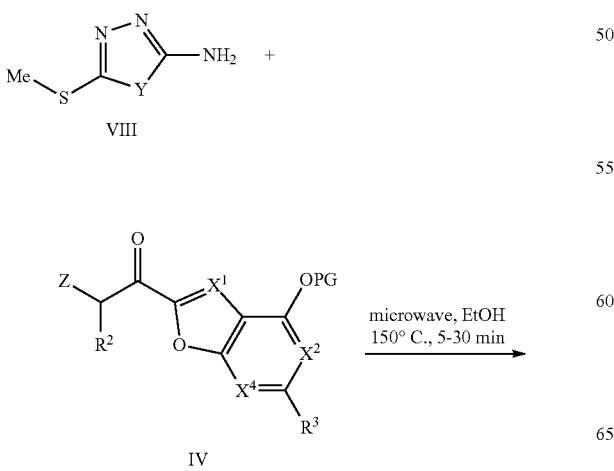

Substituted benzofurans bearing α-bromoketone substituents at the 2-position (XV) can be prepared as shown in Scheme 3. o-Hydroxy benzaldehydes XII can be prepared by methods known to one skilled in the art of organic synthesis, and can be condensed with ketones of formula XIII bearing a leaving group Q such as chloro, bromo or tosyloxy, to give benzofurans XIV. Bromination of compounds of formula XIV affords bromoketones XV, which can be condensed with a substituted aminoheterocycle III according to Scheme 1 to give compounds of Formula I. Bromoketones XV are a specific subset of compounds IV in Scheme 1.

Scheme 3

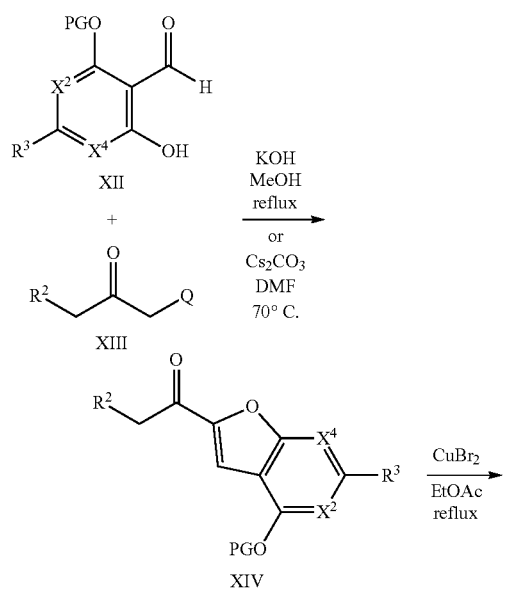

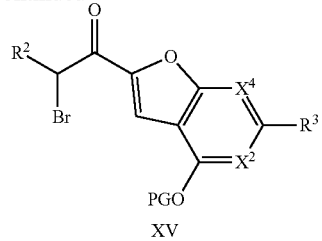

Benzoxazole compounds of Formula I can be prepared starting from substituted aminoheterocycle III and pyruvate esters of formula XVI which contain a leaving group Z such as a bromide, iodide or tosylate as shown in Scheme 4. Both compounds of formula III and XVI are commercially available or are available by means known to one skilled in the art. Following condensation and saponification of the ester to form acid XVIII, amino phenols of formula XIX are coupled to form amides of the formula XX, which can be cyclized under acid catalysis to form benzoxazole compounds of formula XXI. These can be deprotected and alkylated as shown in Scheme 1 to provide compounds of Formula I.

Scheme 4

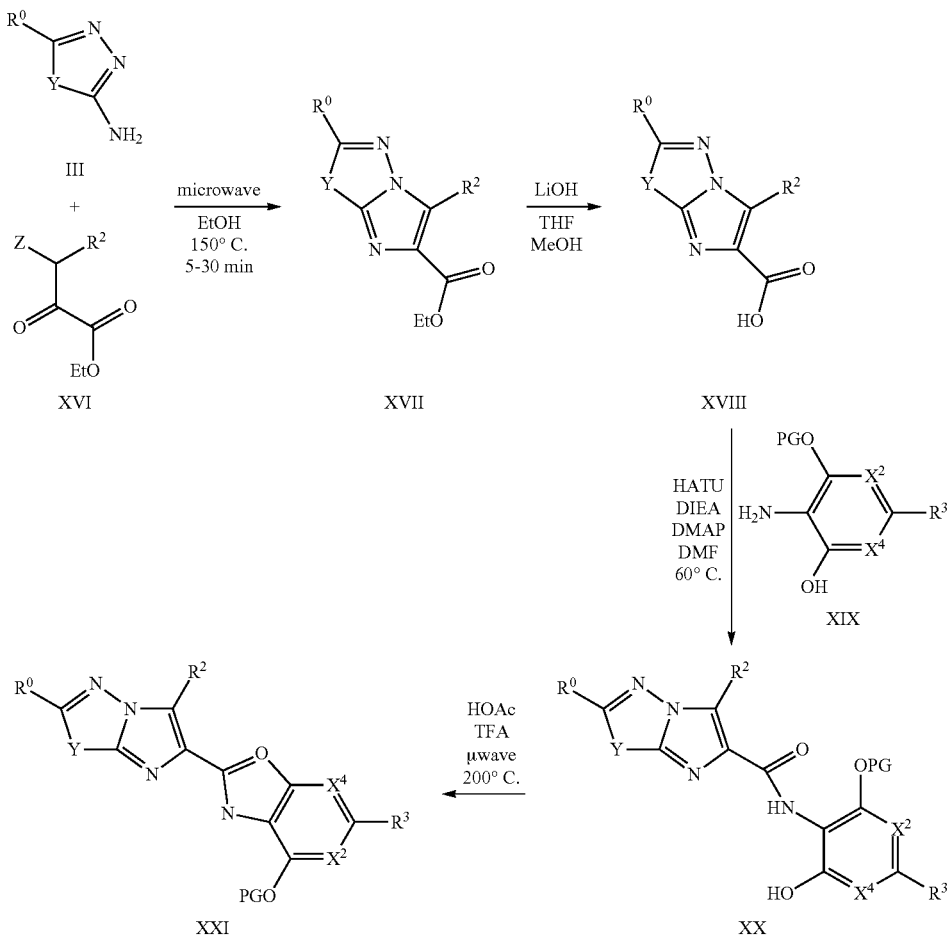

Aminoheterocycles XXIV can be prepared from carbon disulfide (XXII) via the thioxanthate intermediate XXIII These aminoheterocycles are useful for the preparation of compounds of Formula I.

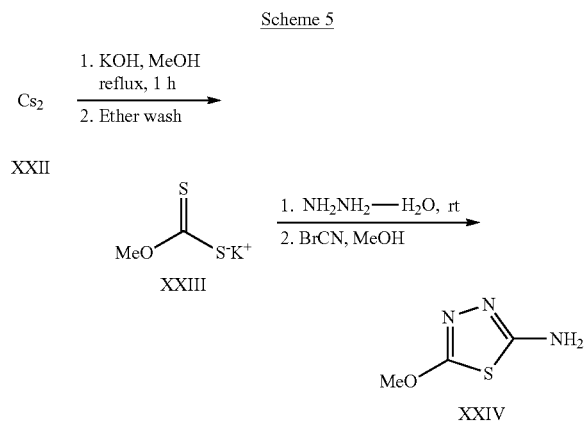

Aminoheterocycles XXX, which are useful intermediates for preparation of compounds of Formula I where Y=—CH$_2$CH$_2$—, can be prepared from ketoesters XXV. Cyclization with hydrazine, followed by oxidation with bromine gives pyridazinones XXVII. Chlorination, displacement with hydrazine, and subsequent hydrogenation provides aminoheterocycles XXX, which are a specific subset of compounds III in Scheme I. As such, these aminoheterocycles are useful for the preparation of compounds of Formula I.

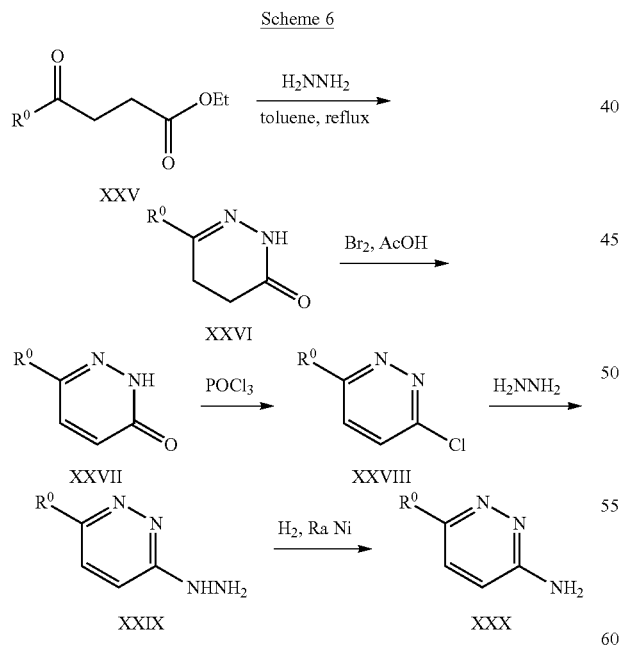

EXAMPLES

The following compounds of the invention have been prepared, isolated and characterized using the methods disclosed herein. They demonstrate a partial scope of the invention and are not meant to be limiting of the scope of the invention. In the experimental procedures, solution ratios express a volume relationship, unless stated otherwise. NMR chemical shifts (δ) are reported in parts per million (ppm). Products were analyzed by reverse phase analytical HPLC using the following methods:

Method A: Column: ZORBAX® XDB-C18 3.5 micron, 4.6×30 mm; Mobile Phase: A=MeOH:H$_2$O:TFA (95:5:05), B=MeOH:H$_2$O:TFA (5:95:05). Grad.: T=0: 100% solv A; T=2:100% solv B; stop time: 4 min. Flow=3.0 mL/min Method B: Column: Agilent POROSHELL® 120; EC-C18, 2.7 um; 2.1×30 mm; Mobile Phase: Solv A: 5% MeOH: 95% H$_2$O+0.1% AcOH; Solv B: 95% MeOH: 5% H$_2$O+0.1% AcOH; Grad.: T=0: 100% solv A; T=1:100% solv B; stop time: 4 min. Flow=1.0 mL/min Method C: SunfireC18 3.5 micron column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm)

Method D: Eclipse XDB-C18 3.5 micron column (4.6×30 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm)

Method E: Eclipse XDB-C18 3.5 micron column (4.6×30 mm) eluted at 3 mL/min with a 2 min gradient from 100% A to 100% B (A: 5% acetonitrile, 94.95% water, 0.05% TFA; B: 5% water, 94.95% acetonitrile, 0.05% TFA, UV 220 nm)

Method F: ZORBAX® SB-Phenyl 3.5 micron column (4.6×50 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm)

Example 1

2-Methoxy-6-(6-methoxy-4-((2-methylthiazol-4-yl)methoxy)benzofuran-2-yl)imidazo[2,1-b][1,3,4]thiadiazole

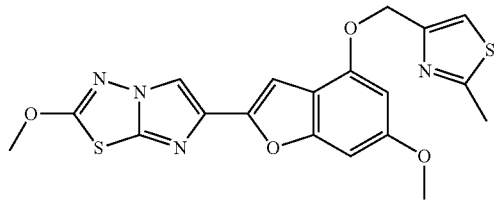 [SMILES: COc1cc(OCc2csc(C)n2)c2cc(-c3cn4nc(OC)sc4n3)oc2c1]

1A. (2-Methylthiazol-4-yl)methanol

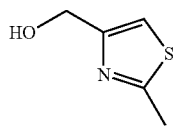

A solution of 2-methyl-thiazole-4-carboxylic acid ethyl ester (1.26 g, 7.36 mmol) in ethyl ether (10 mL) was cooled to −78° C. and treated with a solution of LAH (0.83 g, 21.9 mmol) in dry THF (30 mL) added dropwise over 10 min. After 3 hours, at −78° C., the mixture was quenched with sat.

Na$_2$SO$_4$ (app. 20 mL). The mixture was allowed to warm up to 22° C. and was extracted with ethyl ether (4×50 mL). The combined extracts were washed with brine, dried over anhydrous MgSO$_4$ and concentrated to give an oil. Filtration on a silica gel pad (3×7 cm) and elution with ethyl acetate gave an oil which was distilled to afford the title material (0.664 g, 70%) as an oil which crystallized. B.p. 60-70° C./0.2 torr. HRMS (ESI) calcd for C$_5$H$_8$NOS [M+H]$^+$ m/z 130.0321. found 130.0342. $^1$H NMR (CDCl$_3$, 600 MHz) δ 6.99 (d, J=0.8 Hz, 1H), 4.70 (s, 1H), 2.98 (br s, 1H), 2.68 (s, 3H).

1B. 5-(Benzyloxy)-7-methoxy-2,2-dimethyl-4H-benzo[d][1,3]dioxin-4-one

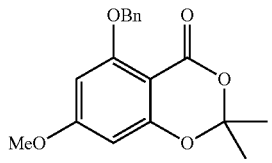 [SMILES: COc1cc(OCc2ccccc2)c2c(c1)OC(C)(C)OC2=O]

A solution of 5-hydroxy-7-methoxy-2,2-dimethyl-4H-benzo[d][1,3]dioxin-4-one (30.00 g, 0.134 mol) in N,N-dimethylformamide (400 mL) was treated with powdered anhydrous potassium carbonate (19.41 g, 0.14 mol) added all at once. The resulting mixture was stirred in vacuo for 10 min. and then flushed with nitrogen. The reaction flask was placed in a water bath (22° C.) and treated with benzyl bromide (24.03 g, 0.14 mol) added dropwise over 15 min. The resulting mixture was then stirred at 22° C. for 18 h (no starting material left by tlc). The solid was filtered and washed with N,N-dimethylformamide. The filtrate was evaporated in vacuo and the residual oil was diluted with ethyl acetate (500 mL), washed with cold 0.1 N hydrochloric acid, saturated sodium bicarbonate and brine. After drying over anhydrous magnesium sulfate, evaporation of the solvent gave a thick syrup. Crystallization form ethyl acetate (50 mL) and hexane (150 mL) gave 35.17 g of 5-(benzyloxy)-7-methoxy-2,2-dimethyl-4H-benzo[d][1,3]dioxin-4-one as large colorless prisms. Chromatography of the mother liquors on silica gel (4×13 cm, elution toluene—ethyl acetate 0-5%) gave 6.64 g of additional material to afford a total yield of 41.81 g (99%). HRMS (ESI) calcd for C$_{18}$H$_{19}$O$_5$ [M+H]$^+$ m/z 315.1227. found 315.1386. $^1$H NMR (CDCl$_3$, 600 MHz) δ 1.68 (s, 6H), 3.77 (s, 3H), 5.19 (s, 2H), 5.19 (s, 2H), 6.04 (d, J=2.03 Hz, 1H), 6.15 (d, J=2.03 Hz, 1H), 7.27 (broad t, 1H), 7.36 (broad t, 2H), 7.52 (broad d, 2H).

1C.
2-(Benzyloxy)-6-hydroxy-4-methoxybenzaldehyde

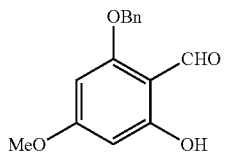

A solution of 5-(benzyloxy)-7-methoxy-2,2-dimethyl-4H-benzo[d][1,3]dioxin-4-one (Example 1B, 6.76 g, 21.5 mmol) in dichloromethane (120 mL) was cooled to −78° C. and treated with 43 mL (64.5 mmol) of a 1.5 M solution of diisobutylaluminum hydride in toluene added dropwise over 20 min. The resulting mixture was then stirred at −78° C. for 3 h. The reaction mixture was quenched by the careful addition of methanol (5 mL) added dropwise over 15 min, followed by 1N hydrochloric acid (50 mL) added dropwise over 15 min. The cooling bath was then removed and an additional 150 mL of 1N hydrochloric acid was added over 20 min. The mixture was then stirred at 22° C. for 2 h and diluted with dichloromethane (400 mL). The organic phase was collected and the aqueous phase (pH~1) was extracted with dichloromethane (3×50 mL). The combined organic extracts were washed with brine, dried over anhydrous magnesium sulfate and concentrated in vacuo. The residual oil was diluted with tetrahydrofuran (70 mL), treated with 10 mL of 0.1N hydrochloric acid and stirred at 20° C. for 2 h. The reaction mixture was diluted with ethyl acetate (300 mL), washed with brine, dried over anhydrous magnesium sulfate, evaporated in vacuo to give a clear oil. Chromatography on silica gel (4×13 cm, elution toluene) gave 4.08 g (73% yield) of the title aldehyde as a clear oil which solidified on standing. LC (Method C): 2.237 min. HRMS (ESI) calcd for C$_{15}$H$_{15}$O$_4$ [M+H]$^+$ m/z 259.0965. found 259.1153. $^1$H NMR (CDCl$_3$, 600 MHz) δ 3.80 (s, 3H), 5.07 (s, 2H), 5.97 (d, J=2.1 Hz, 1H), 6.01 (d, J=2.1 Hz, 1H), 7.3-7.4 (m, 5H), 10.15 (s, 1H), 12.49 (s, 1H).

1D.
1-(4-(Benzyloxy)-6-methoxybenzofuran-2-yl)ethanone

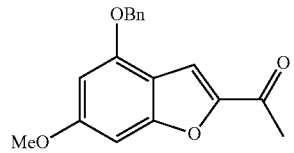 [SMILES: COc1cc(OCc2ccccc2)c2cc(C(C)=O)oc2c1]

A solution of 2-(benzyloxy)-6-hydroxy-4-methoxybenzaldehyde (Example 1C, 3.46 g, 13.4 mmol) in N,N-dimethylformamide (50 mL) was treated with powdered anhydrous cesium carbonate (4.58 g, 14.05 mmol) added all at once. The resulting mixture was stirred in vacuo for 10 min. and then flushed with nitrogen. The reaction flask was placed in a water bath (22° C.) and treated with chloroacetone (1.74 g, 18.7 mmol) added dropwise over 5 min. The resulting mixture was then stirred at 22° C. for 18 h (no starting aldehyde left by tlc and formation of the intermediate alkylated aldehyde). The solid was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. This syrup was diluted with tetrahydrofuran (50 mL) and ethyl acetate (50 mL), treated p-toluenesulfonic acid monohydrate (0.2 g) and stirred at 20° C. for 1 h (tlc indicated complete cyclization of the intermediate alkylated aldehyde to the benzofuran). The reaction mixture was diluted with ethyl acetate (300 mL), washed with saturated sodium bicarbonate and brine. After drying over anhydrous magnesium sulfate, evaporation of the solvent gave a thick syrup. Chromatography on silica gel (4×12 cm, elution toluene-ethyl acetate 2-4%) gave 3.51 g (88% yield) of the title benzofuran as a yellow solid. Recrystallization from ethyl acetate (10 mL) and hexane (20 mL) gave the title material as large yellow prisms (3.15 g). LC (Method D): 2.148 min. HRMS (ESI) calcd for $C_{18}H_{17}O_4$ [M+H]$^+$ m/z 297.1121. found 297.1092. $^1$H NMR (CDCl$_3$, 600 MHz) δ 2.51 (s, 3H), 3.82 (s, 3H), 5.13 (s, 2H), 6.37 (d, J=1.77 Hz, 1H), 6.63 (broad s, 1H), 7.34 (broad t, 1H), 7.39 (broad t, 2H), 7.44 (broad d, 2H), 7.55 (d, J=0.7 Hz, 1H).

1E. 1-(4-(Benzyloxy)-6-methoxybenzofuran-2-yl)-2-bromoethanone

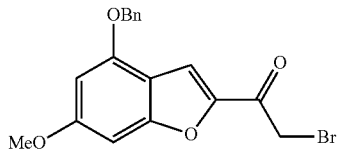 [SMILES: COc1cc(OCc2ccccc2)c2cc(C(=O)CBr)oc2c1]

A 250-mL, three-necked flask is equipped with a magnetic stirring bar and purged with a nitrogen atmosphere was charged with anhydrous tetrahydrofuran (25 mL) followed by 9.3 mL (9.3 mmol) of a 1M solution of lithium bis(trimethylsilyl)amide in tetrahydrofuran. The mixture was cooled to −78° C. and treated with a solution of 1-(4-(benzyloxy)-6-methoxybenzofuran-2-yl)ethanone (Example 1D, 2.40 g, 8.1 mmole) in tetrahydrofuran (20 mL) added dropwise over 10 min. The resulting mixture was then stirred at −78° C. for 45 min. Then chlorotrimethylsilane (1.18 mL, 9.31 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (200 mL), saturated sodium bicarbonate (30 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (40 mL), cooled to −20° C. and treated with solid sodium bicarbonate (0.10 g) followed by N-bromosuccinimide (1.44 g, 8.1 mmol) added in small portions over 15 min. The reaction mixture was allowed to warm to 0° C. over 2h and then quenched by addition of ethyl acetate (300 mL) and saturated sodium bicarbonate. The organic phase was washed with brine, dried over anhydrous magnesium sulfate and evaporated to give an orange oil. Chromatography on silica gel (4×12 cm, elution toluene—ethyl acetate 0-5%) gave 2.62 g (86% yield) of the title bromomethylketone as a yellow solid. Recrystallization from ethyl acetate (10 mL) and hexane (20 mL) gave yellow prisms (2.30 g). LC (Method E): 1.977 min. HRMS (ESI) calcd for $C_{18}H_{16}BrO_4$ [M+H]$^+$ m/z 375.0226. found 375.0277. $^1$H NMR (CDCl$_3$, 600 MHz) δ 3.84 (s, 3H), 4.33 (s, 2H), 5.14 (s, 2H), 6.38 (d, J=1.76 Hz, 1H), 6.64 (broad s, 1H), 7.35 (broad t, 1H), 7.40 (broad t, 2H), 7.44 (broad d, 2H), 7.70 (s, 1H).

1F. 6-(4-(Benzyloxy)-6-methoxybenzofuran-2-yl)-2-bromoimidazo[2,1-b][1,3,4]thiadiazole

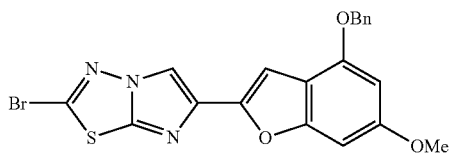 [SMILES: COc1cc(OCc2ccccc2)c2cc(-c3cn4nc(Br)sc4n3)oc2c1]

A mixture of 1-(4-(benzyloxy)-6-methoxybenzofuran-2-yl)-2-bromoethanone (Example 1E, 3.00 g, 8.0 mmol) and 5-bromo-1,3,4-thiadiazol-2-amine (1.65 g, 9.16 mmol) in isopropanol (100 mL) was heated is a pressure flask equipped with a magnetic stirring bar at 78-80° C. for 18 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane due to poor solubility) gave 2.96 g of the title imidazothiadiazole contaminated with some 1-(4-(benzyloxy)-6-methoxybenzofuran-2-yl)ethanone. The solid material was triturated with ethyl acetate (20 mL), filtered, washed with ethyl acetate (10 ml) and dried in vacuo to give 2.34 g (64% yield) of pure title imidazothiadiazole as an off white solid which is used as such for the next step. LC (Method E): 2.188 min. HRMS (ESI) calcd for $C_{20}H_{15}BrN_3O_3S$ [M+H]$^+$ m/z 456.00175. found 456.00397. $^1$H NMR (CDCl$_3$, 600 MHz) δ 3.82 (s, 3H), 5.16 (s, 2H), 6.38 (d, J=1.67 Hz, 1H), 6.66 (broad s, 1H), 7.15 (s, 1H), 7.31 (broad t, 1H), 7.38 (broad t, 2H), 7.45 (broad d, 2H), 8.02 (s, 1H).

1G. 6-(4-(Benzyloxy)-6-methoxybenzofuran-2-yl)-2-methoxyimidazo[2,1-b][1,3,4]thiadiazole

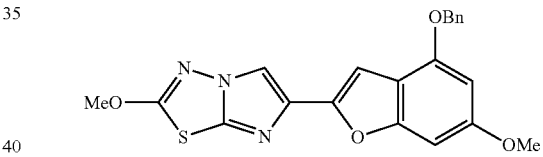

A solution of 6-(4-(benzyloxy)-6-methoxybenzofuran-2-yl)-2-bromoimidazo[2,1-b][1,3,4]thiadiazole (Example 1F, 2.30 g, 5.04 mmol) in a mixture of dichloromethane (180 mL) and methanol (45 mL) was treated at 22° C. with 4.2 mL of a 25 wt. % solution of sodium methoxide in methanol (0.2 mmol) added in one portion. More methanol (45 mL) was added and the mixture was stirred for 1 h. The reaction mixture was quenched by the addition of 25 mL of 1N hydrochloric acid followed by 20 ml of saturated sodium bicarbonate. The solvent was evaporated under reduced pressure and the residue was diluted with dichloromethane (400 mL), washed with brine, dried over anhydrous magnesium sulfate and evaporated in vacuo. Chromatography of the residue on silica gel (3×10 cm, elution with dichloromethane—ethyl acetate 0-4%) gave 1.70 g (83% yield) of the title compound as a white solid. This material was recrystallized from ethyl acetate (30 mL per gram, 80% recovery) to give white needles. LC (Method D): 2.293 min. FIRMS (ESI) calcd for $C_{21}H_{18}N_3O_4S$ [M+H]$^+$ m/z 408.1013. found 408.1024. $^1$H NMR (CDCl$_3$, 600 MHz) δ 3.81 (s, 3H), 4.18 (s, 3H), 5.16 (s, 2H), 6.37 (d, J=1.75 Hz, 1H), 6.67 (broad s, 1H), 7.07 (s, 1H), 7.31 (broad t, 1H), 7.37 (broad t, 2H), 7.45 (broad d, 2H), 7.81 (s, 1H).

1H. 6-Methoxy-2-(2-methoxyimidazo[2,1-b][1,3,4]thiadiazol-6-yl)benzofuran-4-ol

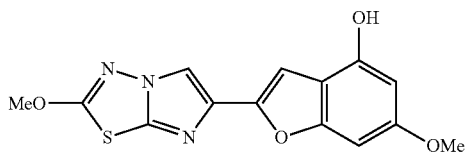 [SMILES: COc1cc(O)c2cc(-c3cn4nc(OC)sc4n3)oc2c1]

A mixture of 6-(4-(benzyloxy)-6-methoxybenzofuran-2-yl)-2-methoxyimidazo[2,1-b][1,3,4]thiadiazole (Example 1G, 1.250 g, 3.06 mmol) and pentamethylbenzene (3.17 g, 21.4 mmol) in dichloromethane (200 mL) was cooled to −78° C. under a nitrogen atmosphere and then treated immediately (to avoid crystallization) with 8 mL (8 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (6 g) in water (100 mL) added in one portion. The cooling bath was removed and the resulting mixture was stirred at room temperature for 1 h. The solid formed was filtered, washed successively with water (50 m) and dichloromethane (50 mL). The filter cake was allowed to soak with anhydrous ethanol (15 ml) and then sucked dry. The white solid obtained was then dried under vacuum for 24 h to give 0.788 g (80% yield) of pure title material (>95% by hplc). The combined filtrate and washings were diluted with dichloromethane (600 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and hexamethylbenzene) was triturated with toluene (20 mL), the solid collected and washed with toluene (20 mL) to give 0.186 g (19% yield, 99% combined yield) of title material as a tan solid (>95% by hplc). LC (Method E): 1.444 min. HRMS (ESI) calcd for $C_{14}H_{12}N_3O_4S$ [M+H]$^+$ m/z 318.0543. found 318.0578. $^1$H NMR (DMSO-d$_6$, 600 MHz) δ 3.71 (s, 3H), 4.16 (s, 3H), 6.21 (d, J=1.87 Hz, 1H), 6.61 (broad s, 1H), 6.95 (s, 1H), 8.29 (s, 1H), 9.96 (s, 1H).

Example 1

2-Methoxy-6-(6-methoxy-4-((2-methylthiazol-4-yl)methoxy)benzofuran-2-yl)imidazo[2,1-b][1,3,4]thiadiazole

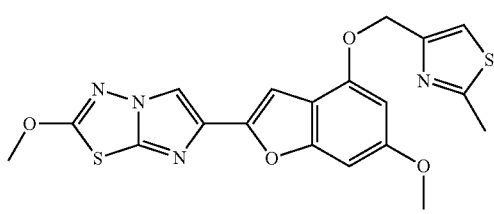 [SMILES: COc1cc(OCc2csc(C)n2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1H, 0.100 g, 0.315 mmol) and triphenylphosphine (0.123 g, 0.47 mmol) was maintained under vacuum for 10 minutes. The mixture was flushed with nitrogen and then charged with dry THF (8 mL) and (2-methylthiazol-4-yl)methanol (Example 1A, 0.049 g, 0.38 mmol). The mixture was warmed to 50° C. and sonicated for 5 minutes. The cooled mixture was treated with a solution of DIAD (0.096 g, 0.47 mmol) in dry THF (2 mL) added in three portions dropwise over 20 minutes. The mixture was homogeneous after 40 min. and was stirred at 22° C. for 6 h. The reaction mixture was diluted with dichloromethane (250 mL), washed with sat. sodium bicarbonate, brine and dried over anhydrous MgSO$_4$. Evaporation gave a semi-solid residue which was purified by chromatography on silica gel (2.5×10 cm, dichloromethane/EtOAc 8:2) to provide the title material (0.103 g, 76%) as white cubes. LC (Method A): 2.224 min. HRMS (ESI) calcd for $C_{19}H_{17}N_4O_4S_2$ [M+H]$^+$ m/z 429.0686. found 429.0605. $^1$H NMR (CDCl$_3$, 600 MHz) δ 7.82 (s, 1H), 7.17 (s, 1H), 7.06 (s, 1H), 6.67 (m, 1H), 6.39 (d, J=1.89 Hz, 1H), 5.25 (d, J=0.9 Hz, 2H), 4.18 (s, 3H), 3.82 (s, 3H), 2.72 (s, 3H).

Example 2

2-Methoxy-6-(6-methoxy-4-((2-(trifluoromethyl)thiazol-4-yl)methoxy)benzofuran-2-yl)imidazo[2,1-b][1,3,4]thiadiazole

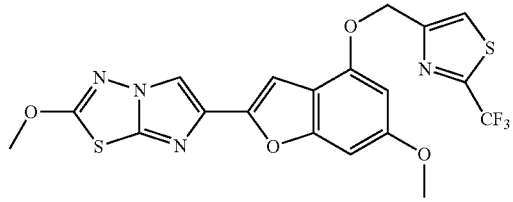 [SMILES: COc1cc(OCc2csc(C(F)(F)F)n2)c2cc(-c3cn4nc(OC)sc4n3)oc2c1]

2A. Ethyl 2-(trifluoromethyl)thiazole-4-carboxylate

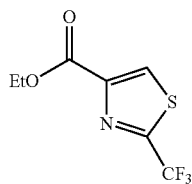

A mixture of 2,2,2-trifluoroacetamide (7.12 g, 63 mmol) and Lawesson's reagent (15.3 g, 37.8 mmol) in THF (60 mL) was heated at reflux for 18 hours. The reaction was then cooled down to RT and treated with ethyl bromopyruvate (8.0 mL, 63 mmol). The reaction was stirred at reflux for an additional 18 hours, then concentrated under vacuum and diluted with ethyl acetate. This mixture was washed with water (1×) and brine (1×), dried over anhydrous magnesium sulfate, filtered and concentrated. The residue was purified by silica gel chromatography (8×11 cm, toluene, then second time with 120 g silica gel, hexane/ethyl acetate) to give the title material (4.47 g, 32%) as a pale yellow solid. $^1$H NMR (CDCl$_3$, 400 MHz) δ 8.37 (s, 1H), 4.45 (q, J=7.0 Hz, 2H), 1.41 (t, J=7.0 Hz, 1H).

2B. (2-(Trifluoromethyl)thiazol-4-yl)methanol

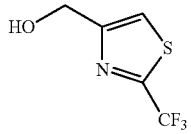

Ethyl 2-(trifluoromethyl)thiazole-4-carboxylate (Example 2A, 1.50 g, 6.66 mmol) was reacted as described in Example 1A and afforded the desired title material (0.95 g, 78%) as a clear oil after distillation (b.p.: 55-65° C./0.2 torr). $^1$H NMR (CDCl$_3$, 400 MHz) δ 7.47 (s, 1H), 4.85 (s, 2H), 2.25 (br s, 1H).

Example 2

2-Methoxy-6-(6-methoxy-4-((2-(trifluoromethyl)thiazol-4-yl)methoxy)benzofuran-2-yl)imidazo[2,1-b][1,3,4]thiadiazole

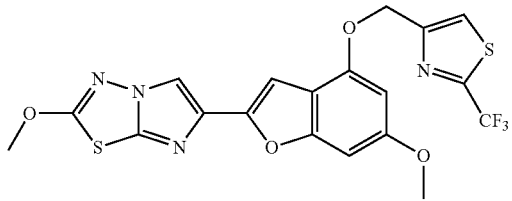 [SMILES: COc1cc(OCc2csc(C(F)(F)F)n2)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.100 g, 0.315 mmol) and (2-(trifluoromethyl)thiazol-4-yl)methanol (Example 2B, 0.075 g, 0.409 mmol) were reacted as described in Example 1 and afforded the title material (0.070, 46%) after crystallization in AcOEt. LC (Method B): 2.448 min. HRMS (ESI) calcd for C$_{19}$H$_{14}$F$_3$N$_4$O$_4$S$_2$ [M+H]$^+$ m/z 483.0403. found 483.0411. $^1$H NMR (CDCl$_3$, 600 MHz) δ 7.82 (s, 1H), 7.17 (s, 1H), 7.06 (s, 1H), 6.67 (m, 1H), 6.39 (d, J=1.89 Hz, 1H), 5.25 (d, J=0.9 Hz, 2H), 4.18 (s, 3H), 3.82 (s, 3H), 2.72 (s, 3H).

Example 3

2-Methoxy-6-(6-methoxy-4-((2-phenylthiazol-4-yl)methoxy)benzofuran-2-yl)imidazo[2,1-b][1,3,4]thiadiazole

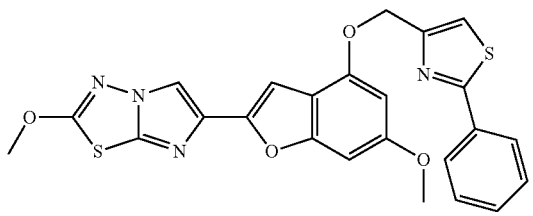 [SMILES: COc1cc(OCc2csc(-c3ccccc3)n2)c2cc(-c3cn4nc(OC)sc4n3)oc2c1]

3A. Methyl 2-phenylthiazole-4-carboxylate

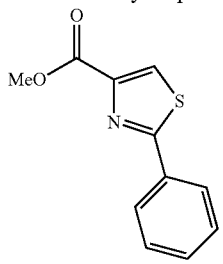

A solution of benzothioamide (4.0 g, 29.2 mmol) in THF (80 mL) was treated dropwise with ethyl bromopyruvate (7.6 g, 39 mmol) and heated at reflux for 18 hours. The reaction was then concentrated under vacuum, diluted with ethyl acetate, washed with water (1×), brine (1×) and dried over anhydrous magnesium sulfate. The residue obtained after concentration was purified by silica gel chromatography (4.5×11 cm, 20% AcOEt/toluene), followed by a second purification with 20% AcOEt/hexane. The title material was obtained after concentration as a yellow oil (5.25, 77%). $^1$H NMR (CDCl$_3$, 400 MHz): 8.14 (s, 1H) 8.00 (m, 2H) 7.46-7.42 (m, 3H) 4.43 (q, J=7.0 Hz, 2H) 1.42 (t, J=7.3 Hz, 3H).

3B. (2-Phenylthiazol-4-yl)methanol

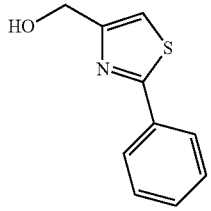 [SMILES: OCc1csc(-c2ccccc2)n1]

In a 250 mL round-bottom flask, methyl 2-phenylthiazole-4-carboxylate (Example 3A, 1.50 g, 6.43 mmol) was dissolved in ethyl ether (40 mL). The solution was cooled down to −78° C. and treated with lithium aluminum hydride (0.75 g, 19.76 mmol) portionwise over 20 minutes. The reaction was stirred at −78° C. for 3.5 hours, then treated with 20 mL of a saturated solution of Na$_2$SO$_4$. The reaction was allowed to reach RT and was diluted with ethyl acetate, washed with HCl 1N (1×), brine (1×), dried over anhydrous magnesium sulfate, filtered and concentrated. The residue was purified by silica gel chromatography (3×12 cm, 30% ethyl acetate/dichloromethane) to give a pale yellow oil (1.06 g) which was then distilled (bulb to bulb, bp: 110-120° C./0.2 torr) and provided the title material (0.88 g, 72%) as a clear oil. $^1$H NMR (CDCl$_3$, 400 MHz): 7.95-7.90 (m, 2H) 7.45-7.40 (m, 3H) 7.16 (s, 1H) 4.82 (s, 2H) 2.34 (br s, 1H).

Example 3

2-Methoxy-6-(6-methoxy-4-((2-phenylthiazol-4-yl)methoxy)benzofuran-2-yl)imidazo[2,1-b][1,3,4]thiadiazole

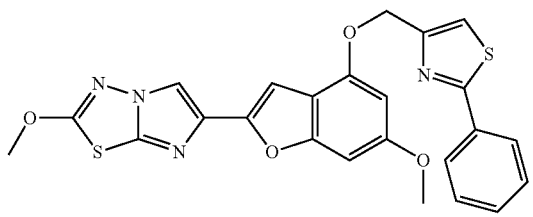 [SMILES: COc1cc(OCc2csc(-c3ccccc3)n2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1H, 0.800 g, 2.52 mmol), triphenylphosphine (0.992 g, 3.78 mmol) and (2-phenylthiazol-4-yl)methanol (Example 3B, 0.555 g, 2.90 mmol) in a 200 mL flask fitted with an addition funnel was maintained under vacuum for ten minutes. The mixture was then flushed with nitrogen and charged with dry tetrahydrofuran (60 mL, distilled over lithium aluminum hydride). The solution was warmed to ~50° C. and then sonicated for 5 min. The cooled heterogeneous mixture was then treated at 22° C. with a solution of diisopropyl azodicarboxylate (0.663 g, 3.28 mmol) in tetrahydrofuran (15 mL), added dropwise over 2.5 h. The reaction was homogeneous (pale yellow) at the end of the addition. The mixture was then stirred for another 2.5 h (total 5 h). The reaction mixture was then diluted with dichloromethane (400 mL), washed with saturated sodium bicarbonate (20 mL), brine and dried (anhydrous magnesium sulfate). Evaporation gave a white solid which was chromatographed on silica gel (3×12 cm, elution dichloromethane—ethyl acetate 98.5:1.5 to 97:3). The fractions were collected and evaporated to give the desired compound (1.40 g) as a white solid, contaminated with hydrazide by tlc. Crystallization in ethyl acetate (40 mL) gave the pure title material (0.838 g, 68%) as a white solid. The mother liquors (0.475 g) were chromatographed on silica gel (3×12 cm, elution dichloromethane—ethyl acetate 98.5:1.5 to 97:3) to give after crystallization from ethyl acetate (30 mL) to provide additional desired compound (0.160 g, 13%, total 81%) as a white solid. LC (Method C): 2.480 min. HRMS (ESI) calcd for $C_{24}H_{19}N_4O_4S_2$ [M+H]+ m/z 491.0842. found 491.0865. $^1$H NMR (CDCl$_3$, 400 MHz) 3.85 (s, 3H) 4.21 (s, 3H) 5.33-5.55 (m, 2H) 6.48 (d, J=1.96 Hz, 1H) 6.72 (dd, J=1.96, 0.78 Hz, 1H) 7.12 (s, 1H) 7.36-7.39 (m, 1H) 7.41-7.50 (m, 3H) 7.86 (s, 1H) 7.95-8.02 (m, 2H).

Example 4

2-Methoxy-6-(6-methoxy-4-((4-phenylthiazol-2-yl)methoxy)benzofuran-2-yl)imidazo[2,1-b][1,3,4]thiadiazole

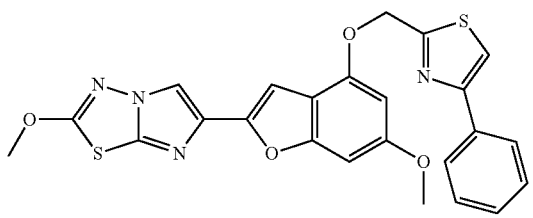 [SMILES: COc1cc(OCc2nc(-c3ccccc3)cs2)c2cc(-c3cn4nc(OC)sc4n3)oc2c1]

4A. Ethyl 2-amino-2-thioxoacetate

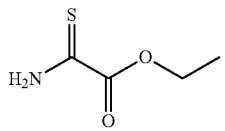

A solution of ethyl 2-amino-2-oxoacetate (5.00 g, 42.7 mmol) in tetrahydrofuran (150 mL) was treated with powdered (mortar and pestle) Lawesson's Reagent (9.50 g, 23.49 mmol) and the resulting orange clear solution was heated under reflux (bath temperature 85° C.) for 4 h (TLC product with higher Rf formed with some starting material left). The cooled mixture was concentrated under reduced pressure and the residue was diluted with ethyl acetate (400 mL) washed with saturated sodium bicarbonate, brine and dried over anhydrous magnesium sulfate. Evaporation gave an orange solid which was chromatographed on silica gel (3×10 cm, elution toluene—ethyl acetate 9:1) and provided the title material (3.189 g, 56%) of a yellow solid. LC (Method C): 0.816 min. $^1$H NMR (CDCl$_3$, 400 MHz) δ ppm: 1.41 (t, J=7.0 Hz, 3H), 4.38 (q, J=7.0 Hz, 2H), 7.69 (br s, 1H) 8.24 (br s, 1H).

4B. Ethyl 4-phenylthiazole-2-carboxylate

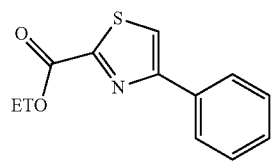

A mixture of 2-bromo-1-phenylethanone (1.790 g, 8.99 mmol) and ethyl 2-amino-2-thioxoacetate (Example 4A, 1.20 g, 9.01 mmol) in benzene (80 mL) and ethanol (10 mL) was stirred at room temperature for 18 h. The mixture was heated at 80° C. for 1 h. The solvent was evaporated under reduced pressure and the residue was partitioned between ethyl acetate (300 mL) and saturated aqueous sodium bicarbonate (100 mL). The organic phase was washed with brine, dried over anhydrous magnesium sulfate and concentrated in vacuo. The residual clear oil was chromatographed on silica gel (4×10 cm, elution toluene-ethyl acetate 0-2-4%) and gave a yellow oil (1.588 g). This was distilled in vacuo (bp: 105-115° C./0.1 torr, bulb to bulb distillation, air bath temperature) to provide the title material (1.409 g, 67%) as a pale yellow syrup which solidified to an almost colorless solid upon standing. LC (Method C): 2.009 min. HRMS (ESI) calcd for $C_{12}H_{12}NO_2S$ [M+H]+ m/z 234.0583. found 234.0597. $^1$H NMR (CDCl$_3$, 400 MHz) δ ppm: 1.48 (t, J=7.2 Hz, 3H), 4.52 (q, J=7.2 Hz, 2H), 7.35-7.49 (m, 3H), 7.75 (s, 1H), 7.93-8.00 (m, 2H).

4C. 2-(Hydroxymethyl)-4-phenylthiazole

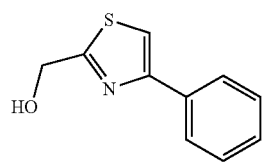 [SMILES: OCc1nc(-c2ccccc2)cs1]

A solution of ethyl 4-phenylthiazole-2-carboxylate (Example 4B, 1.300 g, 5.57 mmol) in diethyl ether (60 mL) in a 500 mL flask under a nitrogen atmosphere was cooled to −40° C. (dry ice—water—calcium chloride bath) and treated with solid LiAlH$_4$ (0.40 g, 10.54 mmol) added all at once. The mixture was stirred at −40° C. over 2.5 h. The reaction was quenched by dropwise addition of ethyl acetate (1 mL), water (0.4 mL) followed by 15% aqueous sodium hydroxide (0.4 mL) and water (1.2 mL). The bath was then removed and the mixture was stirred at room temperature for 50 min. The solid formed was filtered and washed with ether (50 mL). The combined filtrate and washing was washed with brine (20 mL) and dried over anhydrous magnesium sulfate. Evaporation gave a yellow oil which was purified by silica gel chromatography (2.5×8 cm, elution toluene—ethyl acetate 9:1, 8:2 to 7:3). The resulting light yellow oil (0.931 g) was then distilled in vacuo (bp: 105-110° C./0.1 torr, bulb to bulb, air bath temperature) to provide the title material (0.918 g, 86%) of a colorless syrup. LC (Method C): 1.672 min. HRMS (ESI) calcd for $C_{10}H_{10}NOS$ [M+H]$^+$ m/z 192.0478. found 192.0508. $^1$H NMR (CDCl$_3$, 400 MHz) δ ppm: 2.90 (br t, 1H), 5.02 (d, J=4.30 Hz, 2H), 7.31-7.38 (m, 1H), 7.39-7.45 (m, 2H), 7.46 (d, J=0.8 Hz, 1H), 7.85-7.92 (m, 2H).

4D. 2-(Bromomethyl)-4-phenylthiazole

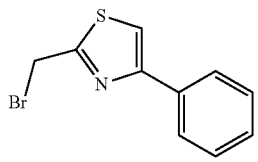 [SMILES: BrCc1nc(-c2ccccc2)cs1]

A solution of (4-phenylthiazol-2-yl)methanol (Example 4C, 0.530 g, 2.77 mmol) in dichloromethane (10 mL) was cooled to 0° C. (ice bath) and treated with PBr$_3$ (0.118 mL, 1.247 mmol) added dropwise over 2 min. A heavy white gum was immediately formed. After 10 min, the bath was removed and the solution was stirred at 22° C. for 4 h. The reaction mixture was quenched with ice (~10 g) and poured into a mixture of ethyl acetate (150 mL) and saturated sodium bicarbonate (50 mL). The organic phase was washed with brine, dried over anhydrous magnesium sulfate and concentrated in vacuo. The solid residue was chromatographed on silica gel (2.5×6 cm, elution toluene) to give the title material (0.561 g, 80%) as a light yellow oil which solidified in the fridge to a pale yellow solid. LC (Method C): 2.062 min. HRMS (ESI) calcd for $C_{10}H_9BrNS$ [M+H]$^+$ m/z 253.9634. found 253.9655. $^1$H NMR (CDCl$_3$, 400 MHz) δ ppm: 4.81 (s, 2H), 7.34-7.39 (m, 1H), 7.41-7.47 (m, 2H), 7.52 (s, 1H), 7.86-7.92 (m, 2H).

Example 4

2-Methoxy-6-(6-methoxy-4-((4-phenylthiazol-2-yl)methoxy)benzofuran-2-yl)imidazo[2,1-b][1,3,4]thiadiazole

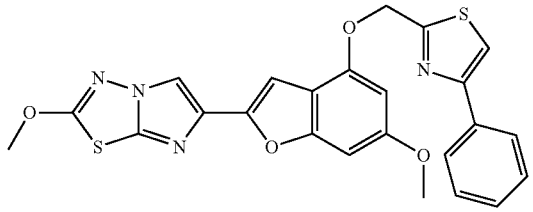 [SMILES: COc1cc(OCc2nc(-c3ccccc3)cs2)c2cc(-c3cn4nc(OC)sc4n3)oc2c1]

A suspension of 6-methoxy-2-(2-methoxyimidazo[2,1-b][1,3,4]thiadiazol-6-yl)benzofuran-4-ol (Example 1H, 0.080 g, 0.252 mmol) and 2-(bromomethyl)-4-phenylthiazole (0.128 g, 0.504 mmol) in N,N-Dimethylformamide (3 mL) was maintained under vacuum (10 mbar) for 5 minutes. The flask was then flushed with nitrogen and anhydrous freshly powdered (mortar and pestle) potassium carbonate (0.105 g, 0.756 mmol) was added all at once. The resulting mixture was stirred at room temperature with a few short sonication periods (~1 min) for 1 hour. The heterogeneous mixture became almost homogeneous (except the potassium carbonate) after 10 min and started to precipitate again to a cream solid. The reaction mixture was quenched with 1N hydrochloric acid (2 mL) and then partitioned between dichloromethane (150 mL) and saturated sodium bicarbonate (20 mL). The organic phase was washed with brine, dried over anhydrous magnesium sulfate and concentrated in vacuo. The solid pale yellow residue was chromatographed on silica gel (2.5×6 cm, elution dichloromethane-ethyl acetate 0-2-5%) to give the title material (0.116 g, 94%) as a pale yellow solid. Crystallization in ethyl acetate (12 mL) provided the title material (0.086 g) as a pale yellow solid. LC (Method C): 2.474 min. HRMS (ESI) calcd for $C_{24}H_{19}N_4O_4S_2$ [M+H]$^+$ m/z 491.0842. found 491.0864. $^1$H NMR (CDCl$_3$, 400 MHz) δ ppm: 3.86 (s, 3H), 4.22 (s, 3H), 5.54 (s, 2H), 6.48 (d, J=1.96 Hz, 1H), 6.75 (broad d, 1H), 7.15 (s, 1H), 7.32-7.39 (m, 1H), 7.41-7.49 (m, 2H), 7.53 (s, 1H), 7.87 (s, 1H), 7.90-7.95 (m, 2H).

Example 5

4-(4-(((6-Methoxy-2-(2-methoxyimidazo[2,1-b][1,3,4]thiadiazol-6-yl)benzofuran-4-yl)oxy)methyl)thiazol-2-yl)morpholine

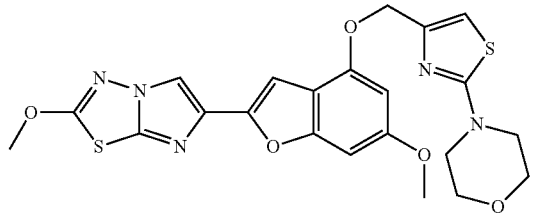 [SMILES: COc1cc(OCc2csc(N3CCOCC3)n2)c2cc(-c3cn4nc(OC)sc4n3)oc2c1]

5A. Methyl 2-morpholinothiazole-4-carboxylate

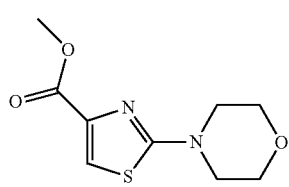

A solution of methyl 2-bromothiazole-4-carboxylate (0.20 g, 0.901 mmol) in THF (10 mL) was treated with morpholine (0.17 mL, 1.94 mmol) and refluxed for 18 h. The reaction was then diluted with ethyl acetate and washed with sat. NaHCO$_3$ (1×), brine (1×) and dried over anhydrous magnesium sulfate, filtered and concentrated. The residue was purified by silica gel chromatography (2.5×10 cm, 50% AcOEt/CH$_2$Cl$_2$) to give the title material (0.192 g, 92%) as a yellow solid. ¹H NMR (CDCl₃, 400 MHz) δ ppm: 7.44 (s, 1H) 3.82 (s, 3H) 3.75 (m, 4H) 3.45 (m, 4H).

5B. (2-Morpholinothiazol-4-yl)methanol

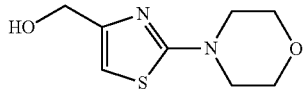

A solution of methyl 2-morpholinothiazole-4-carboxylate (0.76 g, 3.33 mmol) in ethyl ether (20 mL) was treated portion wise over 10 min. with lithium aluminum hydride (0.38 g, 10.01 mmol). The mixture was stirred at −78° C. for 4 hours, then slowly treated with ethyl acetate (10 mL) and sat. Na₂SO₄ (20 mL). The mixture was allowed to warm up to RT, diluted with ethyl acetate, washed with sat. NaHCO₃ (1×), brine (1×), dried over anhydrous magnesium sulfate, filtered and concentrated. The residue was purified on silica gel chromatography (3×10 cm, 25% AcOEt/CH₂Cl₂ to 100% AcOEt) to give the title material as a beige solid (0.458 g) which was then distilled (bulb to bulb, 135-145° C./0.2 torr) and afforded the desired product (0.455 g, 68%) as a white solid. LC (Method F): 0.873 min. FIRMS (ESI) calcd for $C_8H_{13}N_2O_2S$ [M+H]⁺ m/z 201.07. found 201.2. ¹H NMR (CDCl₃, 400 MHz) δ ppm: 6.43 (s, 1H) 4.53 (d, J=3.9 Hz, 2H) 3.79 (m, 4H) 3.44 (m, 4H) 2.17 (s, 1H).

Example 5

4-(4-(((6-Methoxy-2-(2-methoxyimidazo[2,1-b][1,3,4]thiadiazol-6-yl)benzofuran-4-yl)oxy)methyl)thiazol-2-yl)morpholine

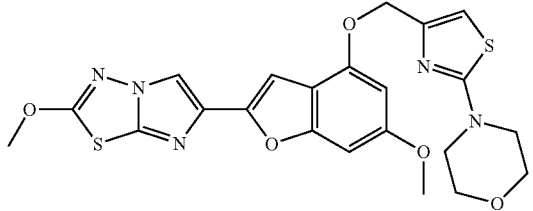 [SMILES: COc1cc(OCc2csc(N3CCOCC3)n2)c2cc(-c3cn4nc(OC)sc4n3)oc2c1]

6-Methoxy-2-(2-methoxyimidazo[2,1-b][1,3,4]thiadiazol-6-yl)benzofuran-4-ol (Example 1H, 0.10 g, 0.315 mmol), triphenylphosphine (0.124 g, 0.473 mmol) and (2-morpholinothiazol-4-yl)methanol (Example 5B, 0.086 g, 0.429 mmol) were added in a 25 mL round-bottom flask and purged under vacuum and nitrogen. Tetrahydrofuran (8 mL) was then added and the mixture was treated with DIAD (0.083 g, 0.410 mmol) in tetrahydrofuran (10 mL). The mixture was stirred at 22° C. for 1 hour and diluted with ethyl acetate. This was washed with sat. NaHCO₃ (1×) and brine (1×), dried over anhydrous magnesium sulfate, filtered and concentrated. The residue was purified on silica gel column chromatography (2.5×10 cm, 40% ethyl acetate in CH₂Cl₂) and the residue obtained after concentration was crystallized in ethyl acetate to give the title material as crystals (0.083 g, 53%) and as an amorphous impure solid from the mother liquor (0.169 g). LC (Method F): 2.466 min. HRMS (ESI) calcd for $C_{22}H_{22}N_5O_5S_2$ [M+H]⁺ m/z 500.1057. found 500.1075. ¹H NMR (CDCl₃, 400 MHz) δ ppm: 7.82 (s, 1H) 7.07 (s, 1H) 6.67 (d, J=2 Hz, 1H) 6.62 (s, 1H) 6.40 (d, J=1.5 Hz, 1H) 5.10 (s, 2H) 4.19 (s, 3H) 3.82 (s, 3H) 3.81 (m, 4H) 3.46 (m, 4H).

Example 6

2-Methoxy-6-(6-methoxy-4-((2-((2-methoxyethoxy)methyl)thiazol-4-yl)methoxy)benzofuran-2-yl)imidazo[2,1-b][1,3,4]thiadiazole

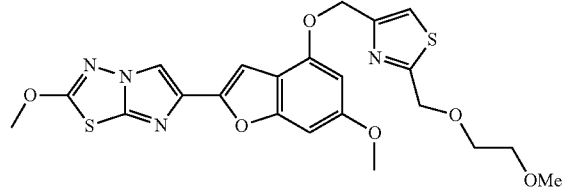 [SMILES: COCCOCc1nc(COc2cc(OC)cc3oc(-c4cn5nc(OC)sc5n4)cc23)cs1]

6A. 2-(2-Methoxyethoxy)acetamide

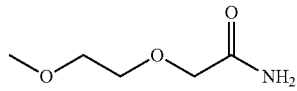

A solution of 2-(2-methoxyethoxy)acetic acid (5.0 g, 37.3 mmol) in CH₂Cl₂ (50 mL) was treated with oxalyl chloride (9.5 mL, 109 mmol) and DMF (2 drops) and the reaction was stirred for 3 hours. After evaporation under vacuum, the residue was co-evaporated with CH₂Cl₂ (2×) and then dissolved in THF (10 mL) and treated dropwise with a mixture of ammonium hydroxide (12 mL), THF (25 mL) and water (10 mL) for 5 min. The reaction was then stirred at 0-5° C. for 30 min. then at 22° C. for 1 h. The reaction was diluted with CH₂Cl₂, washed with water (1×), HCl 1N (1×), sat. NaHCO₃ (1×) and brine (1×), dried over anhydrous magnesium sulfate, filtered and concentrated. As the product appeared to be soluble in water, the aqueous phase was evaporated under vacuum and extracted with CH₂Cl₂ (5×200 mL), dried over anhydrous magnesium sulfate, filtered and concentrated to give the title material (3.59 g, 72%) as an oil which solidified. This was distilled (bulb to bulb, 105-115° C./0.2 torr) to provide the pure desired product (3.39 g) as a clear oil which solidified as a white solid. ¹H NMR (CDCl₃, 400 MHz) δ ppm: 6.93 (very broad s, 1H), 5.43 (very broad s, 1H), 3.99 (s, 2H), 3.66-3.70 (m, 2H), 3.53-3.56 (m, 2H), 3.39 (s, 3H).

6B. 2-(2-Methoxyethoxy)ethanethioamide

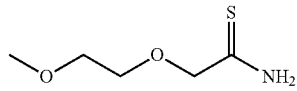

A solution of 2-(2-methoxyethoxy)acetamide (Example 6A, 3.39 g, 25.5 mmol) in THF (40 mL) was treated with Lawesson's reagent (6.55 g, 16.19 mmol) and the reaction was refluxed for 18 hours. The reaction was then allowed to cool down to RT and was concentrated under vacuum, diluted with ethyl acetate, washed with sat. NaHCO₃ (1×) and brine (1×). The aqueous phases were extracted with ethyl acetate (2×200 mL) and the organic extracts were dried over anhydrous magnesium sulfate, filtered and concentrated. The residue was purified by silica gel chromatography (3.5×11 cm, 30% AcOEt/CH₂Cl₂) to give the title material (3.26 g, 86%) as a yellow oil. ¹H NMR (CDCl₃, 400 MHz) δ ppm: 8.58 (very broad s, 1H), 7.50 (very broad s, 1H), 4.36 (s, 2H), 3.66-3.69 (m, 2H), 3.53-3.56 (m, 2H), 3.39 (s, 3H).

6C. Ethyl 2-((2-methoxyethoxy)methyl)thiazole-4-carboxylate

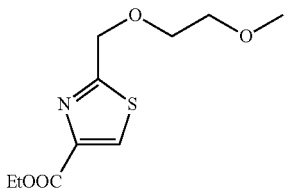 [SMILES: CCOC(=O)c1csc(COCCOC)n1]

To a solution of 2-(2-methoxyethoxy)ethanethioamide (Example 6B, 3.26 g, 21.85 mmol) in ethanol (60 mL) was added dropwise ethylbromopyruvate (3.7 mL, 29.5 mmol) and the mixture was refluxed for 18 hours. The reaction was then concentrated under vacuum, diluted with ethyl acetate, washed with water (1×), brine (1×), dried over anhydrous magnesium sulfate, filtered and concentrated. The residue was purified by silica gel column chromatography (3.5×10 cm, 30% ethyl acetate/CH₂Cl₂) to give the title material (4.36 g, 81%) as an oil. LC (Method F): 1.791 min. ¹H NMR (CDCl₃, 400 MHz) δ ppm: 8.16 (s, 1H), 4.87 (s, 2H), 4.41 (q, J=7.10 Hz, 2H), 3.74-3.77 (m, 2H), 3.57-3.60 (m, 2H), 3.39 (s, 3H), 1.39 (t, J=7.10 Hz, 3H).

6D. (2-((2-Methoxyethoxy)methyl)thiazol-4-yl)methanol

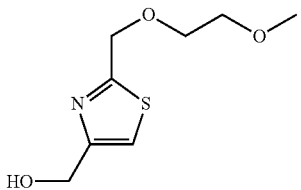

To a solution of ethyl 2-((2-methoxyethoxy)methyl)thiazole-4-carboxylate (Example 6C, 2.27 g, 9.25 mmol) in ether (50 mL) was added portion wise lithium aluminum hydride (1.06 g, 27.9 mmol) over 10 min. at −78° C. The reaction was then stirred at −78° C. for 1 hour. Ethyl acetate (10 mL) was then added to the reaction followed by water (20 mL) and the reaction was allowed to reach RT. The mixture was then diluted with ethyl acetate, washed with HCl 1N (1×) and brine (1×). The combined aqueous phases were extracted with ethyl acetate (2×300 mL), dried over anhydrous magnesium sulfate, filtered and concentrated. The residue was purified by silica gel chromatography (3.5×10 cm, ethyl acetate) to give the title material (0.357 g, 19%) as a brown oil. LC (Method F): 1.791 min. ¹H NMR (CDCl₃, 400 MHz) δ ppm: 7.16 (s, 1H), 4.82 (s, 2H), 4.74 (broad s, 2H), 3.7-3.75 (m, 2H), 3.54-3.61 (m, 2H), 3.38 (s, 3H), 2.28 (broad s, 1H).

6E. 4-(Bromomethyl)-2-((2-methoxyethoxy)methyl)thiazole

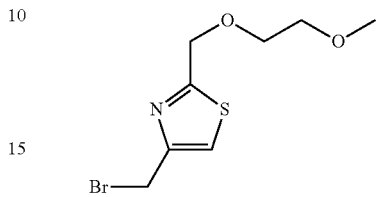

A solution of (2-((2-methoxyethoxy)methyl)thiazol-4-yl)methanol (0.35 g, 1.72 mmol) in ether (15 mL) was treated with PBr₃ (0.1 mL, 1.06 mmol) at RT. There is formation of a precipitate. The reaction was stirred at RT for 18 hours, then diluted with ethyl acetate and washed with sat. NaHCO₃ (1×) and brine (1×), dried over anhydrous magnesium sulfate, filtered and concentrated. The residue was purified by silica gel chromatography (3×10 cm, 20% ethyl acetate/CH₂Cl₂) to give the title material (0.233 g, 51%) as a clear oil. ¹H NMR (CDCl₃, 400 MHz) δ ppm: 7.27 (s, 1H), 4.83 (s, 2H), 4.55 (s, 2H), 3.73-3.76 (m, 2H), 3.57-3.60 (m, 2H), 3.39 (s, 3H).

Example 6

2-Methoxy-6-(6-methoxy-4-((2-((2-methoxyethoxy)methyl)thiazol-4-yl)methoxy)benzofuran-2-yl)imidazo[2,1-b][1,3,4]thiadiazole

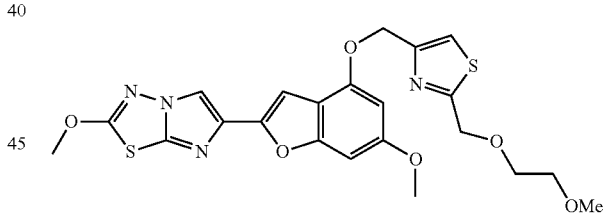

A suspension of 6-methoxy-2-(2-methoxyimidazo[2,1-b][1,3,4]thiadiazol-6-yl)benzofuran-4-ol (Example 1H, 0.10 g, 0.315 mmol) and 4-(bromomethyl)-2-((2-methoxyethoxy)methyl)thiazole (Example 6E, 0.10 g, 0.376 mmol) in DMF (5 mL) was purged under vacuum and nitrogen for 10 minutes. The mixture was then treated with potassium carbonate (0.10 g, 0.724 mmol) and the reaction was stirred at RT for 2.5 hours. The reaction was then diluted with dichloromethane, washed with water (1×), brine (1×), dried over anhydrous magnesium sulfate, filtered and concentrated. The residue was purified by silica gel chromatography (2.5×10 cm, 50% ethyl acetate/CH₂Cl₂) to give the title material which was crystallized in ethyl acetate and provided the desired title material (0.055 g, 35%) along with non-crystallized material (9 mgs, 6%). LC (Method F): 2.476 min. HRMS (ESI) calcd for C₂₂H₂₃N₄O₆S₂ [M+H]⁺ m/z 503.1054. found 503.1066. ¹H NMR (CDCl₃, 400 MHz) δ ppm: 7.82 (s, 1H), 7.35 (s, 1H), 7.05 (s, 1H), 6.68

(broad s, 1H), 6.39 (d, J=1.9 Hz, 1H), 5.28 (s, 2H), 4.86 (s, 2H), 4.19 (s, 3H), 3.82 (s, 3H), 3.74-3.77 (m, 2H), 3.58-3.61 (m, 2H), 3.39 (s, 3H).

Example 7

2-Methoxy-6-(6-methoxy-4-((5-phenyl-1,2,4-thiadiazol-3-yl)methoxy)benzofuran-2-yl)imidazo[2,1-b][1,3,4]thiadiazole

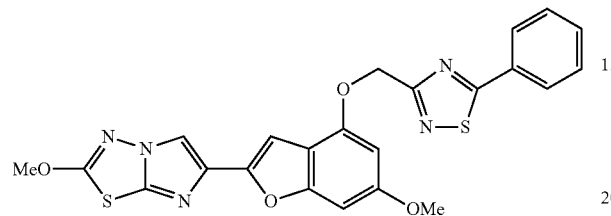

7A. Ethyl 5-phenyl-1,2,4-thiadiazole-3-carboxylate

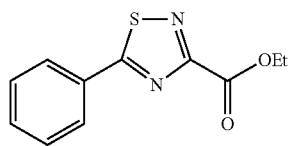 [SMILES: CCOC(=O)c1nsc(-c2ccccc2)n1]

A mixture of ethyl 2-oxo-1,3,4-oxathiazole-5-carboxylate (U.S. Publication No. 2005/0096362) (1.5 g, 8.56 mmol) and benzonitrile (4.37 ml, 42.8 mmol) in 1,2-dichlrotobenzene (15.42 ml, 137 mmol) was heated to 160° C. for 4 days. The reaction was then cooled down to RT and the solvent was evaporated by heated the reaction at 75° C. at maximum vacuum. The residue was purified on silica gel chromatography (100% $CH_2Cl_2$ to 3% EtOAc in $CH_2Cl_2$) to provide the title material (0.064 g, 3%). LC (Method B): 2.021 min. HRMS (ESI) calcd for $C_{11}H_{11}N_2O_2S$ $[M+H]^+$ m/z 235.0541. found 235. $^1$H NMR (CDCl$_3$, 400 MHz) δ ppm: 8.01-8.09 (m, 1H), 7.49-7.59 (m, 2H), 4.56 (q, J=7.17 Hz, 1H), 1.50 (t, J=7.24 Hz, 1H).

7B. (5-Phenyl-1,2,4-thiadiazol-3-yl)methanol

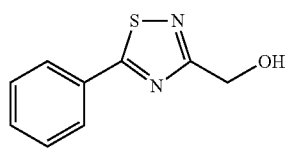 [SMILES: OCc1nsc(-c2ccccc2)n1]

To a solution of ethyl 5-phenyl-1,2,4-thiadiazole-3-carboxylate (Example 7A, 230 mg, 0.982 mmol) in anhydrous ethanol (3 mL, 51.4 mmol) was added NaBH$_4$ (149 mg, 3.93 mmol) at 0° C. The reaction mixture was heated to 80° C. for 30 min, then HCl 1N (1 mL) was added and ethanol was evaporated. Dichloromethane was added to the reaction followed by brine and this was extracted with dichloromethane (3×). The organic layers were dried over anhydrous magnesium sulfate and concentrated. The residue was purified on silica gel column chromatography (100% $CH_2Cl_2$ up to 10% EtOAc/$CH_2Cl_2$) to provide the title material (25 mgs, 13%). LC (Method B): 1.858 min. LCMS (APCI) calcd for $C_9H_9N_2OS$ $[M+H]^+$ m/z 193.04. found 193.0. $^1$H NMR (CDCl$_3$, 400 MHz) δ ppm: 7.89-8.03 (m, 2H), 7.46-7.62 (m, 3H), 4.99 (d, J=5.87 Hz, 2H), 2.81 (t, J=6.06 Hz, 1H).

Example 7

2-Methoxy-6-(6-methoxy-4-((5-phenyl-1,2,4-thiadiazol-3-yl)methoxy)benzofuran-2-yl)imidazo[2,1-b][1,3,4]thiadiazole

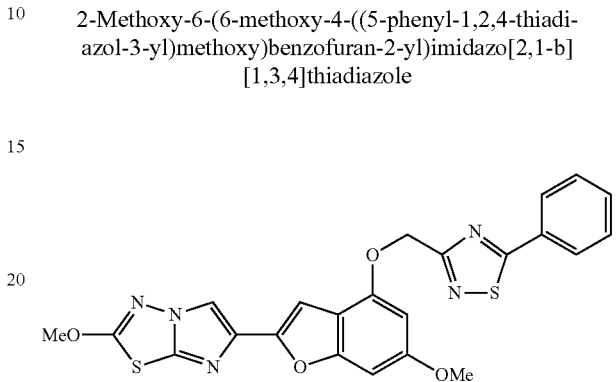

6-Methoxy-2-(2-methoxyimidazo[2,1-b][1,3,4]thiadiazol-6-yl)benzofuran-4-ol (Example 1H, 8.25 mg, 0.026 mmol) and (5-phenyl-1,2,4-thiadiazol-3-yl)methanol (Example 7B, 5 mg, 0.025 mmol) were put in a flask and this was flushed with N$_2$. Dry THF (4 mL) was added and to this resulting suspension was added tri-n-butylphosphine (0.017 mL, 0.065 mmol) and a solution of 1,1'-(azodicarbonyl)dipiperidine (16.57 mg, 0.065 mmol) in dry THF (2.5 mL) was added dropwise via a syringe pump over 2 h. The resulting being suspension was stirred for an additional 2 hours at RT, at which time LC showed that no starting material remained. The mixture was diluted with EtOAc, washed with 0.2N HCl, sat. aqueous NaHCO$_3$ and brine, dried over anhydrous magnesium sulfate, filtered and concentrated. The residue was purified on silica gel chromatography (50% dichloromethane/hexanes to 100% dichloromethane to 1% EtOAc/$CH_2Cl_2$ to 7% EtOAc/$CH_2Cl_2$) and lyophilized in MeCN/water to give the title material (6.2 mgs, 49%). LC (Method B): 2.615 min. HRMS (ESI) calcd for $C_{23}H_{18}N_5O_4S_2$ $[M+H]^+$ m/z 492.0795. found 492.0828. $^1$H NMR (CDCl$_3$, 400 MHz) δ ppm: 8.00 (dd, J=8.02, 1.37 Hz, 2H), 7.85 (s, 1H), 7.50-7.56 (m, 3H), 7.14 (s, 1H), 6.71-6.75 (m, 1H), 6.51 (d, J=1.57 Hz, 1H), 5.51 (s, 2H), 4.21 (s, 3H), 3.84 (s, 3H).

Example 8

2-Methoxy-6-(6-methoxy-4-((5-phenyl-1,3,4-thiadiazol-2-yl)methoxy)benzofuran-2-yl)imidazo[2,1-b][1,3,4]thiadiazole

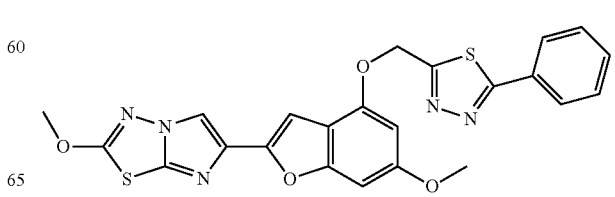

8A. Ethyl 5-phenyl-1,3,4-thiadiazole-2-carboxylate

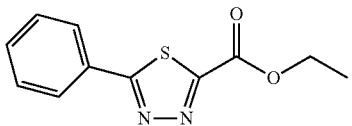 [SMILES: CCOC(=O)c1nnc(-c2ccccc2)s1]

To a solution of ethyl 2-(2-benzoylhydrazinyl)-2-oxoacetate (1 g, 4.23 mmol) in dry THF (5 ml, 61.0 mmol) was added the Lawesson's Reagent (1.079 g, 2.67 mmol). The reaction was stirred at r.t. for 2 h without any reaction. The mixture was then heated to 50° C. and then heated to reflux. Additional Lawesson's Reagent (1.079 g, 2.67 mmol) was added and after 16 h at reflux, the reaction was halfway completed. The mixture was evaporated to dryness and the residue was purified by silica gel column chromatography (50% $CH_2Cl_2$/hexanes up to 100% $CH_2Cl_2$) to provide the title material (0.35 g, 35%). LC (Method B): 2.063 min, LCMS (APCI) calcd for $C_{11}H_{11}N_2O_2S$ $[M+H]^+$ m/z 235.05. found 235.0. $^1$H NMR ($CDCl_3$, 400 MHz) δ ppm: 1.49 (t, J=1.00 Hz, 3H), 4.55 (q, J=1.00 Hz, 2H), 7.45-7.65 (m, 3H), 8.02-8.07 (m, 2H).

8B. (5-Phenyl-1,3,4-thiadiazol-2-yl)methanol

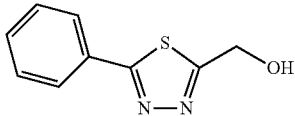 [SMILES: OCc1nnc(-c2ccccc2)s1]

To a solution of ethyl 5-phenyl-1,3,4-thiadiazole-2-carboxylate (350 mgs, 1.494 mmol) in anhydrous methanol (5 mL, 124 mmol) was added $NaBH_4$ (226 mgs, 5.98 mmol) at 0° C. The reaction mixture was stirred at ambient temperature for 16 h. AcOH (2 mL) was added and the reaction was concentrated to dryness. The residue was dissolved in EtOAc, brine and water and extracted with EtOAc (3×). The combined organic extracts were washed with sat. aqueous $NaHCO_3$ and brine, and dried over anhydrous magnesium sulfate. After filtration and evaporation, the residue was triturated with ethyl ether to give the title material as a first crop (150 mgs, 52%). LC (Method B): 2.022 min, LCMS (APCI) calcd for $C_9H_9N_2OS$ $[M+H]^+$ m/z 193.04. found 193.2. $^1$H NMR ($CDCl_3$, 400 MHz) δ ppm: 7.92-8.03 (m, 2H), 7.44-7.59 (m, 3H), 5.14 (br. d, J=3.90 Hz, 2H), 2.63 (br. s., 1H).

Example 8

2-Methoxy-6-(6-methoxy-4-((5-phenyl-1,3,4-thiadiazol-2-yl)methoxy)benzofuran-2-yl)imidazo[2,1-b][1,3,4]thiadiazole

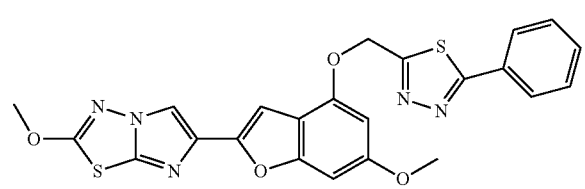 [SMILES: COc1cc(OCc2nnc(-c3ccccc3)s2)c2cc(-c3cn4nc(OC)sc4n3)oc2c1]

In a 200 mL round-bottomed flask, benzene was added to ethyl 5-phenyl-1,3,4-thiadiazole-2-carboxylate (Example 8B, 80 mgs, 0.252 mmol) and 6-methoxy-2-(2-methoxyimidazo[2,1-b][1,3,4]thiadiazol-6-yl)benzofuran-4-ol (Example 1H, 58.2 mgs, 0.303 mmol) and the mixture was sonificated for 30 sec. and concentrated in vacuo to remove traces of water in the starting material. Triphenylphosphine (99 mgs, 0.378 mmol) was added and the mixture was dried on high vacuum for 10 min. THF (40 mL) were added and the mixture was sonificated/heated for 5 min. Diisopropyl azodicarboxylate (68.6 µl, 0.353 mmol) in THF (4 mL) was added dropwise on app. 1 h and LC/MS showed that the reaction was not complete. Diisopropyl azodicarboxylate (2 drops) were added again and the mixture was diluted in $CH_2Cl_2$, washed with sat. aqueous $NaHCO_3$ (1×), brine (1×), and dried over anhydrous $MgSO_4$ and concentrated. The residue was purified on silica gel chromatography (100% $CH_2Cl_2$ up to 15% EtOAc/$CH_2Cl_2$) to give a residue which was triturated with MeCN and afforded the title material (36 mgs, 29%). LC (Method A): 2.901 min. HRMS (ESI) calcd for $C_{23}H_{17}N_5O_4S_2$ $[M+H]^+$ m/z 492.0722. found 492.0806. $^1$H NMR ($CDCl_3$, 400 MHz) δ ppm: 7.96-8.02 (m, 2H), 7.87 (s, 1H), 7.45-7.55 (m, 3H), 7.10 (s, 1H), 6.73-6.78 (m, 1H), 6.48 (d, J=1.57 Hz, 1H), 5.63 (s, 2H), 4.22 (s, 3H), 3.86 (s, 3H).

Example 9

2-Methoxy-6-(6-methoxy-4-((1-phenyl-1H-1,2,3-triazol-4-yl)methoxy)benzofuran-2-yl)imidazo[2,1-b][1,3,4]thiadiazole

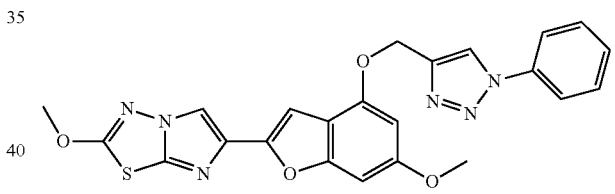

9A. 2-Methoxy-6-(6-methoxy-4-(prop-2-yn-1-yloxy)benzofuran-2-yl)imidazo[2,1-b][1,3,4]thiadiazole

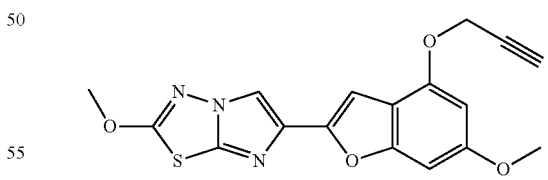

A solution of 6-methoxy-2-(2-methoxyimidazo[2,1-b][1,3,4]thiadiazol-6-yl)benzofuran-4-ol (Example 1H, 205 mgs, 0.646 mmol) in THF (10 mL) was treated at r.t. and under a nitrogen atmosphere, with propargyl alcohol (0.096 mL, 1.615 mmol), tri-n-butylphosphine (0.398 mL, 1.615 mmol) and dropwise, over a 25 min period with a solution of 1,1'-(azodicarbonyl)dipiperidine (408 mgs, 1.615 mmol) in THF (10 mL). The mixture was sonicated in a bath for 30 min and stirred at r.t. for another 30 min. The mixture was then dissolved in dichloromethane (50 mL) and washed with sat. aqueous NaHCO₃, brine and dried (MgSO₄). Evaporation of the solvent gave a solid that was purified by silica gel column chromatography ISCO to give the title material (180 mg, 0.507 mmol, 78% yield). ¹H NMR (DMSO-d₆, 400 MHz) δ ppm: 8.38 (s, 1H), 6.92 (s, 1H), 6.86 (dd, J=1.8, 1.0 Hz, 1H), 6.53 (d, J=1.6 Hz, 1H), 4.94 (d, J=2.7 Hz, 2H), 4.21 (s, 3H), 3.77-3.84 (m, 3H), 3.60-3.66 (m, 1H).

9B. Azidobenzene

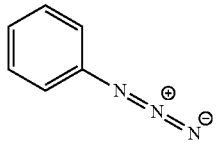

A solution of aniline (500 mgs, 5.37 mmol) in acetonitrile (10 mL, 191 mmol) was cooled down in an ice bath and treated with tert-butyl nitrite (680 mgs, 6.59 mmol) and dropwise with TMS-N3 (0.713 mL, 5.37 mmol). The ice bath was removed and the mixture was stirred overnight at r.t. under N2. Acetonitrile was carefully evaporated (NB: azidobenzene is also volatile) and the residue (750 mgs) was passed through a silica gel pad (20 g) and eluted with petroleum ether (35-55° C.). Evaporation of the solvent gave the title material as an oil (500 mgs, 4.20 mmol, 78% yield) that still contains some traces of solvent as shown by ¹H NMR. ¹H NMR (CDCl₃, 400 MHz) δ ppm: 7.32-7.41 (m, 2H), 7.12-7.19 (m, 1H), 7.01-7.09 (m, 2H).

Example 9

2-Methoxy-6-(6-methoxy-4-((1-phenyl-1H-1,2,3-triazol-4-yl)methoxy)benzofuran-2-yl)imidazo[2,1-b][1,3,4]thiadiazole

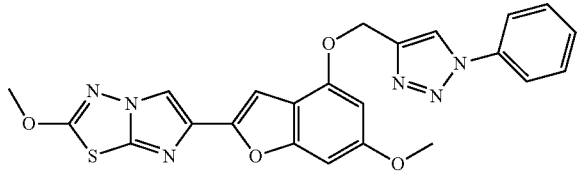 [SMILES: COc1cc(OCc2cn(-c3ccccc3)nn2)c2cc(-c3cn4nc(OC)sc4n3)oc2c1]

A solution of 2-methoxy-6-(6-methoxy-4-(prop-2-yn-1-yloxy)benzofuran-2-yl)imidazo[2,1-b][1,3,4]thiadiazole (Example 9A, 20 mgs, 0.056 mmol) and azidobenzene (Example 9B, 19 mgs, 0.159 mmol) in DMF (4 mL, 51.7 mmol) was treated at r.t. and under a nitrogen atmosphere with sodium (R)-2-((S)-1,2-dihydroxyethyl)-4-hydroxy-5-oxo-2,5-dihydrofuran-3-olate (8 mgs, 0.040 mmol) and copper(II) sulfate pentahydrate (5 mgs, 0.020 mmol). The mixture was stirred for 2 hours (reaction followed by HPLC) and was then diluted with dichloromethane (60 mL) and washed with sat. NaHCO₃, brine and dried (MgSO₄). The solvent was evaporated and the solid residue was triturated with acetonitrile (2×1 mL) and lyophilized to give the title material (13 mgs, 0.027 mmol, 49% yield). LC (Method A): 2.213 min. HRMS (ESI) calcd for C₂₃H₁₉N₆O₄S [M+H]⁺ m/z 475.1183. found 475.1204. ¹H NMR (DMSO-d₆, 400 MHz) δ ppm: 9.04 (s, 1H), 8.37 (s, 1H), 7.90-7.99 (m, 2H), 7.58-7.67 (m, 2H), 7.51 (tt, J=7.4, 1.2 Hz, 1H), 6.97-7.03 (m, 1H), 6.83-6.88 (m, 1H), 6.71 (d, J=1.6 Hz, 1H), 5.38 (s, 3H), 4.20 (s, 3H), 3.83 (s, 3H).

Example 10

2-Methoxy-6-(6-methoxy-4-((1-phenyl-1H-1,2,3-triazol-5-yl)methoxy)benzofuran-2-yl)imidazo[2,1-b][1,3,4]thiadiazole

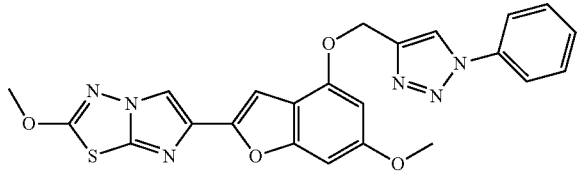 [SMILES: COc1cc(OCc2cn(-c3ccccc3)nn2)c2cc(-c3cn4nc(OC)sc4n3)oc2c1]

In a 5 mL microwave vial, was added 2-methoxy-6-(6-methoxy-4-(prop-2-yn-1-yloxy)benzofuran-2-yl)imidazo[2,1-b][1,3,4]thiadiazole (Example 9A, 27 mgs, 0.076 mmol), azidobenzene (Example 9B, 30 mgs, 0.252 mmol), anhydrous DMF (2.5 mL, 32.3 mmol) and (Cp*RuCl)₄ (12 mgs) under a nitrogen atmosphere. The vial was capped and heated at 110° C. for 20 min. in the microwave apparatus. The solvent was evaporated and the residue was purified by silica gel chromatography ISCO, concentrated and twice triturated with methanol (2×1 mL). To the solid was added acetonitrile (2 mL) and water (4 mL) and the mixture was freeze dried over the weekend to give the title material (5 mgs, 10.54 μmol, 14% yield). LC (Method F): 2.480 min. HRMS (ESI) calcd for C₂₃H₁₉N₆O₄S [M+H]⁺ m/z 475.1183. found 475.1234. ¹H NMR (DMSO-d₆, 400 MHz) δ ppm: 8.35 (s, 1H), 8.12 (s, 1H), 7.66-7.73 (m, 2H), 7.53-7.63 (m, 3H), 6.84 (dd, 0.8 Hz, 1H), 6.75 (d, J=0.8 Hz, 1H), 5.40 (s, 2H), 4.20 (s, 3H), 3.79 (s, 3H).

Preparation of Alcohols

The following alcohols were prepared according to the procedures described in Examples 3 to 8.

| Structure | Formula | Calc. [M + H]⁺ m/z | Calc. [M + H]⁺⁻ H₂O m/z | LCMS [M + H]⁺ m/z | LCMS [M + H]⁺⁻ H₂O m/z | HPLC Retention Time (Min)/Method | NMR |
|---|---|---|---|---|---|---|---|
| 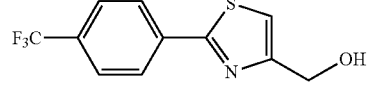 | C₁₁H₈F₃NOS | 260.04 | 242.04 | 260.00 | 242.00 | 1.943/A | ¹H NMR (CDCl₃) δ ppm: 8.07 (d, J = 8.2 Hz, 2H) 7.71 (d, J = 8.2 Hz, 2H) 7.28 (s, 1H) 4.87 (d, J = 5.5 Hz, 2H) 2.31 (t, J = 5.5 Hz, 1H) |

| Structure | Formula | Calc. [M + H]+ m/z | Calc. [M + H]+− H2O m/z | LCMS [M + H]+ m/z | LCMS [M + H]+− H2O m/z | HPLC Retention Time (Min)/Method | NMR |
|---|---|---|---|---|---|---|---|
| 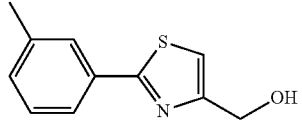 | C$_{11}$H$_{11}$NOS | 206.0634 | 189.06 | 206.1 | 188.1 | 1.842/A | $^1$H NMR (CDCl$_3$) δ ppm: 7.78 (s, 1H) 7.70-7.75 (m, 1H) 7.30-7.36 (m, 1H) 7.23-7.27 (m, 1H) 7.16-7.19 (m, 1H) 4.84 (d, J = 5.5 Hz, 2H) 2.53 (t, J = 6.1 Hz, 1H) 2.42 (s, 3H) |
| 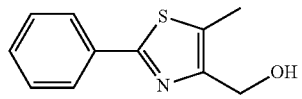 | C$_{11}$H$_{11}$NOS | 206.0634 | | 206.0674 | | 1.616/C | $^1$H NMR (400 MHz, CDCl$_3$) δ ppm: 2.07 (t, J = 5.1 Hz, 1H) 2.46 (s, 3H) 4.83 (d, J = 5.1 Hz, 2H) 7.34-7.51 (m, 3H) 7.80-8.01 (m, 2H) |
| 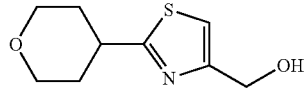 | C$_9$H$_{13}$NO$_2$S | 200.074 | | 200.077 | | 1.139/C | $^1$H NMR (400 MHz, CDCl$_3$) δ ppm: 1.75-1.99 (m, 2H) 1.99-2.15 (m, 2H) 2.27-2.45 (m, 1H) 3.11-3.34 (m, 1H) 3.55 (td, J = 11.74, 1.96 Hz, 2H) 4.08 (ddd, J = 11.74, 4.11, 1.37 Hz, 2H) 4.76 (d, J = 5.87 Hz, 2H) 7.09 (d, J = 0.78 Hz, 1H) |
| 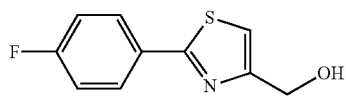 [SMILES: OCc1csc(-c2ccc(F)cc2)n1] | C$_{10}$H$_8$FNOS | 210.04 | 192.03 | 210 | | 1.607/A | $^1$H NMR (400 MHz, CDCl$_3$) δ ppm: 7.88-7.97 (m, 2H), 7.71 (t, J = 1.0 Hz, 1H), 7.10-7.18 (m, 2H), 4.91 (dd, J = 6.1, 1.0 Hz, 2H), 1.92 (t, J = 6.1 Hz, 1H) |
| 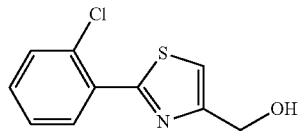 [SMILES: OCc1csc(-c2ccccc2Cl)n1] | C$_{10}$H$_8$ClNOS | | | | | 1.819/A | $^1$H NMR (400 MHz, CDCl$_3$) δ ppm: $^1$H NMR (400 MHz, CDCl$_3$) δ ppm: 8.15-8.2 (m, 1H), 7.45-7.5 (m, 1H), 7.3-7.41 (m, 3H), 4.85 (d, J = 5.9 Hz, 2H), 2.33 (t, J = 5.9 Hz, 1H) |
| 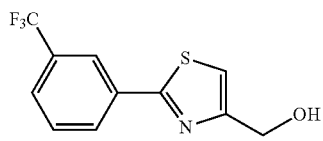 [SMILES: OCc1csc(-c2cccc(C(F)(F)F)c2)n1] | C$_{11}$H$_8$F$_3$NOS | 260.0351 | | 260.0362 | | 1.987/A | $^1$H NMR (400 MHz, CDCl$_3$) δ ppm: 8.19 (s, 1H), 8.07 (d, J = 7.5 Hz, 1H), 7.65 (d, J = 7.9 Hz, 1H), 7.54 (broad t, 1H), 7.24 (s, 1H), 4.83 (s, 2H), 2.58 (broad s, 1H) |
| 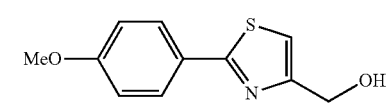 | C$_{11}$H$_{11}$NO$_2$S | 222.0583 | | 222.0591 | | 1.712/A | $^1$H NMR (400 MHz, CDCl$_3$) δ ppm: 7.86 (d, J = 8.8 Hz, 2H), 7.08 (s, 1H), 6.93 (d, J = 8.8 Hz, 2H), 4.79 (d, J = 6.1 Hz, 2H), 3.84 (s, 3H), 2.31 (t, J = 6.1 Hz, 1H) |

-continued

| Structure | Formula | Calc. [M + H]+ m/z | Calc. [M + H]+− H2O m/z | LCMS [M + H]+ m/z | LCMS [M + H]+− H2O m/z | HPLC Retention Time (Min)/Method | NMR |
|---|---|---|---|---|---|---|---|
| 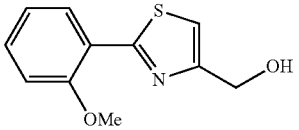 [SMILES: COc1ccccc1-c1nc(CO)cs1] | C11H11NO2S | 222.0583 | | 222.0598 | | 1.659/A | 1H NMR (400 MHz, CDCl3) δ ppm: 8.36 (dd, J = 8.8, 1.45 Hz, 1H), 7.35-7.40 (m, 1H), 7.21 (s, 1H), 7.06 (t, J = 7.8 Hz, 1H), 7.02 (d, J = 8.3 Hz, 1H), 4.83 (d, J = 5.9 Hz, 2H), 4.01 (s, 3H), 2.34 (t, J = 5.9 Hz, 1H). |
| 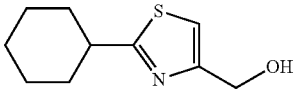 | C10H15NOS | 198.0947 | | 198.0956 | | 1.829/F | 1H NMR (400 MHz, CDCl3) δ ppm: 7.01 (s, 1H), 4.72 (broad s, 2H), 2.91-3.0 (m, 1H), 2.56 (broad s, 1H), 2.08-2.13 (m, 2H), 1.72-1.85 (m, 2H), 1.7-1.72 (m, 1H), 1.14-1.54 (m, 5H). |
| 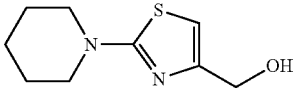 | C9H14N2OS | | | | | 1.188/F | 1H NMR (400 MHz, CDCl3) δ ppm: 6.34 (s, 1H), 4.51 (d, J = 5.8 Hz, 2H), 3.41-3.44 (m, 4H), 2.17 (t, J = 5.8 Hz, 1H), 1.59-1.68 (m, 6H). |
| 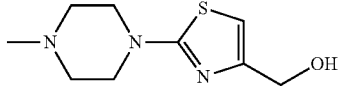 | C9H15N3OS | 214.1009 | | 214.1012 | | 0.534/F | 1H NMR (400 MHz, CDCl3) δ ppm: 6.40 (s, 1H), 4.52 (s, 2H), 3.48 (t, J = 5.2 Hz, 4H), 2.50 (t, J = 5.2 Hz, 4H), 2.33 (s, 3H), 1.75 (broad s, 1H). |
| 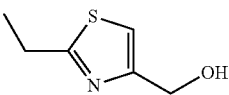 | C6H9NOS | 144.0478 | | 144.0502 | | 0.803/C | 1H NMR (400 MHz, CDCl3) δ ppm: 1.39 (t, J = 7.63 Hz, 3H) 2.90-3.15 (m, 3H) 4.74 (d, J = 5.87 Hz, 2H) 7.04 (s, 1H) |
| 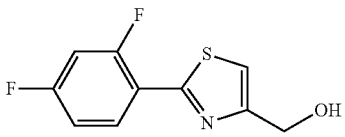 [SMILES: OCc1csc(-c2ccc(F)cc2F)n1] | C10H7F2NOS | 228.03 | 210.02 | 228 | 210 | | 1H NMR (400 MHz, CDCl3) δ ppm: 8.29 (td, J = 8.7, 6.5 Hz, 1H), 7.29-7.33 (m, 1H), 6.92-7.05 (m, 2H), 4.86 (d, J = 6.0 Hz, 2H), 2.32 (t, J = 6.1Hz, 1H) |
| 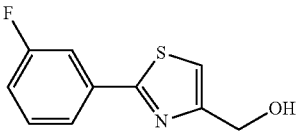 [SMILES: OCc1csc(-c2cccc(F)c2)n1] | C10H8FNOS | 210.04 | 192.03 | 210 | 192 | 1.738/A | 1H NMR (400 MHz, CDCl3) δ ppm: 7.65-7.74 (m, 2H), 7.41 (td, J = 7.9, 5.7 Hz, 1H), 7.23 (s, 1H), 7.13 (td, J = 8.4, 2.7 Hz, 1H), 4.84 (d, J = 5.9 Hz, 2H), 2.42 (t, J = 5.9 Hz, 1H) |
| 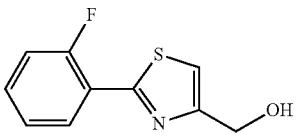 | C10H8FNOS | 210.04 | 192.03 | 210 | 192 | 1.741/A | 1H NMR (400 MHz, CDCl3) δ ppm: 8.21 (td, J = 7.7, 1.8 Hz, 1H), 7.31-7.40 (m, 1H), 7.27 (s, 1H), 7.11-7.24 (m, 2H), 4.82 (d, J = 6.0 Hz, 2H), 2.86 (t, J = 6.1 Hz, 1H) |

-continued

| Structure | Formula | Calc. [M + H]+ m/z | Calc. [M + H]+− $H_2O$ m/z | LCMS [M + H]+ m/z | LCMS [M + H]+− $H_2O$ m/z | HPLC Retention Time (Min)/Method | NMR |
|---|---|---|---|---|---|---|---|
| 4-Cl-phenyl thiazole methanol | $C_{10}H_8ClNOS$ | 226.01 | 208.00 | 226 | 208 | 1.902/A | $^1$H NMR (400 MHz, CDCl$_3$) δ ppm: 7.87-7.91 (m, 2H), 7.39-7.45 (m, 2H), 7.21 (t, J = 1.0 Hz, 1H), 4.84 (d, J = 5.7 Hz, 2H), 2.31 (t, J = 5.7 Hz, 1H) |
| 4-pyridyl thiazole methanol | $C_9H_8N_2OS$ | 193.04 | 175.03 | 193 | 175 | 1.248/B | $^1$H NMR (400 MHz, CDCl$_3$) δ ppm: 8.71 (d, J = 6.2Hz, 2H), 7.81 (d, J = 6.2Hz, 2H), 7.35 (s, 1H), 4.88 (d, J = 3.9 Hz, 2H), 2.45 (br. s., 1H) |
| 4-OCF3-phenyl thiazole methanol | $C_{11}H_8F_3NO_2S$ | 276.03 | 258.02 | 276 | 258 | 2.020/A | $^1$H NMR (400 MHz, CDCl$_3$) δ ppm: 7.98 (dd, J = 8.1, 4.8 Hz, 2H), 7.29 (d, J = 8.1 Hz, 2H), 7.22 (s, 1H), 4.84 (d, J = 5.5 Hz, 2H), 2.47 (t, J = 5.5 Hz, 1H) |
| 3-pyridyl thiazole methanol | $C_9H_8N_2OS$ | 193.04 | 175.03 | 193 | | 1.152/A | $^1$H NMR (400 MHz, CDCl$_3$) δ ppm: 9.11 (d, J = 2.0 Hz, 1H), 8.66 (dd, J = 4.9, 1.4 Hz, 1H), 8.28 (dt, J = 8.2, 2.0 Hz, 1H), 7.58 (s, 1H), 7.53 (dd, J = 7.8, 4.7 Hz, 1H), 5.44 (t, J = 5.8 Hz, 1H), 4.65 (d, J = 5.9 Hz, 2H) |
| 4,4-difluoropiperidinyl thiazole methanol | $C_9H_{12}F_2N_2OS$ | 235.07 | 217.06 | 235 | 217 | 1.293/A | $^1$H NMR (400 MHz, CDCl$_3$) δ ppm: 6.46 (s, 1H), 4.55 (br. s., 2H), 3.66 (dd, J = 6.0 Hz, 4H), 2.17 (br. s., 1H), 2.02-2.15 (m, 4H) |
| pyrazinyl thiazole methanol | $C_8H_7N_3OS$ | 194.04 | 176.03 | 194 | 176 | 1.577/B | $^1$H NMR (400 MHz, CDCl$_3$) δ ppm: 9.43 (br. d, J = 1.60 Hz, 1H), 8.62 (d, J = 2.74 Hz, 1H), 8.56-8.60 (m, 1H), 7.40 (s, 1H), 4.89 (d, J = 5.87 Hz, 2H), 2.24 (t, J = 6.06 Hz, 1H) |
| 2-bromo thiazole methanol | $C_4H_4BrNOS$ | 193.93 | 175.92 | | 176 | 1.101/A | $^1$H NMR (400 MHz, CDCl$_3$) δ ppm: 7.18 (d, J = 0.78 Hz, 1H), 4.76 (d, J = 1.00 Hz, 2H), 2.28-2.71 (m, 1H) |
| 5-methylisoxazolyl thiazole methanol | $C_8H_8N_2O_2S$ | 197.04 | 179.03 | 197 | 179 | 1.689/B | $^1$H NMR (400 MHz, CDCl$_3$) δ ppm: 7.32 (s, 1H), 6.57 (br. d, J = 0.80 Hz, 1H), 4.86 (s, 2H), 2.52 (d, J = 0.78 Hz, 3H) |

Preparation of Bromides

The following bromides were prepared according to the procedure described in Example 4.

| Structure | Formula | Calc. [M + H]+ m/z | LCMS [M + H]+ m/z | HPLC Retention Time (Min)/Method | NMR |
|---|---|---|---|---|---|
| 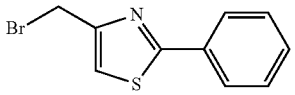 | C₁₀H₈BrNS | 253.9634 | 253.9654 | 2.10/A | ¹H NMR (400 MHz, CDCl₃) δ ppm: 4.65 (s, 2H), 7.31 (s, 1H), 7.42-7.49 (m, 3H), 7.93-8.00 (m, 2H) |
| 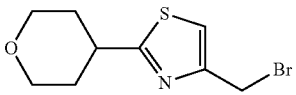 [SMILES: BrCc1csc(C2CCOCC2)n1] | C₉H₁₂BrNOS | 261.9896 | 261.9903 | 1.535/A | ¹H NMR (400 MHz, CDCl₃) δ ppm: 1.79-1.99 (m, 2H) 1.99-2.13 (m, 2H) 3.27 (tt, J = 11.69, 3.96 Hz, 1H) 3.54 (td, J = 11.74, 1.96 Hz, 2H) 4.00-4.17 (m, 2H) 4.57 (s, 2H) 7.21 (s, 1H) |
| 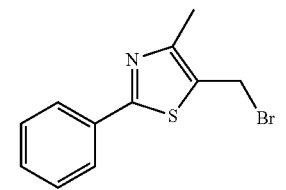 | C₁₁H₁₀BrNS | | | decomposed | ¹H NMR (400 MHz, CDCl₃) δ ppm: 2.47 (s, 3H) 4.74 (s, 2H) 7.40-7.47 (m, 3H) 7.87-7.94 (m, 2H) |
| 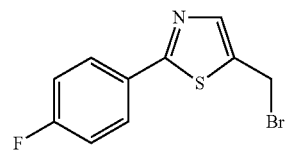 [SMILES: Fc1ccc(-c2ncc(CBr)s2)cc1] | C₁₀H₇BrFNS | 271.9539 | 271.9543 | 2.165/A | ¹H NMR (400 MHz, CDCl₃) δ ppm: 7.88-7.97 (m, 2H), 7.78 (s, 1H), 7.09-7.19 (m, 2H), 4.76 (s, 2H). |
| 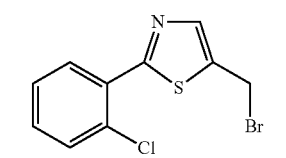 [SMILES: Clc1ccccc1-c1ncc(CBr)s1] | C₁₀H₇BrClNS | | | | ¹H NMR (400 MHz, CDCl₃) δ ppm: 8.2-8.5 (m, 1H), 7.45-7.5 (m, 1H), 7.44 (s, 1H), 7.3-7.4 (m, 2H), 4.65 (s, 2H). |
| 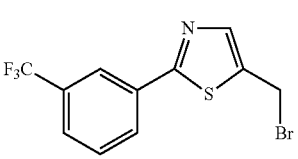 [SMILES: FC(F)(F)c1cccc(-c2ncc(CBr)s2)c1] | C₁₁H₇BrF₃NS | | | | ¹H NMR (400 MHz, CDCl₃) δ ppm: 8.20 (s, 1H), 8.10 (d, J = 7.8 Hz, 1H), 7.68 (d, J = 7.8 Hz, 1H), 7.56 (t, J = 7.8 Hz, 1H), 7.35 (s, 1H), 4.62 (s, 2H). |
| 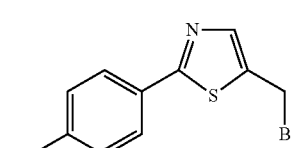 | C₁₁H₁₀BrNOS | | | | ¹H NMR (400 MHz, CDCl₃) δ ppm: 7.87 (d, J = 8.9 Hz, 2H), 7.21 (s, 1H), 6.93 (d, J = 8.9 Hz, 2H), 4.60 (s, 2H), 3.85 (s, 3H). |
| 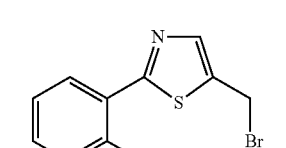 | C₁₁H₁₀BrNOS | | | | ¹H NMR (400 MHz, CDCl₃) δ ppm: 8.39 (dd, J = 7.8, 2.0 Hz, 1H), 7.36-7.41 (m, 1H), 7.34 (s, 1H), 7.05-7.09 (m, 1H), 7.01 (d, J = 8.16 Hz, 1H), 4.65 (s, 2H), 4.0 (s, 3H). |
| 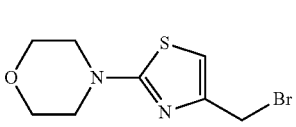 | C₈H₁₁BrN₂OS | 262.9848 | 262.9864 | 1.625/F | ¹H NMR (400 MHz, CDCl₃) δ ppm: 6.52 (s, 1H) 4.32 (s, 2H), 3.74 (t, J = 5.05 Hz, 4H), 3.40 (t, J = 5.05 Hz, 4H). |

-continued

| Structure | Formula | Calc. [M + H]+ m/z | LCMS [M + H]+ m/z | HPLC Retention Time (Min)/Method | NMR |
|---|---|---|---|---|---|
| 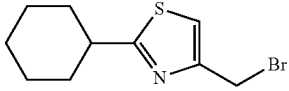 [SMILES: BrCc1csc(C2CCCCC2)n1] | C10H14BrNS | 260.0103 | 260.0127 | 2.184/F | 1H NMR (400 MHz, CDCl3) δ ppm: 7.13 (s, 1H), 4.54 (s, 2H), 2.94-3.03 (m, 1H), 2.10-2.14 (m, 2H), 1.80-1.86 (m, 2H), 1.69-1.75 (m, 1H), 1.2-1.54 (m, 5H). |
| 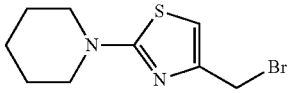 | C9H13BrN2S | 261.0056 | 261.0067 | 1.604/F | 1H NMR (400 MHz, CDCl3) δ ppm: 6.49 (s, 1H), 4.36 (s, 2H), 3.42-3.45 (m, 4H), 1.59-1.69 (m, 6H). |
| 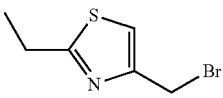 | C6H8BrNS | 205.96 207.96 | 206 208 | 1.748/F | 1H NMR (400 MHz, CDCl3) δ ppm: 7.17 (s, 1H), 4.56 (s, 2H), 3.04 (q, J = 7.4 Hz, 2H), 1.28-1.49 (m, 3H) |
| 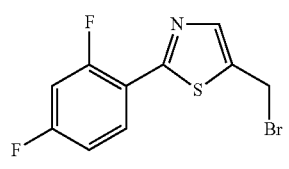 [SMILES: Fc1ccc(-c2ncc(CBr)s2)c(F)c1] | C10H6BrF2NS | 289.94 291.94 | 290 292 | 2.134/A | 1H NMR (400 MHz, CDCl3) δ ppm: 8.33 (td, J = 8.7, 6.5 Hz, 1H), 7.42 (s, 1H), 6.91-7.05 (m, 2H), 4.66 (d, J = 0.8 Hz, 2H) |
| 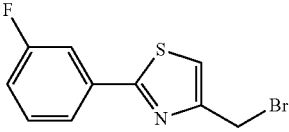 [SMILES: Fc1cccc(-c2nc(CBr)cs2)c1] | C10H7BrFNS | 271.95 273.95 | 272 274 | 1.986/A | 1H NMR (400 MHz, CDCl3) δ ppm: 7.67-7.75 (m, 2H), 7.38-7.46 (m, 1H), 7.34 (s, 1H), 7.11-7.18 (m, 1H), 4.64 (s, 2H) |
| 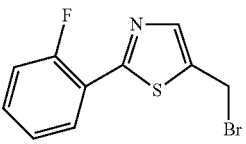 [SMILES: Fc1ccccc1-c1ncc(CBr)s1] | C10H7BrFNS | 271.95 273.95 | 272 274 | 2.082/A | 1H NMR (400 MHz, CDCl3) δ ppm: 8.28-8.36 (m, 1H), 7.38-7.47 (m, 2H), 7.24-7.30 (m, 2H), 7.20 (dd, J = 11.3, 8.2 Hz, 1H), 4.67 (s, 2H) |
| 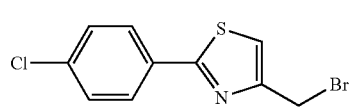 | C10H7BrClNS | 287.92 289.92 | 288 290 | 2.223/F | 1H NMR (400 MHz, CDCl3) δ ppm: 7.90 (d, J = 8.0 Hz, 2H), 7.43 (d, J = 8.0 Hz, 2H), 7.32 (s, 1H), 4.63 (s, 2H) |
| 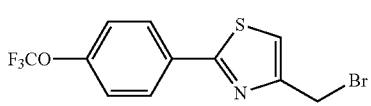 | C11H7BrF3NOS | 337.95 339.94 | 338 340 | 2.251/A | 1H NMR (400 MHz, CDCl3) δ ppm: 8.00 (dd, J = 9.0, 1.0 Hz, 2H), 7.33 (s, 1H), 7.30 (dd, J = 9.0, 1.0 Hz, 2H), 4.64 (s, 2H) |
| 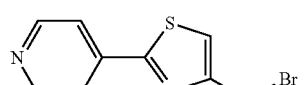 | C9H7BrN2S | 254.96 256.96 | 255 257 | 1.828/B | |
| 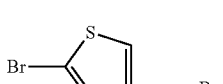 | C4H3Br2NS | 255.84 257.84 | 256 258 | 1.813/B | |

Examples 11 to 35

The following additional Examples have been prepared, isolated and characterized using the methods disclosed above.

| Ex. | Structure | Formula | Calc. [M + H]⁺ m/z | HPLC Retention Time (Min)/Method | LCMS [M + H]⁺ m/z | NMR |
|---|---|---|---|---|---|---|
| 11 | 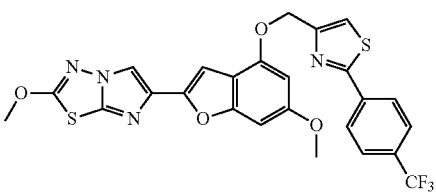 [SMILES: COc1cc(OCc2csc(-c3ccc(C(F)(F)F)cc3)n2)c2cc(-c3cn4nc(OC)sc4n3)oc2c1] | $C_{25}H_{17}F_3N_4O_4S_2$ | 559.0716 | 2.501/A | 559.0725 | ¹H NMR (CDCl₃) δ ppm: 8.10 (d, J = 8.2 Hz, 2H), 7.86 (s, 1H), 7.72 (d, J = 8.2 Hz, 2H), 7.44-7.48 (m, 1H), 7.12 (s, 1H), 6.71-6.75 (m, 1H), 6.48 (d, J = 1.6 Hz, 1H), 5.41 (d, J = 0.8 Hz, 2H), 4.22 (s, 3H), 3.86 (s, 3H) |
| 12 | 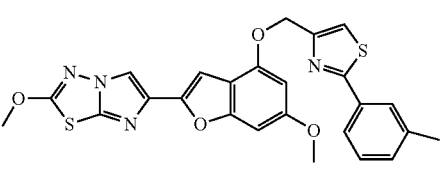 | $C_{25}H_{20}N_4O_4S_2$ | 505.0999 | 2.506/A | 505.1012 | ¹H NMR (CDCl₃) δ ppm: 8.10 (d, J = 8.2 Hz, 2H) 7.86 (s, 1H) 7.72 (d, J = 8.2 Hz, 2H) 7.44-7.48 (m, 1H) 7.12 (s, 1H) 6.71-6.75 (m, 1H) 6.48 (d, J = 1.6 Hz, 1H) 5.41 (d, J = 0.8 Hz, 2H) 4.22 (s, 3H) 3.86 (s, 3H) |
| 13 | 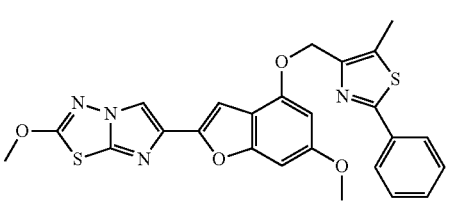 [SMILES: COc1cc(OCc2nc(-c3ccccc3)sc2C)c2cc(-c3cn4nc(OC)sc4n3)oc2c1] | $C_{25}H_{20}N_4O_4S_2$ | 505.0999 | 2.498/C | 505.1197 | ¹H NMR (400 MHz, CDCl₃) δ ppm: 2.53 (s, 3H) 3.87 (s, 3H) 4.21 (s, 3H) 5.31 (s, 2H) 6.44 (d, J = 1.56 Hz, 1H) 6.74 (broad d, 1H) 7.06 (s, 1H) 7.38-7.48 (m, 3H) 7.85 (s, 1H) 7.90-7.97 (m, 2H) |
| 14 | 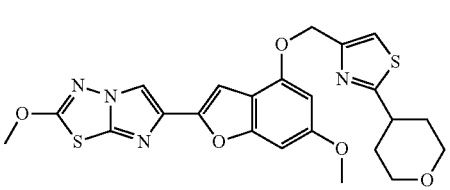 [SMILES: COc1cc(OCc2csc(C3CCOCC3)n2)c2cc(-c3cn4nc(OC)sc4n3)oc2c1] | $C_{23}H_{22}N_4O_5S_2$ | 499.1104 | 2.303/C | 499.1139 | ¹H NMR (400 MHz, CDCl₃) δ ppm: 1.82-2.02 (m, 2H) 2.02-2.20 (m, 2H) 3.21-3.35 (m, 1H) 3.56 (td, J = 11.74, 1.96 Hz, 2H) 3.85 (s, 3H) 4.05-4.13 (m, 2H) 4.22 (s, 3H) 5.31 (s, 2H) 6.44 (d, J = 1.96 Hz, 1H) 6.71 (d, J = 0.78 Hz, 1H) 7.09 (s, 1H) 7.85 (s, 1H) |
| 15 | 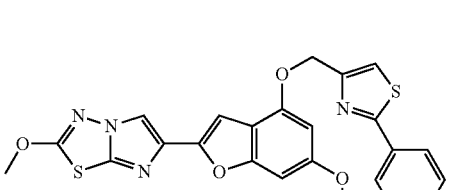 | $C_{24}H_{17}FN_4O_4S_2$ | 509.0748 | 2.637/B | 509.0769 | ¹H NMR (400 MHz, CDCl₃) δ ppm: 7.9-7.97 (m, 2H), 7.82 (s, 1H), 7.33 (s, 1H), 7.13-7.15 (m, 2H), 7.12 (s, 1H), 6.70 (d, J = 1.87 Hz, 1H), 6.44 (d, J = 1.87 Hz, 1H), 5.36 (s, 2H), 4.19 (s, 3H), 3.83 (s, 3H). |

-continued

| Ex. | Structure | Formula | Calc. [M + H]+ m/z | HPLC Retention Time (Min)/Method | LCMS [M + H]+ m/z | NMR |
|---|---|---|---|---|---|---|
| 16 | 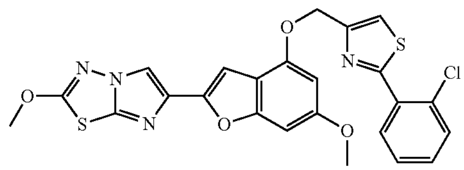 [SMILES: COc1cc(OCc2csc(-c3ccccc3Cl)n2)c2cc(-c3cn4nc(OC)sc4n3)oc2c1] | $C_{24}H_{17}ClN_4O_4S_2$ | 525.0453 | 2.502/A | 525.0458 | $^1$H NMR (400 MHz, CDCl$_3$) δ ppm: 8.2-8.25 (m, 1H), 7.83 (s, 1H), 7.52 (s, 1H), 7.48-7.50 (m, 1H), 7.31-7.39 (m, 2H), 7.10 (s, 1H), 6.70 (broad d, 1H), 6.46 (d, J = 1.88 Hz, 1H), 5.41 (s, 2H), 4.19 (s, 3H), 3.83 (s, 3H). |
| 17 | 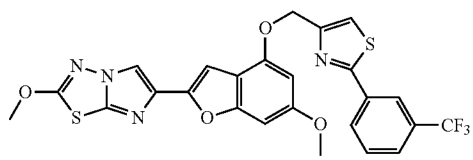 [SMILES: COc1cc(OCc2csc(-c3cccc(C(F)(F)F)c3)n2)c2cc(-c3cn4nc(OC)sc4n3)oc2c1] | $C_{25}H_{17}F_3N_4O_4S_2$ | 559.0716 | 2.534/A | 559.0752 | $^1$H NMR (400 MHz, CDCl$_3$) δ ppm: 8.23 (broad s, 1H), 8.12 (broad d, J = 7.9 Hz, 1H), 7.83 (s, 1H), 7.67 (broad d, J = 7.9 Hz, 1H), 7.57 (broad t, J = 7.9 Hz, 1H), 7.42 (s, 1H), 7.10 (s, 1H), 6.70 (broad d, 1H), 6.46 (d, J = 1.54 Hz, 1H), 5.39 (s, 2H), 4.19 (s, 3H), 3.83 (s, 3H). |
| 18 | 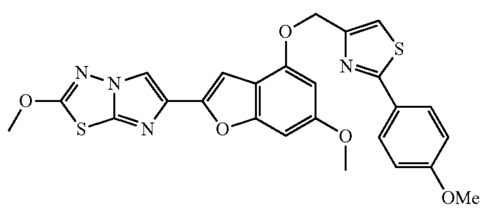 [SMILES: COc1ccc(-c2nc(COc3cc(OC)cc4oc(-c5cn6nc(OC)sc6n5)cc34)cs2)cc1] | $C_{25}H_{20}N_4O_5S_2$ | 521.0948 | 2.451/A | 521.0977 | $^1$H NMR (400 MHz, CDCl$_3$) δ ppm: 7.86-7.90 (m, 2H), 7.83 (s, 1H), 7.27 (s, 1H), 7.10 (s, 1H), 6.93-6.96 (m, 2H), 6.69 (broad d, 1H), 6.45 (d, J = 1.7 Hz, 1H), 5.36 (s, 2H), 4.19 (s, 3H), 3.85 (s, 3H), 3.83 (s, 3H). |
| 19 | 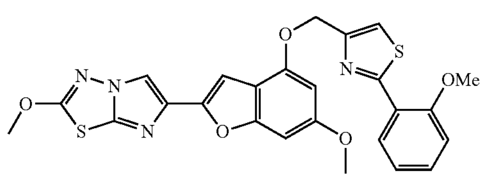 [SMILES: COc1cc(OCc2csc(-c3ccccc3OC)n2)c2cc(-c3cn4nc(OC)sc4n3)oc2c1] | $C_{25}H_{20}N_4O_5S_2$ | 521.0948 | 2.460/A | 521.0984 | $^1$H NMR (400 MHz, CDCl$_3$) δ ppm: 8.33 (dd, J = 7.84, 1.7 Hz, 1H), 7.77 (s, 1H), 7.35 (s, 1H), 7.29-7.34 (m, 1H), 7.05 (s, 1H), 6.95-7.04 (m, 2H), 6.62 (d, J = 2.0 Hz, 1H), 6.40 (d, J = 2.0 Hz, 1H), 5.34 (s, 2H), 4.12 (s, 3H), 3.96 (s, 3H), 3.76 (s, 3H). |
| 20 | 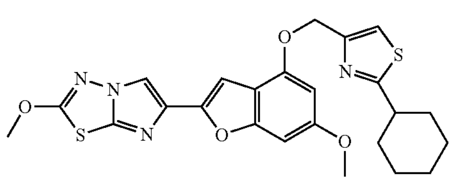 [SMILES: COc1cc(OCc2csc(C3CCCCC3)n2)c2cc(-c3cn4nc(OC)sc4n3)oc2c1] | $C_{24}H_{24}N_4O_4S_2$ | 497.1312 | 2.631/F | 497.1350 | $^1$H NMR (400 MHz, CDCl$_3$) δ ppm: 7.82 (s, 1H), 7.20 (s, 1H), 7.07 (s, 1H), 6.68 (broad d, 1H), 6.40 (d, J = 2.0 Hz, 1H), 5.27 (s, 2H), 4.19 (s, 3H), 3.82 (s, 3H), 2.95-3.03 (m, 1H), 2.13-2.16 (m, 2H), 1.82-1.87 (m, 2H), 1.7-1.75 (m, 1H), 1.12-1.58 (m, 5H). |

| Ex. | Structure | Formula | Calc. [M + H]+ m/z | HPLC Retention Time (Min)/Method | LCMS [M + H]+ m/z | NMR |
|---|---|---|---|---|---|---|
| 21 | 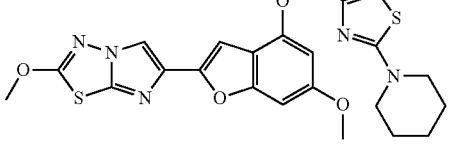 | C₂₃H₂₃N₅O₄S₂ | 498.1264 | 2.409/F | 498.1329 | ¹H NMR (400 MHz, CDCl₃) δ ppm: 7.82 (s, 1H), 7.08 (s, 1H), 6.68 (broad s, 1H), 6.53 (s, 1H), 6.41 (broad s, 1H), 5.09 (s, 2H), 4.18 (s, 3H), 3.82 (s, 3H), 3.43-3.46 (m, 4H), 1.60-1.68 (m, 6H). |
| 22 | 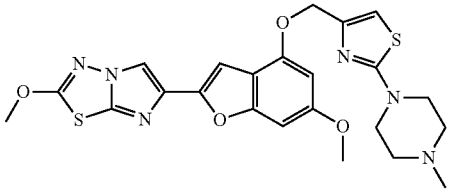 | C₂₃H₂₄N₆O₄S₂ | 513.1373 | 2.208/F | 513.1391 | ¹H NMR (400 MHz, CDCl₃) δ ppm: 7.85 (s, 1H), 7.10 (s, 1H), 6.70 (d, J = 0.8 Hz, 1H), 6.61 (s, 1H), 6.43 (d, J = 1.6 Hz, 1H), 5.12 (s, 2H), 4.21 (s, 3H), 3.84 (s, 3H), 3.53 (t, J = 1.0 Hz, 4H), 2.54 (t, J = 1.0 Hz, 4H), 2.36 (s, 3H). |
| 23 | 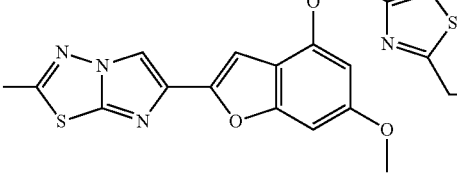 | C₂₀H₁₈N₄O₄S₂ | 443.0842 | 2.491/F | 443.0796 | ¹H NMR (400 MHz, CDCl₃) δ ppm: 7.85 (s, 1H), 7.23 (s, 1H), 7.09 (s, 1H), 6.71 (d, J = 0.8 Hz, 1H), 6.43 (d, J = 1.6 Hz, 1H), 5.30 (s, 2H), 4.21 (s, 3H), 3.85 (s, 3H), 3.07 (q, J = 7.4 Hz, 2H), 1.43 (t, J = 7.6 Hz, 3H) |
| 24 | 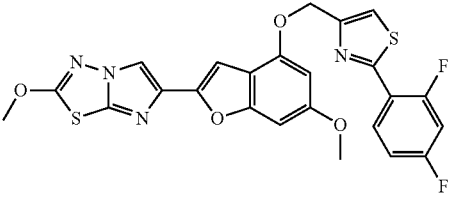 [SMILES: COc1cc(OCc2csc(-c3ccc(F)cc3F)n2)c2cc(-c3cn4nc(OC)sc4n3)oc2c1] | C₂₄H₁₆F₂N₄O₄S₂ | 527.0654 | 2.490/A | 527.0661 | ¹H NMR (400 MHz, CDCl₃) δ ppm: 8.33 (td, J = 8.6, 6.7 Hz, 1H), 7.86 (s, 1H), 7.49 (s, 1H), 7.12 (s, 1H), 6.93-7.06 (m, 2H), 6.72 (d, J = 1.6 Hz, 1H), 6.47 (d, J = 1.6 Hz, 1H), 5.41 (s, 2H), 4.22 (s, 3H), 3.85 (s, 3H) |
| 25 | 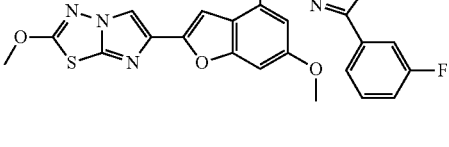 | C₂₄H₁₇FN₄O₄S₂ | 509.0748 | 2.475/A | 509.0757 | ¹H NMR (400 MHz, CDCl₃) δ ppm: 7.86 (s, 1H), 7.68-7.77 (m, 2H), 7.39-7.47 (m, 2H), 7.10-7.18 (m, 2H), 6.70-6.75 (m, 1H), 6.47 (d, J = 2.0 Hz, 1H), 5.40 (s, 2H), 4.21 (s, 3H), 3.85 (s, 3H) |

| Ex. | Structure | Formula | Calc. [M + H]+ m/z | HPLC Retention Time (Min)/Method | LCMS [M + H]+ m/z | NMR |
|---|---|---|---|---|---|---|
| 26 | 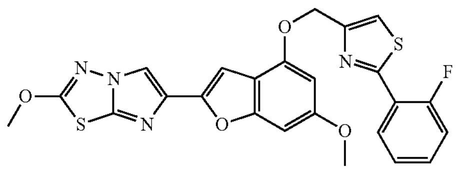 [SMILES: COc1cc(OCc2csc(-c3ccccc3F)n2)c2cc(-c3cn4nc(OC)sc4n3)oc2c1] | C$_{24}$H$_{17}$FN$_4$O$_4$S$_2$ | 509.0748 | 2.477/A | | $^1$H NMR (400 MHz, CDCl$_3$) δ ppm: 8.28-8.36 (m, 1H), 7.86 (s, 1H), 7.51 (s, 1H), 7.38-7.46 (m, 1H), 7.28-7.31 (m, 1H), 7.18-7.25 (m, 1H), 7.13 (s, 1H), 6.73 (dd, J = 2.0, 0.8 Hz, 1H), 6.48 (d, J = 2.0 Hz, 1H), 5.43 (s, 2H), 4.22 (s, 3H), 3.85 (s, 3H) |
| 27 | 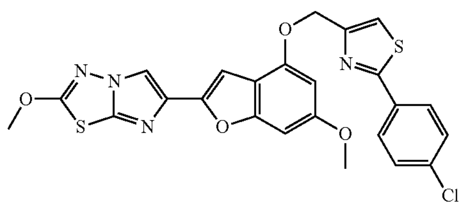 [SMILES: COc1cc(OCc2csc(-c3ccc(Cl)cc3)n2)c2cc(-c3cn4nc(OC)sc4n3)oc2c1] | C$_{24}$H$_{17}$ClN$_4$O$_4$S$_2$ | | 2.668/F | | $^1$H NMR (400 MHz, CDCl$_3$) δ ppm: 8.28-8.36 (m, 1H), 7.86 (s, 1H), 7.51 (s, 1H), 7.38-7.46 (m, 1H), 7.28-7.31 (m, 1H), 7.18-7.25 (m, 1H), 7.13 (s, 1H), 6.73 (dd, J = 2.0, 0.8 Hz, 1H), 6.48 (d, J = 2.0 Hz, 1H), 5.43 (s, 2H), 4.22 (s, 3H), 3.85 (s, 3H) |
| 28 | 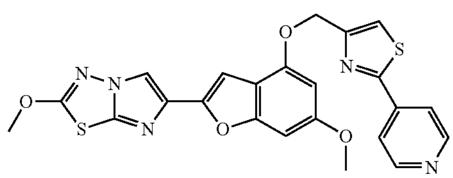 [SMILES: COc1cc(OCc2csc(-c3ccncc3)n2)c2cc(-c3cn4nc(OC)sc4n3)oc2c1] | C$_{23}$H$_{17}$N$_5$O$_4$S$_2$ | 492.0795 | 2.219/A | 492.0822 | $^1$H NMR (400 MHz, CDCl$_3$) δ ppm: 8.68-8.73 (m, 2H), 7.83 (s, 1H), 7.79-7.83 (m, 2H), 7.49 (s, 1H), 7.07-7.11 (m, 1H), 6.71 (d, J = 0.8 Hz, 1H), 6.44 (d, J = 2.0 Hz, 1H), 5.38-5.41 (m, 2H), 4.19 (s, 3H), 3.83 (s, 3H) |
| 29 | 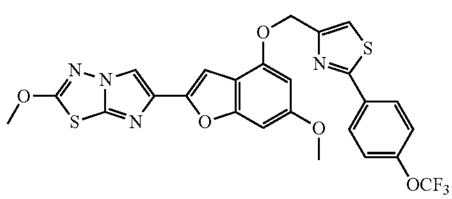 [SMILES: COc1cc(OCc2csc(-c3ccc(OC(F)(F)F)cc3)n2)c2cc(-c3cn4nc(OC)sc4n3)oc2c1] | C$_{25}$H$_{17}$F$_3$N$_4$O$_5$S$_2$ | 575.0665 | 2.549/A | 575.0691 | $^1$H NMR (400 MHz, CDCl$_3$) δ ppm: 8.01 (d, J = 8.6 Hz, 2H), 7.86 (s, 1H), 7.40 (d, J = 0.8 Hz, 1H), 7.31 (d, J = 8.6 Hz, 2H), 7.12 (s, 1H), 6.70-6.75 (m, 1H), 6.45-6.50 (m, 1H), 5.39 (s, 2H), 4.22 (s, 3H), 3.85 (s, 3H) |
| 30 | 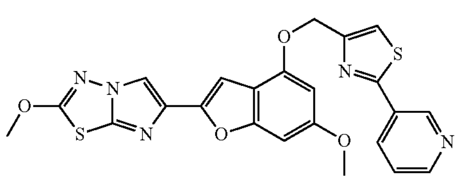 [SMILES: COc1cc(OCc2csc(-c3cccnc3)n2)c2cc(-c3cn4nc(OC)sc4n3)oc2c1] | C$_{23}$H$_{17}$N$_5$O$_4$S$_2$ | 492.0795 | 2.344/A | 492.0815 | $^1$H NMR (400 MHz, CDCl$_3$) δ ppm: 9.20 (d, J = 2.3 Hz, 1H), 8.68 (dd, J = 5.1, 1.6 Hz, 1H), 8.24-8.31 (m, 1H), 7.86 (s, 1H), 7.46 (s, 1H), 7.41 (dd, J = 7.8, 4.7 Hz, 1H), 7.12 (s, 1H), 6.71-6.76 (m, 1H), 6.48 (d, J = 2.0 Hz, 1H), 5.42 (s, 2H), 4.22 (s, 3H), 3.86 (s, 3H) |

| Ex. | Structure | Formula | Calc. [M + H]+ m/z | HPLC Retention Time (Min)/Method | LCMS [M + H]+ m/z | NMR |
|---|---|---|---|---|---|---|
| 31 | 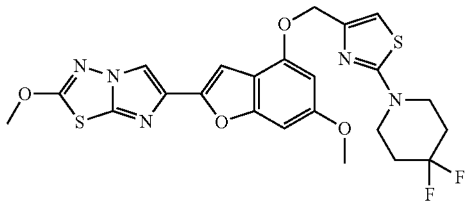 [SMILES: COc1cc(OCc2csc(N3CCC(F)(F)CC3)n2)c2cc(-c3cn4nc(OC)sc4n3)oc2c1] | C23H21F2N5O4S2 | 534.1076 | 2.428/A | 534.1097 | 1H NMR (400 MHz, CDCl3) δ ppm: 7.85 (s, 1H), 7.10 (s, 1H), 6.70 (d, J = 1.6 Hz, 1H), 6.64 (s, 1H), 6.44 (d, J = 1.6 Hz, 1H), 5.11 (s, 2H), 4.21 (s, 3H), 3.85 (s, 3H), 3.63-3.73 (m, 4H), 2.03-2.20 (m,4H) |
| 32 | 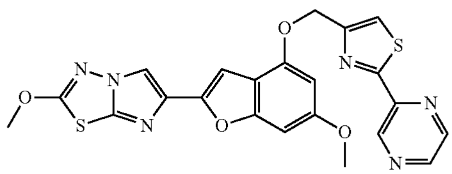 | C22H16N6O4S2 | 493.0747 | 2.371/A | 493.0750 | 1H NMR (400 MHz, CDCl3) δ ppm: 3.86 (s, 1H), 4.22 (s, 1H), 5.43 (s, 1H), 6.45-6.52 (m, 1H), 6.73 (s, 1H), 7.06-7.19 (m, 1H), 7.08-7.15 (m, 1H), 7.57 (s, 1H), 7.82-7.90 (m, 1H), 8.53-8.67 (m, 2H), 9.46 (s, 1H) |
| 33 | 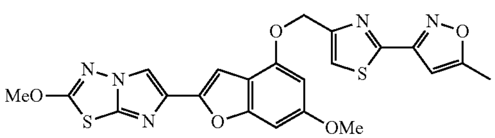 [SMILES: COc1cc(OCc2csc(-c3cc(C)on3)n2)c2cc(-c3cn4nc(OC)sc4n3)oc2c1] | C22H17N5O5S2 | 496.0744 | 2.330/A | 496.0757 | 1H NMR (400 MHz, CDCl3) δ ppm: 2.53 (d, J = 1.17 Hz, 3H), 3.85 (s, 3H), 4.22 (s, 3H), 5.40 (d, J = 0.78 Hz, 2H), 6.45 (d, J = 1.96 Hz, 1H), 6.56-6.63 (m, 1H), 6.73 (dd, J = 1.96, 0.78 Hz, 1H), 7.07-7.14 (m, 1H), 7.49 (t, J = 0.98 Hz, 1H), 7.86 (s, 1H) |
| 34 | 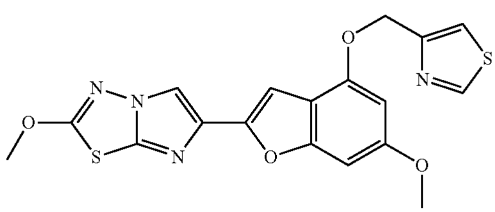 [SMILES: COc1cc(OCc2cscn2)c2cc(-c3cn4nc(OC)sc4n3)oc2c1] | C18H14N4O4S2 | 415.0529 | 2.193/A | 415.0546 | 1H NMR (400 MHz, CDCl3) δ ppm: 3.85 (s, 3H), 4.22 (s, 3H), 5.38-5.43 (m, 2H), 6.45 (d, J = 1.96 Hz, 1H), 6.70-6.74 (m, 1H), 7.10 (s, 1H), 7.40-7.49 (m, 1H), 7.85 (s, 1H), 8.85 (d, J = 1.96 Hz, 1H) |
| 35 | 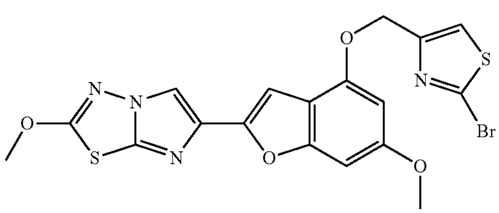 [SMILES: COc1cc(OCc2csc(Br)n2)c2cc(-c3cn4nc(OC)sc4n3)oc2c1] | C18H13BrN4O4S2 | 492.9635 494.9614 | 2.333/A | 494.9620 | 1H NMR (400 MHz, CDCl3) δ ppm: 3.85 (s, 3H), 4.19-4.25 (m, 3H), 5.30 (s, 2H), 6.40 (s, 1H), 6.72 (s, 1H), 7.08 (s, 1H), 7.30-7.38 (m, 1H), 7.86 (s, 1H) |

Example 36

6-(6-Fluoro-4-((2-phenylthiazol-4-yl)methoxy)benzofuran-2-yl)-2-methoxyimidazo[2,1-b][1,3,4]thiadiazole

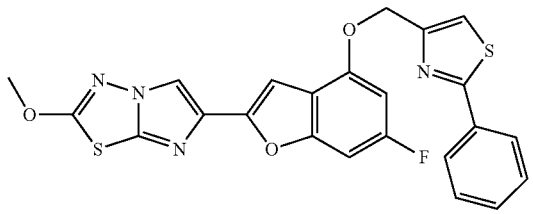 [SMILES: COc1nn2cc(-c3cc4c(OCc5csc(-c6ccccc6)n5)cc(F)cc4o3)nc2s1]

36A. 4-Fluoro-2-hydroxy-6-methoxybenzaldehyde and 2-fluoro-6-hydroxy-4-methoxybenzaldehyde

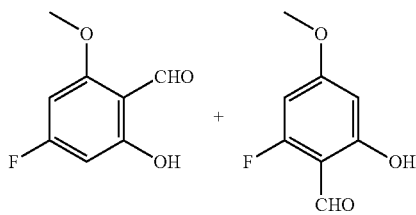

A 1:5 mixture of 4-fluoro-2,6-dimethoxybenzaldehyde and 2-fluoro-4,6-dimethoxybenzaldehyde (*Helvetica Chim. Acta*, 81:1596-1607 (1998), 1 g, 5.43 mmol) in 30 mL of dichloromethane was cooled down to 0-5° C. To this mixture was added dropwise over 25 minutes tribromoborane (7.33 mL, 7.33 mmol) in 10 mL of dichloromethane and the reaction was stirred at 0-5° C. for approx. 5-10 min. The mixture was then poured into ice, diluted down with dichloromethane and extracted twice with dichloromethane. The combined organic layers were dried over MgSO$_4$, filtered and concentrated. The residue was purified on ISCO silica gel column chromatography (40 g gold column using 90% hexanes and 10% dichloromethane up to 80% hexanes with 10% dichloromethane and 10% ethyl acetate). Both isomers were collected at the same time to give the title materials (720 mg, 78%) as a white crystalline solid.

2-Fluoro-6-hydroxy-4-methoxybenzaldehyde (major isomer, undesired)

$^1$H NMR (400 MHz, CDCl$_3$) δ ppm: 11.91 (s, 1H), 10.05 (s, 1H), 6.17-6.25 (m, 1H), 3.86 (s, 3H).

4-Fluoro-2-hydroxy-6-methoxybenzaldehyde (minor isomer, desired)

$^1$H NMR (400 MHz, CDCl$_3$) δ ppm: 12.23-12.42 (m, 1H), 10.22 (s, 1H), 6.23-6.27 (m, 1H), 6.13 (dd, J=10.96, 2.35 Hz, 1H), 3.90 (s, 3H).

36B. 1-(6-Fluoro-4-methoxybenzofuran-2-yl)ethanone

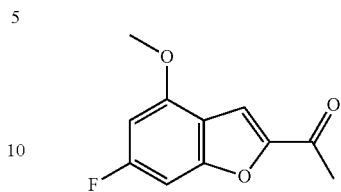

To a solution of a mixture of 4-fluoro-2-hydroxy-6-methoxybenzaldehyde and 2-fluoro-6-hydroxy-4-methoxybenzaldehyde (Example 36A, 4.63 g, 27.2 mmol) in acetonitrile (49.7 mL, 952 mmol) was added potassium iodide (0.903 g, 5.44 mmol), cesium carbonate (9.75 g, 29.9 mmol) and 1-chloropropan-2-one (2.395 mL, 28.6 mmol). The mixture was stirred at r.t. for 2 h, was treated with 0.1 eq of cesium carbonate and heated to 60° C. for 1 h and 80° C. for another hour. The reaction was left overnight at r.t., then filtered over a small pad of silica and rinsed with ethyl acetate (approx 500 mL). The residue obtained after concentration was purified by silica gel chromatography (ISCO, 120 g of silica with 100% toluene using UV at 315 nm, then polarity was increased over time up to 10% ethyl acetate). The fractions were evaporated to give a 7:1 mixture of the desired/undesired isomers which was recrystallized overnight with ethyl acetate. The title material was obtained (216 mgs, 3.8%) as colorless crystals. LC (Method B): 1.928 min. LCMS (APCI) calcd for C$_{11}$H$_{10}$FO$_3$ [M+H]$^+$ m/z 209.06. found 209.1. $^1$H NMR (CDCl$_3$, 400 MHz) δ ppm: 7.55-7.61 (m, 1H), 6.78-6.99 (m, 1H), 6.46-6.53 (m, 1H), 3.96 (s, 3H), 2.55-2.60 (m, 3H).

36C. 1-(6-Fluoro-4-hydroxybenzofuran-2-yl)ethanone

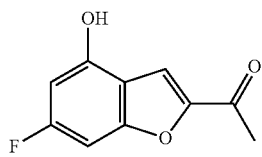

To a stirred solution of 1-(4,6-dimethoxybenzofuran-2-yl)ethanone (Example 36B, 216 mgs, 1.038 mmol) in chlorobenzene (3.69 mL, 36.3 mmol) was added aluminum trichloride (277 mgs, 2.075 mmol). After heating for 3 h at 85° C., the mixture was quenched with ice and 1.0N HCl, and extracted with ethyl acetate (4×). The combined organic layers were dried over anhydrous magnesium sulphate, filtered and concentrated. The residue was purified on silica gel chromatography (BIOTAGE® 24 g, eluting with a gradient of hexanes and ethyl acetate) to give the title material (0.191 g, 95%) as a white solid. LC (Method B): 1.794 min. LCMS (APCI) calcd for C$_{10}$H$_8$FO$_3$ [M+H]$^+$ m/z 195.05. found 195.9. $^1$H NMR (CDCl$_3$, 400 MHz) δ ppm: 7.58 (s, 1H), 6.87-6.93 (m, 1H), 6.46-6.53 (m, 1H), 5.62 (s, 1H), 2.60 (s, 3H).

36D. 1-(6-Fluoro-4-((2-phenylthiazol-4-yl)methoxy)benzofuran-2-yl)ethanone

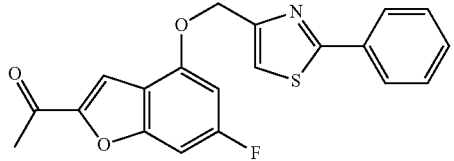 [SMILES: CC(=O)c1cc2c(OCc3csc(-c4ccccc4)n3)cc(F)cc2o1]

Benzene was added to 1-(6-fluoro-4-hydroxybenzofuran-2-yl)ethanone (Example 36C, 178 mgs, 0.917 mmol) and the mixture was sonicated for 30 sec. and concentrated in vacuo to remove traces of water in the starting material. Triphenylphosphine (373 mgs, 1.421 mmol) was added and the mixture was dried on high vacuum for 10 min. (2-Phenylthiazol-4-yl)methanol (Example 3B, 175 mgs, 0.917 mmol) and THF (15 mL) were added and the mixture was sonicated/heated for 5 min. Diisopropyl azodicarboxylate (275 µL, 1.412 mmol) in THF (2 mL) was added dropwise over 1 h and the resulting yellow solution was sonicated for 15 min. and stirred overnight at r.t. The mixture was diluted in dichloromethane, washed with saturated. NaHCO$_3$, brine, dried over MgSO$_4$ and concentrated. The residue was purified on silica gel chromatography (ISCO 24 g gold column, using 5% ethyl acetate in hexanes to 40% (10% increments)) to give the title material (132 mgs, 32%) as a white solid. LC (Method B): 2.613 min. LCMS (APCI) calcd for C$_{20}$H$_{15}$FNO$_3$S [M+H]$^+$ m/z 368.07. found 368.2. $^1$H NMR (CDCl$_3$, 400 MHz) δ ppm: 7.94-8.02 (m, 2H), 7.62-7.67 (m, 1H), 7.44-7.51 (m, 3H), 7.38 (s, 1H), 6.91-6.96 (m, 1H), 6.64-6.72 (m, 1H), 5.39 (d, J=0.78 Hz, 2H), 2.58 (s, 3H).

36E. 2-Bromo-1-(6-fluoro-4-((2-phenylthiazol-4-yl)methoxy)benzofuran-2-yl)ethanone

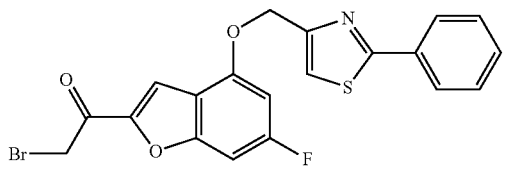 [SMILES: O=C(CBr)c1cc2c(OCc3csc(-c4ccccc4)n3)cc(F)cc2o1]

To a suspension of 1-(6-fluoro-4-((2-phenylthiazol-4-yl)methoxy)benzofuran-2-yl)ethanone (Example 36D, 132 mgs, 0.359 mmol) in ethyl acetate (5 mL) was added copper(II) bromide (160 mgs, 0.719 mmol) and the mixture was heated to 80° C. for 48 h. The solid was filtered off and rinsed with cold EtOAc. The solid was purified on silica gel chromatography (ISCO 12 g with dichloromethane and ethyl acetate (95:5)) and provided the title material (55 mgs, 34%) as an off-white solid. LC (Method B): 2.424 min. LCMS (APCI) calcd for C$_{20}$H$_{14}$BrFNO$_3$S [M+H]$^+$ m/z 445.99. found 446.0.

36F. 2-Bromo-6-(6-fluoro-4-((2-phenylthiazol-4-yl)methoxy)benzofuran-2-yl)imidazo[2,1-b][1,3,4]thiadiazole

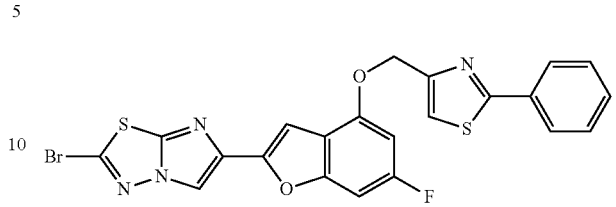

In a 2-5 mL microwave pressure vial was added 2-bromo-1-(6-fluoro-4-((2-phenylthiazol-4-yl)methoxy)benzofuran-2-yl)ethanone (Example 36E, 35 mgs, 0.078 mmol) in propan-2-ol (2 mL) followed by 5-bromo-1,3,4-thiadiazol-2-amine (16.2 mgs, 0.09 mmol). The reaction was heated to 80° C. overnight and to 150° C. for 1 h in microwave oven. The reaction mixture was then poured into a mixture of dichloromethane (8 mL) and saturated NaHCO$_3$ (2 mL) and this was extracted twice with dichloromethane. The organic extracts were dried over MgSO$_4$, filtered and concentrated. The residue was purified by silica gel chromatography (ISCO 12 g gold column using 100% dichloromethane, then 1% ethyl acetate and then 2% ethyl acetate in dichloromethane) to give the title material (18 mgs, 43%) as a yellowish solid. LC (Method B): 2.754 min. LCMS (APCI) calcd for C$_{22}$H$_{13}$BrFN$_4$O$_2$S$_2$ [M+H]$^+$ m/z 526.96. found 527.0.

Example 36

6-(6-Fluoro-4-((2-phenylthiazol-4-yl)methoxy)benzofuran-2-yl)-2-methoxyimidazo[2,1-b][1,3,4]thiadiazole

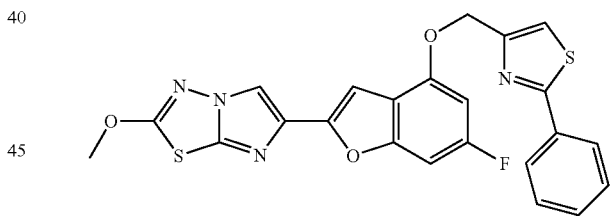

2-Bromo-6-(6-fluoro-4-((2-phenylthiazol-4-yl)methoxy)benzofuran-2-yl)imidazo[2,1-b][1,3,4]thiadiazole (17 mgs, 0.032 mmol) was dissolved in dichloromethane (1.3 mL) (some heat and sonication were required). Methanol was then added (0.3 mL) followed by sodium methoxide (14.74 µL, 0.064 mmol) in one shot. The reaction was stirred at r.t. for 25 min., then quenched with HCl 1.0 N and stirred until the reaction color changes to yellow. Sat. NaHCO$_3$ was then added and this was extracted with dichloromethane (4×). The combined organic layers were dried over MgSO$_4$, filtered and concentrated. The residue was purified by silica gel column chromatography (BIOTAGE® 12 g column using 100% dichloromethane to 5% ethyl acetate in dichloromethane (increment of 1%) to give the title material (10 mgs, 64%) as a yellowish solid. LC (Method A): 2.488 min. HRMS (ESI) calcd for C$_{23}$H$_{15}$FN$_4$O$_3$S$_2$ [M+H]$^+$ m/z 479.0570. found 479.0661. $^1$H NMR (CDCl$_3$, 400 MHz) δ ppm: 7.94-8.03 (m, 2H), 7.89 (s, 1H), 7.43-7.53 (m, 3H), 7.39 (s, 1H), 7.19 (s, 1H), 6.85-6.94 (m, 1H), 6.59-6.68 (m, 1H), 5.40 (s, 2H), 4.23 (s, 3H).

Example 37

6-(6-Chloro-4-((2-phenylthiazol-4-yl)methoxy)benzofuran-2-yl)-2-methoxyimidazo[2,1-b][1,3,4]thiadiazole

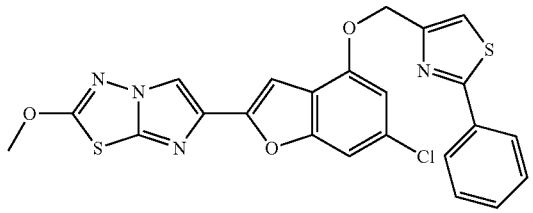 [SMILES: COc1nn2cc(-c3cc4c(OCc5csc(-c6ccccc6)n5)cc(Cl)cc4o3)nc2s1]

37A. 4-Chloro-2,6-dimethoxybenzaldehyde

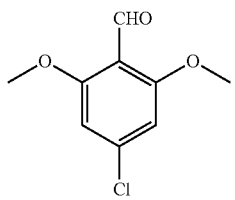

A solution of 1-chloro-3,5-dimethoxybenzene (5 g, 29.0 mmol) and TMEDA (4.37 mL, 29.0 mmol) in diethyl ether (100 mL, 962 mmol) at −78° C. under N2 atmosphere was charged with BuLi (19.91 mL, 31.9 mmol) dropwise over a period of 30 minutes using a syringe pump. After stirring for 4 hours at −78° C., DMF was added and the reaction mixture continued to stir for 1.5 hours after which 1N HCl (~30 mL) was added (all at −78° C.). The reaction mixture was warmed to room temperature and extracted with ethyl acetate. The organic phase was dried (MgSO$_4$), filtered and concentrated to dryness. The residue was purified by ISCO using hexanes/EtOAc as eluent. Fractions containing the desired product were concentrated to dryness to give the title material (1.97 g, 9.82 mmol, 33.9% yield) as a light yellow solid. LC (Method B): 1.924 min. LCMS (APCI) calcd for C$_9$H$_{10}$ClO$_3$ [M+H]$^+$ m/z 201.03. found 201.0. $^1$H NMR (CDCl$_3$, 400 MHz) δ ppm: 10.28 (s, 1H), 6.87 (s, 2H), 3.86 (s, 6H).

37B. 4-Chloro-2-hydroxy-6-methoxybenzaldehyde

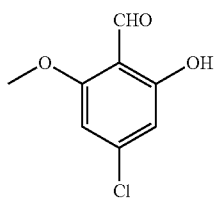

A stirred solution of 4-chloro-2,6-dimethoxybenzaldehyde (Example 37A, 1.95 g, 9.72 mmol) in DCM (20 mL, 311 mmol) at −78° C. was slowly added boron tribromide (9.72 mL, 9.72 mmol). The reaction mixture was stirred at −78° C. for 10 minutes then warmed to r.t. and stirred for 1 hour while monitoring reaction progress by LCMS. Once all s.m. had been consumed, the reaction was quenched with water and extracted with DCM. The organic phase was washed with brine, dried (MgSO$_4$), filtered and concentrated to dryness to give the title material (1.79 g, 9.59 mmol, 99% yield) as a purple solid. LC (Method B): 2.199 min. LCMS (APCI) calcd for C$_8$H$_8$ClO$_3$ [M+H]$^+$ m/z 187.02. found 187.0. $^1$H NMR (CDCl$_3$, 400 MHz) δ ppm: 11.89 (s, 1H), 10.20 (s, 1H), 6.75 (t, J=2.0 Hz, 1H), 6.66 (m, 1H), 3.91 (s, 1H).

37C. 1-(6-Chloro-4-methoxybenzofuran-2-yl)ethanone

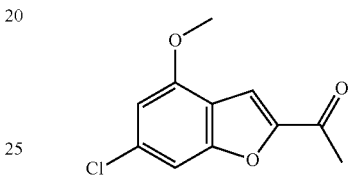

A stirred solution of 4-chloro-2-hydroxy-6-methoxybenzaldehyde (Example 37B, 1.79 g, 9.59 mmol) in N,N-dimethylformamide (15 mL, 9.59 mmol) was charged with cesium carbonate (3.75 g, 11.51 mmol) and 1-chloropropan-2-one (0.975 mL, 11.51 mmol). The reaction mixture was heated in a sealable vessel at 65° C. for 7 hours, was filtered over a Whatman filter paper to remove insolubles rinsing with DCM then washed with sat. NaHCO$_3$. The organic phase was dried (MgSO$_4$), filtered and concentrated to dryness. The residue was purified by ISCO using hexanes/EtOAc as eluent. Fractions containing the desired product were concentrated to give the title material (1.43 g, 6.37 mmol, 66% yield) as a light yellow solid. LC (Method A): 1.952 min. LCMS (APCI) calcd for C$_{11}$H$_{10}$ClO$_3$ [M+H]$^+$ m/z 225.03. found 225.0. $^1$H NMR (CDCl$_3$, 400 MHz) δ ppm: 7.94 (d, J=0.8 Hz, 1H), 7.49 (dd, J=0.8, 1.6 Hz, 1H), 6.97 (d, J=1.6 Hz, 1H), 3.97 (s, 3H).

37D. 1-(6-Chloro-4-hydroxybenzofuran-2-yl)ethanone

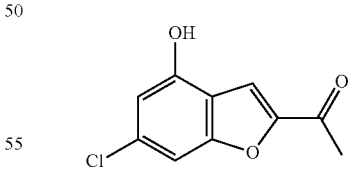

To a stirred solution of 1-(6-chloro-4-methoxybenzofuran-2-yl)ethanone (Example 37C, 1.43 g, 6.37 mmol) in chlorobenzene (15 mL, 148 mmol) was added aluminum chloride (3.40 g, 25.5 mmol) in portions over a period of 10 minutes. The reaction vessel was then sealed and heated at 100° C. for 40 minutes, then cool to r.t. and poured onto crushed ice (rinsed stirring bar with EtOAc). This was stirred for 30 minutes, then extracted with ethyl acetate. The organic phase was dried (MgSO$_4$), filtered and concentrated to dryness. The residue was purified by ISCO using hexanes/

EtOAc as eluent. Fractions containing the desired product were concentrated to give the title material (1.18 g, 5.60 mmol, 88% yield) as a light brown solid. LC (Method A): 1.783 min. LCMS (APCI) calcd for $C_{10}H_8ClO_3$ [M+H]$^+$ m/z 211.02. found 211.0. $^1$H NMR (CDCl$_3$, 400 MHz) δ ppm: 11.01 (s, 1 H), 7.89 (s, 1 H), 6.72 (s, 1H), 2.52 (s, 3H).

37E. 1-(4-(Benzyloxy)-6-chlorobenzofuran-2-yl)ethanone

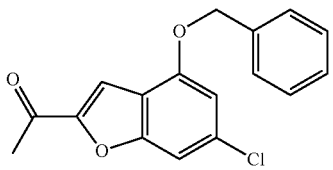 [SMILES: CC(=O)c1cc2c(OCc3ccccc3)cc(Cl)cc2o1]

A stirred solution of 1-(6-chloro-4-hydroxybenzofuran-2-yl)ethanone (Example 37D, 1.18 g, 5.60 mmol) in dry DMF (10 mL, 129 mmol) at r.t. was charged with $K_2CO_3$ (0.774 g, 5.60 mmol) and DMF. The reaction mixture was stirred for 1.5 hours then partitioned between ethyl acetate and water. The organic phase was washed with brine, dried (MgSO$_4$), filtered and concentrated to dryness. The residue was purified by ISCO using hexanes/EtOAc as eluent. Fractions containing the desired product were concentrated to give the title material (1.57 g, 5.22 mmol, 93% yield) as an amber colored oil. LC (Method B): 2.420 min. LCMS (APCI) calcd for $C_{17}H_{14}ClO_3$ [M+H]$^+$ m/z 301.06. found 301.0. $^1$H NMR (CDCl$_3$, 400 MHz) δ ppm: 8.00 (d, J=0.8 Hz, 1H), 7.53 (m, 3H), 7.44 (m, 2H), 7.38 (m, 1H), 7.10 (d, J=1.6 Hz, 1H), 5.53 (s, 2H), 2.54 (s, 3H).

37F. 1-(4-(Benzyloxy)-6-chlorobenzofuran-2-yl)-2-bromoethanone

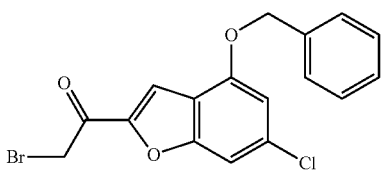 [SMILES: O=C(CBr)c1cc2c(OCc3ccccc3)cc(Cl)cc2o1]

A flame dried 200 ml round-bottom flask equipped with a stirring bar and under nitrogen atmosphere was charged with anhydrous THF (12 mL) followed by lithium bis(trimethylsilyl)amide (6.22 mL, 6.22 mmol). The mixture was cooled to –78° C. and treated with a solution of 1-(4-(benzyloxy)-6-chlorobenzofuran-2-yl)ethanone (Example 37E, 1.56 g, 5.19 mmol) in THF (6 ml+2 ml washing) added dropwise over 10 minutes via a syringe pump. The resulting mixture was stirred at –78° C. for 45 minutes and was then charged with trimethylchlorosilane (0.769 mL, 6.02 mmol) added dropwise over 5 minutes by syringe pump then stirred for another 20 minutes. The cooling bath was removed and the mixture was allowed to warm to +10° C. for 30 minutes. The reaction mixture was quenched with a mixture of cold ethyl acetate (80 mL), sat. NaHCO$_3$ (12 mL) and ice. The organic phase was dried (MgSO$_4$), stirring for ~5 minutes to remove all traces of water), filtered and concentrated to dryness to give the silyl enol ether as a yellow oil which was co-evaporated with toluene (4 mL). The silyl enol ether was dissolved in dry THF (20 mL), cooled to –30° C. (employing a cooling bath made from 1:1 CaCl$_2$: water using dry ice, bath stabilizes around –30 to –45° C.) and treated with NaHCO$_3$ (~50 mgs) followed by N-bromosuccinimide (0.923 g, 5.19 mmol) added in small portions over 15 minutes. The reaction mixture was allowed to warm to 0° C. over 2 hours (monitored by LCMS) and then quenched by addition of ethyl acetate (100 mL) and sat. NaHCO$_3$. The organic phase was washed with brine, dried (MgSO$_4$) and evaporated to give an orange solid which was purified by ISCO using hexanes/EtOAc as eluent. Fractions containing the desired product were concentrated to give the title material 1.48 g, 3.51 mmol, 67.6% yield) as a yellow solid. LC (Method B): 2.528 min. LCMS (APCI) calcd for $C_{17}H_{13}BrClO_3$ [M+H]$^+$ m/z 378.97. found 379.0.

37G. 6-(4-(Benzyloxy)-6-chlorobenzofuran-2-yl)-2-bromoimidazo[2,1-b][1,3,4]thiadiazole

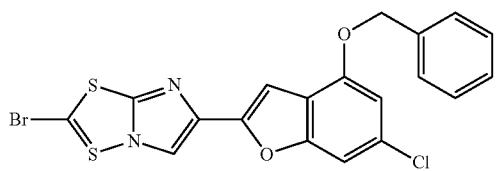

A sealable vessel was charged with 1-(4-(benzyloxy)-6-chlorobenzofuran-2-yl)-2-bromoethanone (Example 37F, 1.48 g, 3.51 mmol), 5-bromo-1,3,4-thiadiazol-2-amine (0.632 g, 3.51 mmol) and IPA (25 mL, 324 mmol). The reaction mixture was heated in an oil bath at 80° C. for 6 hours then heated in the microwave at 150° C. for 1 hour. The reaction mixture was allowed to stand for 1 hour and the insoluble material was filtered off and rinsed with MeOH to give the desired product as a brown solid (1.19 g, 2.58 mmol, 73.6% yield). LC (Method A): 2.549 min. LCMS (APCI) calcd for $C_{19}H_{12}BrClN_3O_2S$ [M+H]$^+$ m/z 459.95. found 460.0. $^1$H NMR (CDCl$_3$, 400 MHz) δ ppm: 8.74 (s, 1H), 7.55-7.50 (m, 2H), 7.45-7.34 (m, 4H), 7.17 (d, J=0.8 Hz, 1H), 7.02 (d, J=1.6 Hz, 1H), 5.32 (s, 2H).

37H. 6-(4-(Benzyloxy)-6-chlorobenzofuran-2-yl)-2-methoxyimidazo[2,1-b][1,3,4]thiadiazole

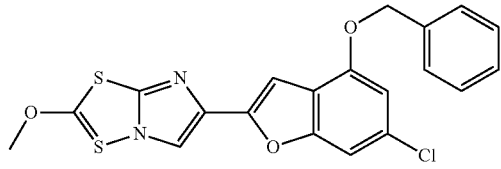

To a stirred solution of 6-(4-(benzyloxy)-6-chlorobenzofuran-2-yl)-2-bromoimidazo[2,1-b][1,3,4]thiadiazole (Example 37G, 1.18 g, 2.56 mmol) in DCM (40 mL, 622 mmol) and methanol (10 mL, 247 mmol) was added sodium methoxide (1.164 mL, 5.12 mmol). The reaction mixture was stirred at r.t. for 1 h 15 min while monitoring by TLC (7:3 hexanes:EtOAc). The reaction mixture was quenched with 1N HCl and extracted with DCM. The organic phase was washed with brine, dried (MgSO$_4$), filtered and concentrated to dryness. The residue was triturated with MeOH (sonication) and the solid material was filtered off, rinsed with MeOH and sucked dry to give the desired compound as a brown solid (859 mg, 2.086 mmol, 81% yield). LC (Method A): 2.478 min. LCMS (APCI) calcd for $C_{20}H_{15}ClN_3O_3S$ [M+H]$^+$ m/z 412.05. found 412.0. $^1$H NMR (CDCl$_3$, 400 MHz) δ ppm: 8.50 (s, 1H), 7.52 (m, 2H), 7.43 (m, 2H), 7.36 (m, 2H), 7.09 (d, J=0.8 Hz, 1H), 7.00 (d, J=1.6 Hz, 1H), 5.31 (s, 2H), 4.21 (s, 3H).

37I. 6-Chloro-2-(2-methoxyimidazo[2,1-b][1,3,4]thiadiazol-6-yl)benzofuran-4-ol

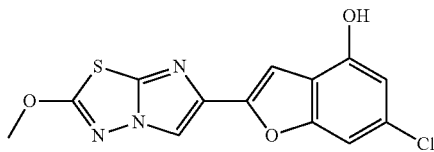 [SMILES: COc1nn2cc(-c3cc4c(O)cc(Cl)cc4o3)nc2s1]

A stirred solution of 6-(4-(benzyloxy)-6-chlorobenzofuran-2-yl)-2-methoxyimidazo[2,1-b][1,3,4]thiadiazole (Example 37H, 0.85 g, 2.064 mmol) and pentamethylbenzene (2.142 g, 14.45 mmol) in DCM under N2 atmosphere was cooled to −78° C. after which boron trichloride (5.16 mL, 5.16 mmol) was added dropwise over ~4 minutes. The reaction was monitored by TLC using 1:1 hexanes: EtOAc as eluent. The reaction mixture was stirred at −78° C. for 30 minutes after which a mixture of water (40 mL) and saturated NaHCO$_3$ (5 mL) was added (at −78° C.) and the mixture was stirred until ambient temperature was obtained (removed from cooling bath). The solid precipitate was filtered off and rinsed with diethyl ether then allowed to dry overnight to give the title material (441 mgs, 1.371 mmol, 66.4% yield) as a beige solid. The filtrate was extracted with DCM. The organic phase was washed with brine, dried (MgSO$_4$) and concentrated to dryness. The residue was purified by ISCO using DCM/EtOAc as eluent. Fractions containing the desired product were concentrated to give the title material (25 mgs, 0.078 mmol, 3.77% yield) as a beige solid. LC (Method A): 2.167 min. LCMS (APCI) calcd for $C_{13}H_9ClN_3O_3S$ [M+H]$^+$ m/z 322.00. found 322.0. $^1$H NMR (CDCl$_3$, 400 MHz) δ ppm: 10.50 (br. S, 1H), 8.45 (s, 1H), 7.17 (dd, J=0.8, 1.6 Hz, 1H), 7.09 (d, J=0.8 Hz, 1H), 6.67 (d, J=2.0 Hz, 2H), 4.21 (s, 3H).

Example 37

6-(6-Chloro-4-((2-phenylthiazol-4-yl)methoxy)benzofuran-2-yl)-2-methoxyimidazo[2,1-b][1,3,4]thiadiazole

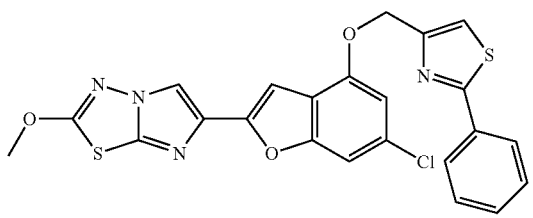 [SMILES: COc1nn2cc(-c3cc4c(OCc5csc(-c6ccccc6)n5)cc(Cl)cc4o3)nc2s1]

A flame-dried 100 mL round-bottom flask containing 6-chloro-2-(2-methoxyimidazo[2,1-b][1,3,4]thiadiazol-6-yl)benzofuran-4-ol (Example 37I, 25 mgs, 0.078 mmol) and (2-phenylthiazol-4-yl)methanol (Example 3B, 37.2 mgs, 0.194 mmol) in dry THF (4 mL) was added tributylphosphine (0.050 mL, 0.194 mmol). The resulting solution was charged with a solution of ADDP (49.0 mgs, 0.194 mmol) in THF (1 mL) added dropwise over 30 minutes via syringe pump. After stirring for 1.5 hours the reaction mixture was diluted with EtOAc then washed with 1N HCl, sat. NaHCO$_3$, water and brine. The organic phase was dried (MgSO$_4$) then concentrated to dryness. The residue was purified by ISCO using 0 to 10% diethyl ether in DCM. Fractions containing the desired product were concentrated to give the title material as a beige solid (20 mgs, 0.040 mmol, 52.0% yield). LC (Method A): 2.534 min. LCMS (APCI) calcd for $C_{23}H_{16}ClN_4O_3S_2$ [M+H]$^+$ m/z 495.03. found 495.0. $^1$H NMR (CDCl$_3$, 400 MHz) δ ppm: 8.49 (s, 1H), 7.99-7.96 (m, 2H), 7.93 (s, 1H), 7.55-7.50 (m, 3H), 7.40 (dd, J=0.8, 1.6 Hz, 1H), 7.15 (dd, J=0.4, 1.6 Hz, 1H), 7.14 (d, J=0.8 Hz, 1H), 5.43 (s, 2H), 4.21 (s, 3H).

Example 38

2-Methoxy-6-(4-((2-phenylthiazol-4-yl)methoxy)benzofuran-2-yl)imidazo[2,1-b][1,3,4]thiadiazole

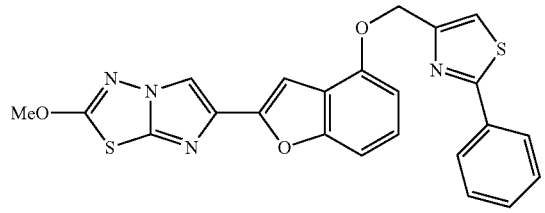 [SMILES: COc1nn2cc(-c3cc4c(OCc5csc(-c6ccccc6)n5)cccc4o3)nc2s1]

38A. 5-(Benzyloxy)-2,2-dimethyl-4H-benzo[d][1,3]dioxin-4-one

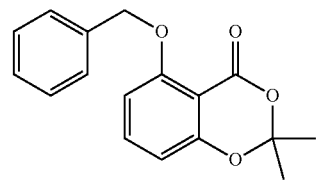 [SMILES: CC1(C)OC(=O)c2c(OCc3ccccc3)cccc2O1]

A solution of 5-hydroxy-2,2-dimethyl-4H-benzo[d][1,3]dioxin-4-one (6.00 g, 30.9 mmol) (Hadfield, A. et al., *Synthetic Communications*, 24(7):1025-1028 (1994)) in N,N-dimethylformamide (35 mL) was treated with powdered anhydrous potassium carbonate (5.15 g, 37.26 mmol) added all at once. The resulting mixture was stirred in vacuo for 10 min. and then flushed with nitrogen. The reaction flask was placed in a water bath (22° C.) and treated with benzyl bromide (5.55 g, 32.16 mmol) added dropwise over 15 min. The resulting mixture was then stirred at 22° C. for 18 h. The solid formed was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. Chromatography on silica gel (4×13 cm, elution toluene—ethyl acetate 0-5%) gave 8.78 g (100% yield) of the title material as a white solid. LC (Method A): 1.982 min. $^1$H NMR (CDCl$_3$, 600 MHz) δ ppm: 1.69 (s, 6H), 5.23 (s, 2H), 6.53 (d, J=8.2 Hz, 1H), 6.62 (d, J=8.4 Hz, 1H), 7.24-7.3 (m, 1H), 7.34-7.4 (m, 3 H), 7.52 (broad d, J=7.4 Hz 2H).

38B. 2-(Benzyloxy)-6-hydroxybenzaldehyde

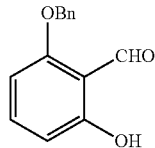

A solution of 5-(benzyloxy)-2,2-dimethyl-4H-benzo[d][1,3]dioxin-4-one (Example 38A, 4.00 g, 14.07 mmol) in dichloromethane (80 mL) was cooled to −78° C. and treated with a solution of diisobutylaluminum hydride (6.00 g, 42.2 mmol) in toluene (40 mL) added dropwise over 20 min. The resulting mixture was then stirred at −78° C. for 3 h. The reaction mixture was quenched by the careful addition of methanol (5 mL) added dropwise over 15 min, followed by 4 N hydrochloric acid (20 mL) added dropwise over 15 min. The cooling bath was then removed and an additional 80 mL of 4N hydrochloric acid was added over 10 min and the mixture was stirred vigorously at 22° C. for 4 h. The reaction mixture was diluted with ethyl acetate (200 mL), washed with brine, dried over anhydrous magnesium sulfate and evaporated in vacuo. The resulting oil was chromatographed on silica gel (4×10 cm, elution toluene) to give 2.25 g (70% yield) of the title material as a pale yellow solid. LC (Method A): 2.219 min. HRMS (ESI) calcd for C$_{14}$H$_{13}$O$_3$ [M+H]$^+$ m/z 229.0859. found 229.0859. $^1$H NMR (CDCl$_3$, 600 MHz) δ ppm: 5.12 (s, 2H), 6.43 (d, J=8.25 Hz, 1H), 6.52 (d, J=8.46 Hz, 1H), 7.34-7.4 (m, 6H), 10.39 (s, 1H), 11.95 (s, 1H).

38C. 1-(4-(Benzyloxy)benzofuran-2-yl)ethanone

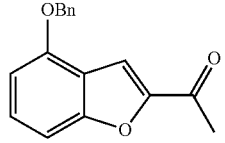 [SMILES: CC(=O)c1cc2c(OCc3ccccc3)cccc2o1]

A solution of 2-(benzyloxy)-6-hydroxybenzaldehyde (Example 38B, 11.10 g, 48.63 mmole) in N,N-dimethylformamide (120 mL) was treated with powdered anhydrous cesium carbonate (15.8 g, 48.63 mmol) added all at once. The resulting mixture was stirred in vacuo for 10 min and then flushed with nitrogen. The reaction flask was placed in a water bath (22° C.) and treated with chloroacetone (4.65 mL, 58.4 mmol) added dropwise over 10 min. The resulting mixture was then stirred at 22° C. for 18 h (no starting aldehyde left by tlc and formation of the intermediate alkylated aldehyde). The reaction mixture was then maintained under vacuum (10 mbar) for 15 min to remove any un-reacted chloroacetone and then flushed with nitrogen. Then anhydrous cesium carbonate (1.0 g, 3.1 mmol) was added and the mixture was heated at 55° C. and stirred for 40 h (more cesium carbonate, 1 g, was added after 24 h and 32 h) till complete conversion of the intermediate alkylated aldehyde into the benzofuran as monitored by TLC. The solid was filtered and washed with N,N-dimethylformamide. The filtrate was evaporated in vacuo and the residual oil was diluted with ethyl acetate (400 mL), washed with cold 0.1 N hydrochloric acid, saturated sodium bicarbonate and brine. After drying over anhydrous magnesium sulfate, evaporation of the solvent gave a thick syrup. Chromatography on silica gel (4.5×12 cm, elution toluene—ethyl acetate 2-4%) gave 11.67 g (90% yield) of the title benzofuran as a light yellow solid. Recrystallization from a mixture of ethyl acetate (40 mL) and hexane (40 mL) gave colorless prisms (10.50 g). LC (Method A): 2.162 min. FIRMS (ESI) calcd for C$_{17}$H$_{15}$O$_3$ [M+H]$^+$ m/z 267.1016. found 267.1022. $^1$H NMR (CDCl$_3$, 600 MHz) δ ppm: 2.56 (s, 3H), 5.20 (s, 2H), 6.73 (d, J=8.0 Hz, 1H), 7.17 (d, J=8.4 Hz, 1H), 7.3-7.5 (m, 6H), 7.63 (s, 1H).

38D. 1-(4-(Benzyloxy)benzofuran-2-yl)-2-bromoethanone

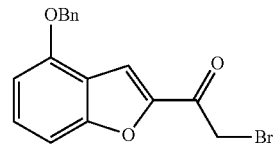 [SMILES: O=C(CBr)c1cc2c(OCc3ccccc3)cccc2o1]

A 250-mL, three-necked flask is equipped with a magnetic stirring bar and purged with a nitrogen atmosphere, was charged with anhydrous tetrahydrofuran (40 mL) followed by 21.6 mL (21.6 mmol) of a 1M solution of lithium bis(trimethylsilyl)amide in tetrahydrofuran. The mixture was cooled to −78° C. and treated with a solution of 1-(4-(benzyloxy)benzofuran-2-yl)ethanone (Example 38C, 5.00 g, 18.77 mmole in tetrahydrofuran (20 mL) added dropwise over 10 min. The resulting mixture was then stirred at −78° C. for 45 min. Then chlorotrimethylsilane (2.74 mL, 21.6 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (300 mL), saturated sodium bicarbonate (40 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (80 mL), cooled to −25° C. and treated with solid sodium bicarbonate (0.10 g) followed by N-bromosuccinimide (3.34 g, 18.8 mmol) added in small portions over 10 min. The reaction mixture was allowed to warm to 0° C. over 2 h and then quenched by addition of ethyl acetate (350 mL) and saturated sodium bicarbonate. The organic phase was washed with brine, dried over anhydrous magnesium sulfate and evaporated to give an orange oil. Chromatography on silica gel (4.5×12 cm, elution toluene—ethyl acetate 0-1%) gave 6.13 g of the title bromomethylketone as a yellow solid. Recrystallization from ethyl acetate (20 mL) and hexane (40 mL) gave pale yellow prisms (4.93 g, 76% yield). LC (Method A): 2.215 min. HRMS (ESI) calcd for C$_{17}$H$_{14}$BrO [M+H]$^+$ m/z 345.0121. found 345.0109. $^1$H NMR (CDCl$_3$, 600 MHz) δ ppm: 4.39 (s, 2H), 5.20 (s, 2H), 6.75 (d, J=7.86 Hz, 1H), 7.17 (d, J=8.25 Hz, 1H), 7.34-7.46 (m, 6H), 7.78 (s, 1H).

38E. 6-(4-(Benzyloxy)benzofuran-2-yl)-2-bromoimidazo[2,1-b][1,3,4]thiadiazole

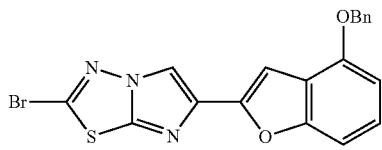 [SMILES: Brc1nn2cc(-c3cc4c(OCc5ccccc5)cccc4o3)nc2s1]

A mixture of 1-(4-(benzyloxy)benzofuran-2-yl)-2-bromoethanone (Example 38D, 3.00 g, 8.69 mmol) and 5-bromo-1,3,4-thiadiazol-2-amine (1.80 g, 10.0 mmol) in isopropanol (100 mL) was heated in a pressure flask equipped with a magnetic stirring bar at 80° C. for 20 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane) gave 2.82 g of the title imidazothiadiazole contaminated with some 1-(4-(benzyloxy)benzofuran-2-yl)ethanone. The solid material was triturated with ethyl acetate (15 mL), filtered, washed with ethyl acetate (10 ml) and dried in vacuo to give 2.37 g (64% yield) of pure title imidazothiadiazole as an off white solid which is used as such for the next step. LC (Method A): 2.425 min. HRMS (ESI) calcd for $C_{19}H_{13}BrN_3O_2S$ [M+H]$^+$ m/z 425.9906. found 425.9893. $^1$H NMR (CDCl$_3$, 600 MHz) δ ppm: 5.21 (s, 2H), 6.72 (d, J=8.07 Hz, 1H), 7.13 (d, J=8.26 Hz, 1H), 7.18 (broad t, 1H), 7.25 (s, 1H), 7.32 (broad t, 1H), 7.38 (broad t, 2H), 7.47 (broad d, 2H), 8.09 (s, 1H).

38F. 6-(4-(Benzyloxy)benzofuran-2-yl)-2-methoxyimidazo[2,1-b][1,3,4]thiadiazole

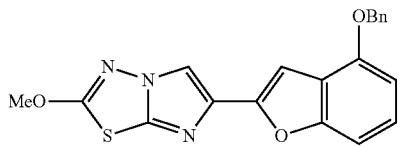 [SMILES: COc1nn2cc(-c3cc4c(OCc5ccccc5)cccc4o3)nc2s1]

A solution of 6-(4-(benzyloxy)benzofuran-2-yl)-2-bromoimidazo[2,1-b][1,3,4]thiadiazole (Example 38E, 3.22 g, 7.55 mmol) in a mixture of dichloromethane (400 mL) and methanol (50 mL) was treated at 22° C. with 6.3 mL of a 25 wt. % solution of sodium methoxide in methanol (30.2 mmol) added in one portion. More methanol (45 mL) was added and the mixture was stirred for 40 min. The reaction mixture was quenched by the addition of 40 mL of 1 N hydrochloric acid followed by 10 ml of saturated sodium bicarbonate. The solvent was evaporated under reduced pressure and the residue was diluted with dichloromethane (400 mL), washed with brine, dried over anhydrous magnesium sulfate and evaporated in vacuo. Crystallization of the white solid residue from 1,2-dichloroethane (30 mL) gave 2.19 g of the title material as a white solid. Chromatography of the mother liquors on silica gel (3×10 cm, elution with dichloromethane—ethyl acetate 0-1%) gave another 0.46 g of product (total yield 2.65 g, 93%). LC (Method A): 2.379 min. HRMS (ESI) calcd for $C_{20}H_{16}N_3O_3S$ [M+H]$^+$ m/z 378.0907. found 378.0911. $^1$H NMR (CDCl$_3$, 600 MHz) δ ppm: 4.18 (s, 3H), 5.21 (s, 2H), 6.71 (dd, J=7.4 Hz and J=0.95 Hz, 1H), 7.12-7.17 (m, 3H), 7.32 (broad t, 1H), 7.38 (broad t, 2H), 7.47 (broad d, 2H), 7.88 (s, 1H).

38G. 2-(2-Methoxyimidazo[2,1-b][1,3,4]thiadiazol-6-yl)benzofuran-4-ol

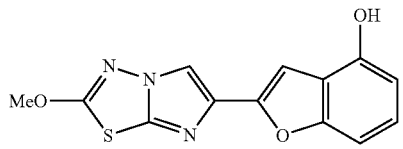 [SMILES: COc1nn2cc(-c3cc4c(O)cccc4o3)nc2s1]

A mixture of 6-(4-(benzyloxy)benzofuran-2-yl)-2-methoxyimidazo[2,1-b][1,3,4]thiadiazole (Example 38F, 2.640 g, 6.99 mmol) and pentamethylbenzene (7.25 g, 48.9 mmol) in dichloromethane (400 mL) was cooled to −78° C. under a nitrogen atmosphere and then treated immediately with 18.2 mL (8.2 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (10.6 g) in water (50 mL) added in one portion. The cooling bath was removed and the resulting mixture was stirred at room temperature for 1 h. The solid formed was filtered, washed successively with water (50 mL) and dichloromethane (25 mL). The filter cake was allowed to soak with anhydrous ethanol (10 ml) and then sucked dry. The white solid obtained was then dried under vacuum for a few days over phosphorous pentoxide until constant weight to give 1.459 g (72% yield) of title material. The combined filtrate and washings (organic and aqueous phases from the deprotection step) were diluted with dichloromethane (500 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and pentamethylbenzene) was triturated with toluene (20 mL). The solid was collected by filtration and washed with toluene (20 mL) to give, after drying in vacuo, 0.239 g (12% yield, 84% combined yield) of title material as a tan solid. LC (Method A): 1.908 min. HRMS (ESI) calcd for $C_{13}H_{10}N_3O_3S$ [M+H]$^+$ m/z 288.0437. found 288.0446. $^1$H NMR (DMSO-d$_6$, 600 MHz) δ ppm: 4.46 (s, 3H), 6.58 (d, J=7.8 Hz, 1H), 6.97 (d, J=8.15 Hz, 1H), 7.0-7.07 (m, 3H), 8.40 (s, 1H).

Example 38

2-Methoxy-6-(4-((2-phenylthiazol-4-yl)methoxy)benzofuran-2-yl)imidazo[2,1-b][1,3,4]thiadiazole

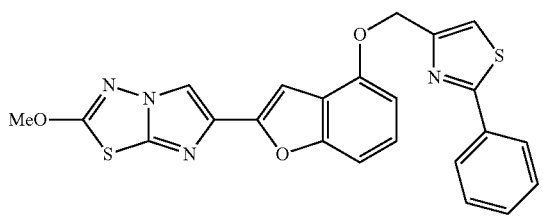 [SMILES: COc1nn2cc(-c3cc4c(OCc5csc(-c6ccccc6)n5)cccc4o3)nc2s1]

A mixture of 2-(2-methoxyimidazo[2,1-b][1,3,4]thiadiazol-6-yl)benzofuran-4-ol (Example 38G, 0.100 g, 0.349 mmol), triphenylphosphine (0.165 g, 0.627 mmol) and (2-phenylthiazol-4-yl)methanol (Example 3B, 0.080 g, 0.418 mmol) in a 50 ml flask was maintained under vacuum for 10 min and then purged with nitrogen. Dry tetrahydrofuran (10 mL) was added and the resulting mixture was slightly warmed and maintained in an ultrasonic bath for 5 min. The cooled mixture (still heterogeneous) was treated at 22° C. with a solution of diisopropyl azodicarboxylate (0.113 g, 0.558 mmol) in tetrahydrofuran (2 mL) added dropwise over 1 h. The mixture was then stirred at 2° C. for 4 h. The clear reaction mixture was quenched by the addition of dichloromethane (100 mL) and saturated sodium bicarbonate (10 mL). The organic phase was washed with brine, dried over anhydrous magnesium sulfate and concentrated in vacuo. Chromatography of the residue on silica gel (2.5×12 cm, elution dichloromethane—ethyl acetate 0-3%) followed by crystallization of the desired fraction from ethyl acetate (8 mL) gave 0.028 g (24% yield) of the title material as a white solid. LC (Method A): 2.426 min. HRMS (ESI) calcd for $C_{23}H_{17}N_4O_3S_2$ $[M+H]^+$ m/z 461.0737. found 461.0926. $^1$H NMR (CDCl$_3$, 400 MHz) δ ppm: 4.22 (s, 3H), 5.45 (d, J=0.78 Hz, 2H), 6.80 (dd, J=7.04, 1.57 Hz, 1H), 7.15-7.21 (m, 2H), 7.22 (s, 1H), 7.38 (s, 1H), 7.42-7.51 (m, 3H), 7.92 (s, 1H), 7.95-8.03 (m, 2H).

Example 39

4-(((6-Methoxy-2-(6-methylimidazo[1,2-b]pyridazin-2-yl)benzofuran-4-yl)oxy)methyl)-2-phenylthiazole

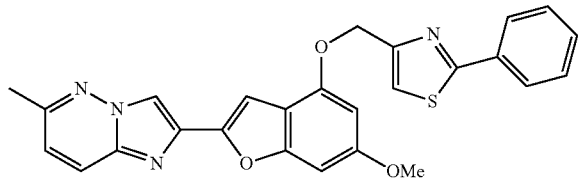 [SMILES: COc1cc(OCc2csc(-c3ccccc3)n2)c2cc(-c3cn4nc(C)ccc4n3)oc2c1]

39A. 2-(4-(Benzyloxy)-6-methoxybenzofuran-2-yl)-6-methylimidazo[1,2-b]pyridazine

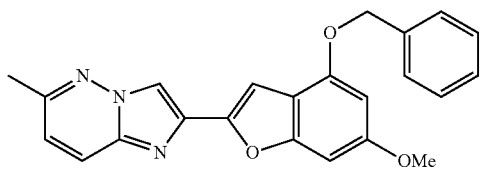 [SMILES: COc1cc(OCc2ccccc2)c2cc(-c3cn4nc(C)ccc4n3)oc2c1]

A mixture of 6-methylpyridazin-3-amine (1.52 g, 13.93 mmol), 1-(4-(benzyloxy)-6-methoxybenzofuran-2-yl)-2-bromoethanone (Example 1E, 5.00 g, 13.33 mmol) and 2-propanol (110 mL) in a 150 mL pressure flask was heated at 65° C. The mixture was almost homogeneous after 30 min of heating and precipitated again after 40 min. The mixture was heated for a total of 48 h. The cooled reaction mixture was diluted with dichloromethane (600 mL), washed with saturated sodium bicarbonate, brine and dried over anhydrous magnesium sulfate. Evaporation gave an orange brown solid which was chromatographed on silica gel (4×9 cm, elution dichloromethane—ethyl acetate 0-5%) to give the title material (3.64 g) as an orange brown solid. The solid was boiled with ethyl acetate (30 mL, partially soluble) and allowed to stand at room temperature for 2 h. The crystals were collected by filtration and dried overnight in vacuo to give the title material (3.440 g, 67%) as pale yellow brown needles. LC (Method A): 2.279 min. HRMS (ESI) calcd for $C_{23}H_{20}N_3O_3$ $[M+H]^+$ m/z 386.1499. found 386.1532. $^1$H NMR (CDCl$_3$, 400 MHz) δ ppm: 2.59 (s, 3 H), 3.86 (s, 3 H), 5.21 (s, 2 H), 6.43 (d, J=1.96 Hz, 1 H), 6.75 (broad d, 1 H), 6.94 (d, J=9.39 Hz, 1 H), 7.31-7.38 (m, 2 H), 7.38-7.45 (m, 2 H), 7.50 (broad d, J=7.43 Hz, 2 H), 7.82 (d, J=9.39 Hz, 1 H), 8.19 (s, 1 H).

39B. 6-Methoxy-2-(6-methylimidazo[1,2-b]pyridazin-2-yl)benzofuran-4-ol

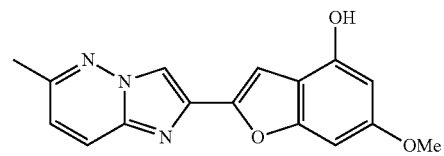 [SMILES: COc1cc(O)c2cc(-c3cn4nc(C)ccc4n3)oc2c1]

A solution of 2-(4-(benzyloxy)-6-methoxybenzofuran-2-yl)-6-methylimidazo[1,2-b]pyridazine (Example 39A, 1.00 g, 2.59 mmol) in a mixture of dichloromethane (420 mL) and methanol (150 mL) in a 1 L flask was hydrogenated over 10% Palladium over carbon (0.30 g, i.e., 30 mg Pd) and under 1 atm of hydrogen for 6 h. The reaction mixture was maintained under vacuum for 2 min and then flushed with nitrogen. The catalyst was filtered and washed with warm dichloromethane-methanol (8:2, 100 mL) and the combined filtrate was concentrated under reduced pressure. The yellow residue was boiled with 1,2-dichloroethane (30 mL) and allowed to stand at room temperature for 18 h. The solid was filtered (contains methanol by NMR) and dried in vacuo at 120° C. for 12 h to give the title material (0.760 g, 99% yield) of a yellow solid. LC (Method A): 1.844 min. $^1$H NMR (DMSO-d$_6$, 400 MHz) δ ppm: 2.54 (s, 3H), 3.77 (s, 3H), 6.28 (d, J=1.96 Hz, 1H), 6.70 (dd, J=1.96, 1.17 Hz, 1H), 7.20 (d, J=9.39 Hz, 1H), 7.24 (d, J=0.78 Hz, 1H), 8.03 (d, J=9.78 Hz, 1H), 8.50 (s, 1H), 10.10 (br s, 1H).

Example 39

4-(((6-Methoxy-2-(6-methylimidazo[1,2-b]pyridazin-2-yl)benzofuran-4-yl)oxy)methyl)-2-phenylthiazole

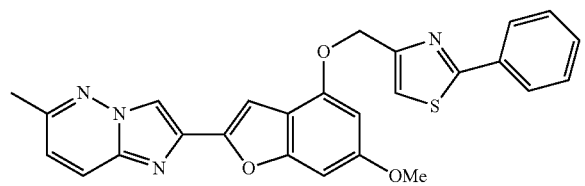 [SMILES: COc1cc(OCc2csc(-c3ccccc3)n2)c2cc(-c3cn4nc(C)ccc4n3)oc2c1]

In a 100 mL round-bottom flask, a suspension of 6-methoxy-2-(6-methylimidazo[1,2-b]pyridazin-2-yl)benzofuran-4-ol (Example 39B, 0.190 g, 0.643 mmol) and 4-(bromomethyl)-2-phenylthiazole (Table of bromides, 0.180 g, 0.708 mmol) in DMF (5 mL) was purged under vacuum and N2 for 10 min. The reaction was treated with potassium carbonate (0.24 g, 1.737 mmol) and stirred at 22° C. for 18 hours, then diluted with DCM and washed with water (1×), brine (1×). The organic layers were dried over anhydrous magnesium sulfate, filtered and concentrated. The residue was purified by silica gel chromatography (2.5×10 cm, 0% to 50% EtOAc in $CH_2Cl_2$) to give the impure title material (0.198 g, 66%). The solid was triturated in hot ethyl acetate to provide the pure title material (0.176 g). LC (Method A): 2.414 min. HRMS (ESI) calcd for $C_{26}H_{21}N_4O_3S$ $[M+H]^+$ m/z 469.1329. found 469.1379. $^1$H NMR ($CDCl_3$, 400 MHz) δ ppm: 2.57 (s, 3H), 3.84 (s, 3 H), 5.39 (s, 2 H), 6.46 (d, J=1.96 Hz, 1 H), 6.74 (broad d, 1 H), 6.91 (d, J=9.1 Hz, 1 H), 7.34 (s, 1 H), 7.36 (s, 1 H), 7.39-7.46 (m, 3 H), 7.80 (d, J=9.1 Hz, 1 H), 7.90-8.0 (m, 2 H), 8.19 (s, 1 H).

Example 40

(S)-2-(1-Fluoroethyl)-6-(6-methoxy-4-((2-phenylthiazol-4-yl)methoxy)benzofuran-2-yl)imidazo[2,1-b][1,3,4]thiadiazole

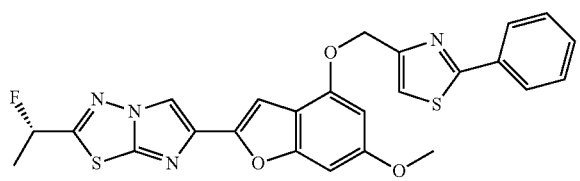 [SMILES: COc1cc(OCc2csc(-c3ccccc3)n2)c2cc(-c3cn4nc([C@H](C)F)sc4n3)oc2c1]

40A. (S)-5-(1-Fluoroethyl)-1,3,4-thiadiazol-2-amine

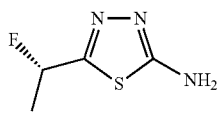

A 350 mL sealable pressure vessel was charged with thiosemicarbazide (11.17 g, 122.5 mmol) and dry dioxane (100 mL), and the mixture was cooled at 0° C. under an N2 atmosphere. To this rapidly stirring mixture was slowly added a solution of (S)-2-fluoropropanoic acid (9.40 g, 102.1 mmol, from Fritz-Langhals, E., *Tetrahedron Asymmetry*, 981 (1994)) in dioxane (10 mL). To the resulting mixture was added $POCl_3$ (11.22 mL, 122.5 mmol) dropwise, then the cooling bath was removed and the thick white slurry was stirred at room temperature for 1 h. The vessel was then sealed and the mixture was heated at 90-95° C. (oil bath temperature) for 5 h. The cooled mixture was stirred at room temperature for 14 h (Note: this was for convenience only and is optional) and then the supernatant (two-phase mixture) was decanted and concentrated under reduced pressure. The lower phase was slowly poured into ice water (250 mL) and then the concentrate was also added. This mixture was rapidly stirred until it was essentially a homogeneous (turbid) solution, and then it was basified to pH 9-9.5 using 40% aqueous NaOH. The resulting slurry was filtered and the filter-cake was washed with water (Note: LC of this beige solid showed that it contained only a trace of the desired product, so it was not further investigated). The combined filtrate was then extracted with EtOAc (×3) and the organic phase was dried ($Na_2SO_4$) and evaporated to give a cream solid (10.58 g, 70%) which was the essentially pure product according to LC and LCMS. This material was used as such without further purification. An analytical sample was purified by flash chromatography [Isco/0-20% (MeOH—$NH_4OH$, 9:1)-DCM] to give a white solid. LC (Method B): 0.608 min. MS (ESI) calcd. for $C_4H_6FN_3S$ m/z: 147.03; found: 148.05 $[M+H]+^1$H NMR (600 MHz, DMSO-$d_6$) δ 7.38 (s, 2H), 5.82 (dq, J=6.4, 48.0 Hz, 1H), 1.65 (dd, J=6.4, 24.0 Hz, 3H). Chiral LC: S:R=95:5.

40B. (S)-6-(4-(Benzyloxy)-6-methoxybenzofuran-2-yl)-2-(1-fluoroethyl)imidazo[2,1-b][1,3,4]thiadiazole

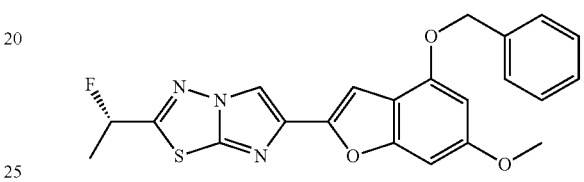

In a 20 mL vial, 1-(4-(benzyloxy)-6-methoxybenzofuran-2-yl)-2-bromoethanone (Example 1E, 407 mg, 1.085 mmol) and (S)-5-(1-fluoroethyl)-1,3,4-thiadiazol-2-amine (Example 40A, 202 mg, 1.373 mmol) were suspended in 2-propanol (10 ml, 130 mmol) and heated at 80° C. for 18 h. After 5 min. the solution became homogeneous. A precipitate was present after overnight stirring. The cooled mixtures were transferred into 20 mL microwaves vials and then heated 30 min at 150° C. The mixtures were combined, diluted in $CH_2Cl_2$ (200 mL) and washed once with sat. $NaHCO_3$, once with brine, dried over an h. $Na_2SO_4$ and concentrated. The residue was purified on ISCO using a REDISEP® Gold 40 g column ($CH_2Cl_2$/EtOAc). The crude product was adsorbed on $SiO_2$. Fractions were collected and the orange solid obtained was tritured twice in ACN to give the title material a light yellow solid. LC (Method B): 2.403 min. MS (ESI) calcd. for $C_{22}H_{19}FN_3O_3S$ $[M+H]^+$ m/z: 424.1126. found: 424.1146. $^1$H NMR (400 MHz, DMSO-$d_6$) d ppm 8.61 (s, 1H) 7.51 (d, J=7.4 Hz, 2H) 7.42 (t, J=7.6 Hz, 2H) 7.35 (t, J=7.0 Hz, 1H) 7.08 (s, 1H) 6.83-6.85 (m, 1H) 6.54 (d, J=1.2 Hz, 1H) 6.16 (dq, J=47.1, 6.4 Hz, 1H) 5.26 (s, 2H) 3.80 (s, 3H) 1.79 (dd, J=24.5, 6.8 Hz, 3H).

40C. (S)-2-(2-(1-Fluoroethyl)imidazo[2,1-b][1,3,4]thiadiazol-6-yl)-6-methoxybenzofuran-4-ol

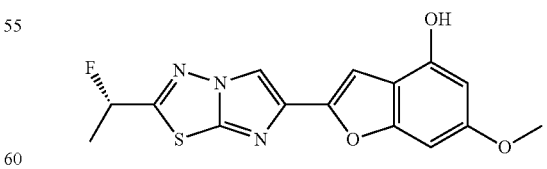

A mixture of (S)-6-(4-(benzyloxy)-6-methoxybenzofuran-2-yl)-2-(1-fluoroethyl)imidazo[2,1-b][1,3,4]thiadiazole (Example 40B, 0.152 g, 0.359 mmol) and pentamethylbenzene (0.374 g, 2.52 mmol) in dichloromethane (24 ml, 373 mmol) was cooled to −78° C. under nitrogen atmosphere and then treated immediately (to avoid crystallization) with boron trichloride 1.0M in dichloromethane (1 ml, 1.000 mmol) added dropwise over 3 min. The resulting mixture was stirred at −78° C. for 1 h. The reaction mixture was quenched by addition of a solution of sodium bicarbonate (0.71 g) in water (12 mL) added in one portion. The cooling bath was removed and the resulting mixture was stirred at room temperature for 1 h. The solid formed was filtered, washed successively with water (8 mL) and dichloromethane (8 mL). The filter cake was soaked with an h. ethanol and suck dried. The white solid obtained was dried under vacuum on $P_2O_5$ for 36 h. LC (Method B): 2.038 min. MS (ESI) calcd. for $C_{15}H_{13}FN_3O_3S$ [M+H]$^+$ m/z: 334.0656. found: 334.0680. $^1$H NMR (400 MHz, DMSO-d$_6$) δ ppm 10.06 (s, 1H) 8.56 (s, 1H) 7.09 (s, 1H) 6.67 (s, 1H) 6.26-6.28 (m, 1H) 6.16 (dq, J=46.9, 6.4 Hz, 1H) 3.76 (s, 3H) 1.80 (dd, J=24.7, 6.3 Hz, 3H).

Example 40

(S)-2-(1-Fluoroethyl)-6-(6-methoxy-4-((2-phenylthiazol-4-yl)methoxy)benzofuran-2-yl)imidazo[2,1-b][1,3,4]thiadiazole

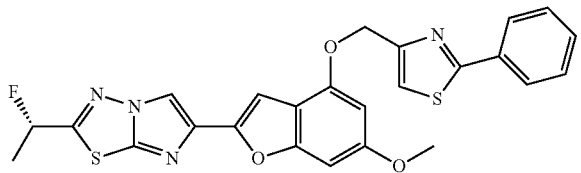 [SMILES: COc1cc(OCc2csc(-c3ccccc3)n2)c2cc(-c3cn4nc([C@H](C)F)sc4n3)oc2c1]

To a mixture of (S)-2-(2-(1-fluoroethyl)imidazo[2,1-b][1,3,4]thiadiazol-6-yl)-6-methoxybenzofuran-4-ol (Example 40C, 0.050 g, 0.150 mmol), (2-phenylthiazol-4-yl)methanol (Example 3B, 0.086 g, 0.450 mmol) and triphenylphosphine (0.118 g, 0.450 mmol) under N2 was added dry THF (3 mL). To the resulting light amber solution was added a solution of DIAD (0.087 mL, 0.450 mmol) in dry THF (2 mL) dropwise over 2 h to give light yellow-brown solution. After stirring at room temperature for an additional 30 min, LC showed that no starting material remained. The volatiles were then removed under reduced pressure to give an amber gum. Flash chromatography (Isco/0-20% ether-DCM) afforded the product as a nearly colorless gum. This gum was triturated with a minimum volume of MeOH and the resulting slurry was filtered and the filter-cake was washed with a minimum volume of MeOH and then dried in vacuo to give the title material (0.048 g, 63.2% yield) as a cream solid. The submission sample was lyophilized from MeCN—H$_2$O as a cream solid. LC (Method A): 2.453 min. HRMS (ESI) calcd for $C_{25}H_{20}FN_4O_3S_2$ [M+H]$^+$ m/z 507.0955. found 506.098. $^1$H NMR (DMSO-d$_6$, 400 MHz) δ ppm: 8.67 (s, 1H), 8.05-8.02 (m, 2H), 7.96 (s, 1H), 7.60-7.56 (m, 3H), 7.20 (d, J=0.8 Hz, 1H), 6.93 (dd, J=0.8, 2.0 Hz, 1H), 6.73 (d, J=1.6 Hz, 1H), 6.23 (dq, J=6.7, 47.0 Hz, 1H), 5.45 (s, 2H), 3.89 (s, 3H), 1.86 (d, J=6.7, 24.6 Hz, 3H).

Biology

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and antiangiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The pharmaceutical composition is administered using methods known in the art. Preferably, the compound is administered orally, rectally, nasally, by inhalation, topically or parenterally, e.g., subcutaneously, intraperitoneally, intramuscularly, and intravenously. The compound is optionally formulated as a component of a cocktail of therapeutic drugs to treat a thromboembolic disorder. In a preferred embodiment, the pharmaceutical composition is administered orally.

The therapeutic compounds described herein are formulated into pharmaceutical compositions utilizing conventional methods. For example, a PAR4 antagonist is formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, a conventional filler, and a tableting agent. Other formulations include an ointment, suppository, paste, spray, patch, cream, gel, resorbable sponge, or foam. Such formulations are produced using methods well known in the art. The compositions of the invention are also useful for parenteral administration, such as intravenous, subcutaneous, intramuscular, and intraperitoneal. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A. The FLIPR assay is also an exemplary in vitro assay for measuring the agonist activity of PAR4 agonist peptides. See Example H.

AYPGKF (SEQ ID NO: 1) is a known PAR4 agonist. An alternative PAR4 agonist is H-Ala-Phe(4-F)-Pro-Gly-Trp-Leu-Val-Lys-Asn-Gly-NH$_2$. As shown in Example B below, H-Ala-Phe(4-F)-Pro-Gly-Trp-Leu-Val-Lys-Asn-Gly-NH$_2$ (SEQ ID NO: 3) was validated as a PAR4 agonist in the FLIPR assay. A side-by-side comparison of the IC$_{50}$ values of ~180 compounds were performed using AYPGKF (SEQ ID NO: 1) versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ (SEQ ID NO: 3) has improved agonist activity as compared to AYPGKF (SEQ ID NO: 1) with an EC$_{50}$ that is 10 fold lower than the ECso for AYPGKF (SEQ ID NO: 1) in the FLIPR assay. PAR4 agonist peptides with improved potency enable a more robust assay with improved sensitivity and specificity. H-Ala-Phe(4-F)-Pro-Gly-Trp-Leu-Val-Lys-Asn-Gly-NH$_2$ (SEQ ID NO: 3) can be synthesized using methods well known to those of skill in the art, as shown in Examples AA-DD.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFFLRR (SEQ ID NO: 35) or other PAR1 agonist peptides.

The compounds of the current invention can be tested in vitro for their ability to inhibit platelet aggregation induced by gamma-thrombin as shown in Example C. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619. A platelet aggregation assay for measuring the agonist activity of PAR4 agonist peptides is shown in Example G.

Example D is an alpha-thrombin-induced platelet aggregation assay. Alpha-thrombin activates both PAR1 and PAR4. The ability of a selective PAR4 antagonist of the present invention, namely, the Example 3 compound to inhibit platelet aggregation was measured using a standard optical aggregometer. Inhibition of alpha-thrombin induced platelet aggregation by the Example 3 compound is shown in FIGS. 1A and 1B. The data shows, for the first time in the art, that a PAR4 antagonist alone can effectively inhibit platelet aggregation. The extent of platelet inhibition by the PAR4 antagonist is at least comparable to what has been previously described for PAR1 antagonists.

Example E is a tissue factor-induced platelet aggregation assay. The conditions in this assay mimic the physiological events during thrombus formation. In this assay, platelet aggregation in human PRP was initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The activity of the PAR4 antagonists of the present invention can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrically-induced carotid arterial thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention.

Assays

Materials
1) PAR1 and PAR4 Agonist Peptides
SFFLRR (SEQ ID NO: 35) is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF (SEQ ID NO: 1) and H-Ala-Phe(4-F)-Pro-Gly-Trp-Leu-Val-Lys-Asn-Gly-NH$_2$ (SEQ ID NO: 3) were synthesized. H-Ala-Phe(4-F)-Pro-Gly-Trp-Leu-Val-Lys-Asn-Gly-NH$_2$ (SEQ ID NO: 3) showed improved PAR4 agonist activity over AYPGKF (SEQ ID NO: 1) in the FLIPR assay (EC$_{50}$ of 2.3 µM for H-Ala-Phe(4-F)-Pro-Gly-Trp-Leu-Val-Lys-Asn-Gly-NH$_2$ (SEQ ID NO: 3) and 61 µM for AYPGKF (SEQ ID NO: 1)) and in washed platelet aggregation assay (EC$_{50}$ of 0.86 µM for H-Ala-Phe(4-F)-Pro-Gly-Trp-Leu-Val-Lys-Asn-Gly-NH$_2$ (SEQ ID NO: 3) and 13 µM for AYPGKF(SEQ ID NO: 1)).

2) PAR4 Expressing Cells
HEK293 cells stably expressing PAR4 were generated by a standard method of transfection of human F2R23 cDNA expression vector or by RAGE technology from Athersys Inc. (Cleveland, Ohio) and selected based on PAR4 protein expression of mRNA expression. Those cells demonstrated functional responses to PAR4 agonist peptide-induced intracellular calcium elevation using FLIPR® (Fluorometric Imaging Plate Reader; Molecular Devices Corp.). These cells express endogenous PAR1 and can elicit calcium signal upon stimulation with PAR1 agonist peptide. Cells were grown in Dulbecco's Modified Eagle's Medium (DMEM) (Invitrogen, Carlsbad, Calif.), 10% FBS, 1% PSG, 3 µg/ml puromycin and 25 nM Methotrexate) at 37° C. with 5% CO$_2$.

3) Preparation of Platelet Rich Plasma (PRP)
Human blood was collected in 3.8% sodium citrate at a ratio of 1 ml per 9 ml blood. The platelet rich plasma was isolated by centrifugation at 170 g for 14 minutes.

4) Preparation of Washed Platelets (WP)
Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~2.5×10$^8$/ml in Tyrode's Buffer (137 mM NaCl, 2 mM KCl, 1.0 mM MgCl$_2$, 1 mM CaCl$_2$, 5 mM glucose, 20 mM HEPES pH 7.4).

Example A

FLIPR Assay in PAR4-Expressing HEK293 Cells

Test for Antagonist Activity

The activity of the PAR4 antagonists of the present invention were tested in PAR4 expressing cells by monitoring H-Ala-Phe(4-F)-Pro-Gly-Trp-Leu-Val-Lys-Asn-Gly-NH$_2$(SEQ ID NO: 3)-induced intracellular calcium mobilization using FDSS6000 (Hamamatsu Photonics, Japan) by fluo-4. Counter screens for agonist activity and PAR1 antagonist activity were also performed. Briefly, HEK293 EBNA PAR4 clone 20664.1J cells were plated 24 hrs. prior to experiment in 384 well, Poly-D-Lysine coated, black, clear bottom plates (Greiner Bio-One, Monroe, N.C.). Cells were plated at 20,000 cells/well in 20 µl growth medium and incubated at 37° C. with 5% CO$_2$ overnight. At time of assay, media was replaced with 40 µl 1× Hank's Buffered Saline Solution (HBSS) (with 10 mM HEPES) and 20 µl test compound also diluted in 1×HBSS buffer was added at various concentrations and 0.67% DMSO final concentration on the FDSS for agonist measurement. The cells were then incubated for 30 minutes at room temperature followed by addition of 20 µl of agonist peptide for antagonist measurement on the FDSS. The agonist peptide H-Ala-Phe(4-F)-Pro-Gly-Trp-Leu-Val-Lys-Asn-Gly-NH$_2$ (SEQ ID NO: 3) for PAR4 antagonist screen or SFFLRR for PAR1 counter screen were routinely tested to ensure a response at ECso in the assay (~2.3 µM for H-Ala-Phe(4-F)-Pro-Gly-Trp-Leu-Val-Lys-Asn-Gly-NH$_2$(SEQ ID NO: 3) and 600 nM for SFFLRR).

Example B

Validation of H-Ala-Phe(4-F)-Pro-Gly-Trp-Leu-Val-Lys-Asn-Gly-NH$_2$ (SEQ ID NO: 3) as a PAR4 Agonist To validate H-Ala-Phe(4-F)-Pro-Gly-Trp-Leu-Val-Lys-Asn-Gly-NH$_2$(SEQ ID NO: 3) as a PAR4 agonist in the FLIPR assay, side-by-side comparison of the IC$_{50}$ values of ~180 compounds were performed using AYPGKF (SEQ ID NO: 1) versus H-Ala-Phe(4-F)-Pro-Gly-Trp-Leu-Val-Lys-Asn-Gly-NH$_2$. The results demonstrated a strong correlation between the two assays (Spearman's rank correlation coefficient rho=0.7760, p<0.0001). The relevance of the FLIPR assay in the HEK293 cells was confirmed by a direct assay connectivity to the washed platelet assay. The IC$_{50}$ values of ~200 compounds from AYPGKF FLIPR assay was strongly correlated to that from AYPGKF washed platelet aggregation assay (Spearman's rank correlation coefficient rho=0.836, p<0.001). Similar results were obtained comparing FLIPR and washed platelet data using H-Ala-Phe(4-F)-Pro-Gly-Trp-Leu-Val-Lys-Asn-Gly-NH$_2$.

Example C

Gamma Thrombin Induced Platelet Aggregation Assays

Test for Antagonist Activity

The ability of the compounds of the current invention to inhibit platelet aggregation induced by gamma-thrombin was tested in a 96-well microplate aggregation assay format. Briefly, PRP or washed platelet suspension (100 µl) was pre-incubated for 5 minutes at room temperature with varying concentrations of compounds. Aggregation was initiated by ~10-50 nM gamma thrombin (Haematologic Technologies, Essex Junction, Vt.), which was titrated daily to achieve 80% platelet aggregation. Refludan at 1 U/mL (Berlex, Montville, N.J.) was added to the gamma thrombin sample to prevent PAR1 activation induced by residual alpha-thrombin contamination. The plate was then placed into a 37° C. Molecular Devices (Sunnyvale, Calif.) SPECTRAMAX® Plus Plate Reader. The plate was mixed for 10 seconds before the first read and 50 seconds between each read for up to 15 minutes at 405 nM. Data was collected with SOFTMAX® 4.71 software. The plate also included an untreated control sample which served as ODmax, while buffer containing no platelets was the ODmin. Platelet aggregation was determined by subtracting the ODmax from the ODmin for the 100% aggregation value. In experimental samples, the observed minimum value was subtracted from the minimum value and then compared to the 100% aggregation value to determine the percentage aggregation. IC$_{50}$ values are determined using Excel Fit software.

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example D

Alpha-Thrombin Induced Platelet Aggregation Assays

Test for Antagonist Activity

The ability of PAR4 antagonist to inhibit platelet aggregation induced by alpha-thrombin was tested using human washed platelets. Example 3 was pre-incubated with washed platelets for 20 min. Aggregation was initiated by addition of 1.5 nM alpha-thrombin (Haematologic Technologies, Essex Junction, Vt.) to 300 µl of washed platelets at stirring speed of 1000 rpm. Platelet aggregation was monitored using Optical Aggregometer (Chrono-Log, Havertown, Pa.) and the area under the curve (AUC) at 6 min was measured. IC$_{50}$ was calculated using vehicle control as 0% inhibition. The IC$_{50}$ for the inhibition of platelet aggregation by Example 3 was calculated to be 5 nM (n=3) (FIGS. 1A and 1B).

Example E

Tissue Factor-Induced Platelet Aggregation Assay

Test for Antagonist Activity

The ability of PAR1 or PAR4 antagonists to inhibit platelet aggregation induced by endogenous thrombin can be tested in a tissue factor driven aggregation assay. Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example F

The following Table sets out the results obtained employing various compounds of the invention tested in the FLIPR assay and the platelet aggregation assay (PRP assay). As indicated above, the FLIPR assay, an in vitro assay, measures the PAR4 antagonist activity of compounds tested as described in Example A. The PRP assay, an in vitro assay, measures the PAR4 antagonist assay of the compounds tested in the presence of plasma proteins and thrombin agonist as described in Example C.

| Example | PAR4 FLIPR assay ($EC_{50}$, nM) | PRP assay (Gamma Thrombin, $IC_{50}$, nM) |
| --- | --- | --- |
| 2 | 0.42 | 49 |
| 3 | 0.32 | 4.7 |
| 8 | 3.9 | >3000 |
| 9 | 5.3 | >3000 |
| 10 | 3.5 | 2700 |
| 18 | 2.5 | 3.6 |
| 28 | 0.51 | 2.9 |
| 33 | 1.7 | 38 |
| 36 | 1 | 48 |

Example G

PAR4 Agonist Peptide Induced Platelet Aggregation Assays

Test for Agonist Activity of PAR4 Agonist Peptides

The ability of the compounds of the current invention to induce platelet aggregation was tested in a 96-well microplate aggregation assay format. Briefly, a washed platelet suspension with varying concentrations of agonist compounds was assayed. Aggregation was initiated by the addition of a titered test agonist peptide. The plate was then placed into a 37° C. Molecular Devices SPECTRAMAX® Plus Plate Reader (Sunnyvale, Calif.). The plate was mixed for 10 seconds before the first read and 20 seconds between each read for up to 15 minutes at 405 nM. Data was collected with SOFTMAX® 4.71 software. The plate also included an untreated control sample which served as ODmax, while buffer containing no platelets was the ODmin. Platelet aggregation was determined by subtracting the ODmax from the ODmin for the 100% aggregation value. In experimental samples, the observed transmission was subtracted from the minimum value and then compared to the 100% aggregation value to determine the percentage aggregation. $ED_{50}$ values were determined using Excel Fit software.

Example H

FLIPR Assay in PAR4-Expressing HEK293 Cells

Test for Agonist Activity of PAR4 Agonist Peptides

The activity of the PAR4 agonist peptides of the present invention were tested in PAR4 expressing cells by monitoring PAR4-induced intracellular calcium mobilization using FDSS6000 (Hamamatsu Photonics, Japan) by fluo-4. Briefly, HEK293 cells expressing human PAR4 were plated 24 hrs. prior to experiment in 96 well or 384 well, Poly-D-Lysine coated, black, clear bottom plates (Greiner Bio-One, Monroe, N.C.). Cells were plated at 40,000 cells/well (96 well) or 20,000 cells/well (384 well) and incubated at 37° C. with 5% $CO_2$ overnight. At the time of assay, media was replaced with 1× Hank's Buffered Saline Solution (HBSS) (with 10 mM HEPES) for the 96 well or 384 well assays respectively. The cells were then incubated for 30 minutes at room temperature followed by addition of a varying concentration of agonist peptide for measurement on the FDSS.

Example I

The following Table sets forth the results obtained when several peptides were assessed using the methods described in Examples G and H above.

| SEQ ID NO. | $EC_{50}$ (μM) FLIPR Assay | $ED_{50}$ (μM) [Platelet Aggregation] |
| --- | --- | --- |
| 1 | 61 | 13 |
| 2 | 4.8 | NT* |
| 3 | 2.3 | 0.86 |
| 4 | 3.9 | NT* |
| 5 | 4.1 | NT* |
| 6 | 2.6 | 1.1 |
| 7 | 9.5 | NT* |
| 8 | 26 | NT* |
| 9 | 410 | NT* |
| 10 | 600 | NT* |
| 11 | 159 | NT* |
| 12 | NT* | 0.97 |
| 13 | NT* | 0.67 |
| 14 | NT* | 12.3 |
| 15 | 0.45 | 0.63 |
| 16 | NT* | 37 |
| 17 | NT* | 106 |
| 18 | NT* | 5.5 |
| 19 | NT* | 1.6 |
| 20 | NT* | 4.1 |
| 21 | NT* | 2.4 |
| 22 | NT* | 1.2 |
| 23 | NT* | 0.79 |
| 24 | 0.75 | 0.69 |
| 25 | NT* | 52 |
| 26 | NT* | 1.0 |
| 27 | NT* | 1.7 |
| 28 | 1.5 | 0.76 |
| 29 | NT* | 1.0 |
| 30 | NT* | 1.7 |
| 31 | 0.72 | 0.63 |
| 32 | 0.31 | 0.61 |
| 33 | NT* | 1.2 |
| 34 | NT* | 3.0 |

*Not Tested

Synthesis of PAR4 Agonist Peptides

Example AA

Solid Phase Peptide Synthesis of Peptides using the Advanced ChemTech Model 90 Synthesizer and Advanced ChemTech Model 396Ω Multiple Peptide Synthesizer The peptide-resin Fmoc-Pro-Gly-Lys(Boc)-Phe-Rink amide MBHA resin was prepared using the following procedure. Fmoc-Rink amide MBHA resin (6.3 g, 0.66 mmole/g, 4.16 mmoles total) was charged to a 200 mL reactor and placed on an Advanced ChemTech Model 90 Synthesizer. The resin was subjected to the following cycles:
1. DMF wash, 1×60 mL×2 mins.
2. 20% piperidine in DMF, 1×60 mL×5 mins.
3. 20% piperidine in DMF, 1×60 mL×15 mins.
4. DMF washes, 4×60 mL×1 mins.
5. NMP washes, 4×60 mL×1 mins.
6. Coupling (see below)
7. NMP washes, 4×60 mL×1 mins.

The couplings were carried out using the reagents in the table below. The Fmoc-AA and HCTU were dissolved in NMP/DCM 3:1 (45 mL). To this was added the DIEA with stirring. The resulting solution was then added to the deprotectected resin and mixing was allowed for 1 to 3.5 hours until a negative Kaiser ninhydrin test was obtained.

|  | Reagent | MW | mmol | Weight |
|---|---|---|---|---|
| Cycle 1 | Fmoc-Phe-OH | 387.4 | 16.68 | 6.46 g |
|  | HCTU | 413.7 | 16.73 | 6.92 g |
|  | DIEA | 129.3 | 35.98 | 4.65 g |
| Cycle 2 | Fmoc-Lys(Boc)-OH | 468.5 | 16.63 | 7.79 g |
|  | HCTU | 413.7 | 16.68 | 6.90 g |
|  | DIEA | 129.3 | 35.51 | 4.59 g |
| Cycle 3 | Fmoc-Gly-OH | 297.3 | 16.78 | 4.99 g |
|  | HCTU | 413.7 | 16.68 | 6.90 g |
|  | DIEA | 129.3 | 35.36 | 4.57 g |
| Cycle 4 | Fmoc-Pro-OH | 337.4 | 16.72 | 5.64 g |
|  | HCTU | 413.7 | 16.68 | 6.90 g |
|  | DIEA | 129.3 | 36.13 | 4.67 g |

The Fmoc group was removed from the Pro residue using steps 2 to 5 above. The Pro-Gly-Lys(Boc)-Phe-Rink amide MBHA resin was suspended in NMP/DCM 1:1 (200 mL) and 2 mL of the suspension was added to 88 wells on an Advanced ChemTech Model 396Ω multiple peptide synthesizer. A 0.3 M Fmoc-AA/0.3 M HOAt in DMF solution (0.5 mL) was added to each well, followed by 0.2 mL of 0.77 M DIC in DMF. The reaction block was vortexed for 25 hours. The peptidyl-resins were washed and deprotected as described below.

Fmoc-Alanine or the appropriate Fmoc-AA was coupled as above to the peptidyl-resins followed by washing and removal of the Fmoc protecting group as stated above. The final washes were NMP then DCM both 4×2 mL×1 min. followed by a 10 minute nitrogen purge of the peptidyl-resins.

a. Cleavage/Deprotection

The desired peptides were cleaved/deprotected from their respective peptidyl-resins by treatment with a TFA cleavage mixture as follows. A solution of TFA/water/tri-isopropylsilane (96:2:2) (1.0 mL) was added to each well in the reactor block, which was then vortexed for 30 mins. This was repeated once more and the TFA solutions from the wells were collected by positive pressure into pre-tared vials located in a matching 96-vial block on the bottom of the reactor. The vials were allowed to stand so that the total contact time with the cocktail was 80 minutes. The vials were concentrated in a SPEEDVAC® (Savant) to a volume of about 1.0 mL which was then added to diisopropyl ether (10 mL) and was briefly shaken. The vial was held at −15° C. for 1 hour. The precipitates were pelleted by centrifugation and the supernatants were decanted. The vials were dried in a SPEEDVAC® (Savant) for 30 minutes to yield the crude peptides, typically in >100% yields (20-40 mgs). The crude peptides dissolved directly in water (2.5 mL) and acetonitrile (0.5 mL) and were filtered into vials. The solvents were removed in a SPEEDVAC® (Savant) to yield the crude peptides which were used as is.

b. HPLC Analysis of the Peptides

After purification by preparative HPLC as described above, each peptide was analyzed by analytical RP-HPLC on a Shimadzu LC-10AD or LC-10AT analytical HPLC system consisting of: a SCL-10A system controller, a SIL-10A auto-injector, a SPD10AV or SPD-M6A UV/VIS detector, or a SPD-M10A diode array detector. One of the following methods was used: A PHENOMENEX® Luna C18(2) 5 μm (4.6×50 mm) column was used and elution was performed using the following gradient: 10-100% B in A over 10 min, 1.25 mL/min.; Mobile phase A: 0.1% TFA/water; mobile phase B: 0.1% TFA/acetonitrile.

c. Characterization by Mass Spectrometry (See Below)

Example BB

Simultaneous Solid Phase Peptide Synthesis of Peptides on an Advanced ChemTech Model 396Ω Multiple Peptide Synthesizer Rink amide resin (0.6822 g of 0.6 mmole/g substitution) was swelled in DMF/DCM 1:1 (final volume 8 mL). The resin suspension was distributed to 8 wells in the reaction block (1 mL per well). The Fmoc group was then removed using two treatments, 5 and 15 minutes each respectively, with 20% piperidine in DMF (1 mL per treatment). The resin was washed with NMP (10×1.5 mL×1 min.). A 0.31 M solution of Fmoc-amino acid and 0.31 M 6-Cl-HOBt in NMP (1 mL) was added to the resin followed by a 0.78 M DIC in NMP solution (0.4 mL). The resin was vortexed for 2 hours after which the resin was drained, washed with NMP (7×1.5 mL×1 min.). This cycle was repeated until the number of automated coupling cycles required to assemble the respective peptide sequences as determined by the pre-programmed sequence synthesis table.

The detailed stepwise synthesis protocol used for a typical 0.05 mmol/well simultaneous synthesis of peptides is described below. This protocol was adapted for the simultaneous synthesis of arrays of analogs ranging from 4 to 96 per individual run.

Automated Synthesis of PAR4 Agonist Peptides

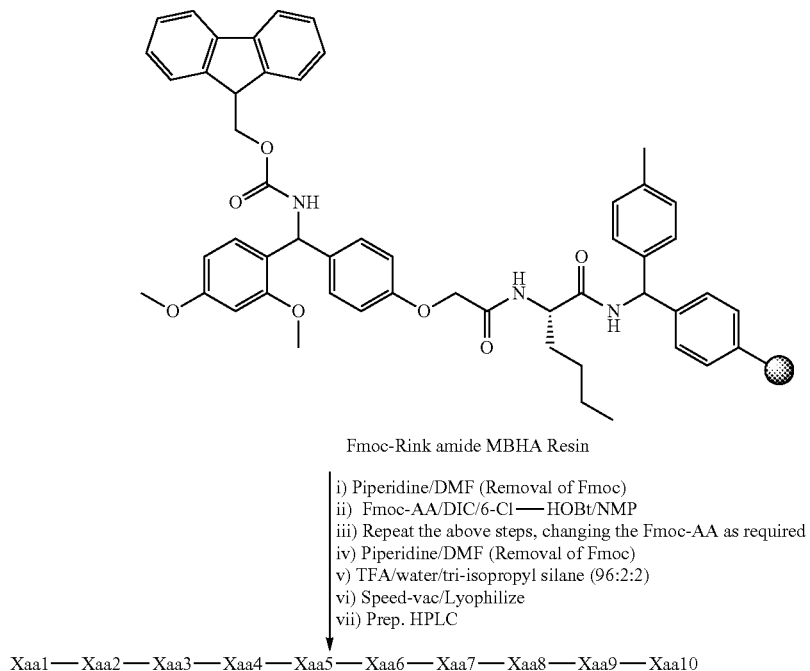

Fmoc-Rink amide MBHA Resin i) Piperidine/DMF (Removal of Fmoc)
ii) Fmoc-AA/DIC/6-Cl—HOBt/NMP
iii) Repeat the above steps, changing the Fmoc-AA as required
iv) Piperidine/DMF (Removal of Fmoc)
v) TFA/water/tri-isopropyl silane (96:2:2)
vi) Speed-vac/Lyophilize
vii) Prep. HPLC Xaa1—Xaa2—Xaa3—Xaa4—Xaa5—Xaa6—Xaa7—Xaa8—Xaa9—Xaa10

Prior to starting the synthesis, the following reagent solutions were prepared and placed on the instrument as required: 20% piperidine in DMF; 0.78 M DIC in NMP.

The required Fmoc-protected amino acids were prepared as 0.31 M solutions in 0.31 M 6-Cl-HOBt/NMP and placed into the appropriate positions in the 32-position amino acid rack.

Finally, the Fmoc group was removed with 20% piperidine in DMF as described above, and the peptidyl-resins were washed with NMP (3×1.5 mL) and DCM (6×1.5 mL).

a. Cleavage/Deprotection

The desired peptides were cleaved/deprotected from their respective peptidyl-resins by treatment with a TFA cleavage mixture as follows. A solution of TFA/water/tri-isopropyl-silane (96:2:2) (1.0 mL) was added to each well in the reactor block, which was then vortexed for 30 mins. This was repeated twice more and the TFA solutions from the wells were collected by positive pressure into pre-tared vials located in a matching 96-vial block on the bottom of the reactor. The vials were concentrated in a SPEEDVAC® (Savant) to a volume of about 0.2 mL. The crude peptides were then precipitated by the addition of diisopropyl ether (4 mL) and being briefly vortexed. The precipitates were pelleted by centrifugation and the supernatants were decanted. The vials were dried in a SPEEDVAC® (Savant) to yield the crude peptides, typically in >100% yields (20-40 mgs). The crude peptides dissolved directly in 2 mL of water and acetonitrile was added as necessary for complete dissolution. The peptides were purified by preparative HPLC.

b. Preparative HPLC Purification of the Crude Peptides

Preparative HPLC was carried out either on a Waters Model 4000 or a Shimadzu Model LC-8A liquid chromatograph. Each solution of crude peptide was injected into a YMC S5 ODS-A (250×20 mm) column and eluted using a linear gradient of MeCN in water, both buffered with 0.1% TFA. A typical gradient used was from 0% to 50% 0.1% TFA/MeCN in 0.1% TFA/water over 40 min. at a flow rate of 15 mL/min with effluent UV detection at 217 nm. Fractions (5 to 10 mL) were collected on a fraction collector. Those containing the desired peptide as determined by HPLC and MS analyses were pooled and lyophilized to yield amorphous white powders.

c. HPLC Analysis of the Purified Peptides

After purification by preparative HPLC as described above, each peptide was analyzed by analytical RP-HPLC on a Shimadzu LC-10AD or LC-10AT analytical HPLC system consisting of: a SCL-10A system controller, a SIL-10A auto-injector, a SPD10AV or SPD-M6A UV/VIS detector, or a SPD-M10A diode array detector. One of the following methods was used: Method A; A YMC ODS-AQ S3 (4.6×150 mm) column was used and elution was performed using the following gradient: 0-60% B in A over 30 min, 1.0 mL/min.; Method B; A YMC ODS-AQ S3 (4.6×150 mm) column was used and elution was performed using the following gradient: 0-60% B in A over 60 min, 1.0 mL/min.; Mobile phase A: 0.1% TFA/water; mobile phase B: 0.1% TFA/acetonitrile.

d. Characterization by Mass Spectrometry

Each peptide was characterized by electrospray mass spectrometry (ES-MS) either in flow injection or LC/MS mode. Finnigan SSQ7000 single quadrupole mass spectrometers (ThermoFinnigan, San Jose, Calif.) were used in all analyses in positive and negative ion electrospray mode. Full scan data was acquired over the mass range of 300 to 2200 amu for a scan time of 1.0 second. The quadrupole was operated at unit resolution. For flow injection analyses, the mass spectrometer was interfaced to a Waters 616 HPLC pump (Waters Corp., Milford, Mass.) and equipped with an HTS PAL autosampler (CTC Analytics, Zwingen, Switzerland). Samples were injected into a mobile phase containing 50:50 water:acetonitrile with 0.1% ammonium hydroxide. The flow rate for the analyses was 0.42 mL/min. and the injection volume 6 µl. A ThermoSeparations Constametric 3500 liquid chromatograph (ThermoSeparation Products, San Jose, Calif.) and HTS PAL autosampler were used for LC/MS analyses. Chromatographic separations were achieved employing a Luna $C_{18}$, 5 micron column, 2×30 mm (Phenomenex, Torrance, Calif.). The flow rate for the analyses was 1.0 mL/min and column effluent was split, so that the flow into the electrospray interface was 400 µl/min. A linear gradient from 0% to 100% B in A over 4 minutes was run, where mobile phase A was 98:2 water:acetonitrile with 10 mM ammonium acetate and mobile phase B was 10:90 water:acetonitrile with 10 mM ammonium acetate. The UV response was monitored at 220 nm. The samples were dissolved in 200 µl 50:50 $H_2O$:MeCN (0.05% TFA). The injection volume was 5 µl.

In all cases, the experimentally measured molecular weight was within 0.5 Daltons of the calculated mono-isotopic molecular weight.

Example CC

Synthesis of H-Ala-Phe(4-F)-Pro-Gly-Trp-Leu-Val-Lys-Asn-Gly-NH$_2$ (SEQ ID NO: 3)

The peptide of SEQ ID NO:3 was synthesized by solid phase synthesis using an Advanced ChemTech Model 90 Peptide Synthesizer. Each coupling cycle included the following steps:
 1. 20% piperidine in DMF 1×30 mL×5 min.
 2. 20% piperidine in DMF 1×30 mL×15 min.
 3. NMP washes: 8×30 mL×1 min.
 4. Coupling of the appropriate Fmoc-amino acid.
 5. DMF washes: 4×30 mL×1 min.

Coupling of Fmoc-Gly-OH to Sieber Amide Resin

The Sieber Amide resin (4.02 g, 0.66 mmole/g) was washed with DMF (1×40 mL×5 mins.) and the Fmoc group was removed using steps 1 to 3 above. To a solution of Fmoc-Gly-OH (1.58 g, 5.31 mmole) and HCTU (2.62 g, 6.33 mmole) in NMP (18 mL) was added DIEA (1.68 g, 13.0 mmole). The resulting solution was briefly vortexed and then added to the deprotected resin. DCM (6 mL) was added to the reactor and the mixture was mixed for a total of three hours. The resin was then washed successively with DMF and DCM (both 4×30 mL×1 minute), treated with 10% acetic anhydride in DCM (1×60 mL) and washed with DCM (4×30 mL×1 min.). The resin was dried in vacuo overnight. The yield of resin was 4.40 g. A sample of the resin was subjected to a Fmoc determination procedure (Green et al., Tetrahedron, 49(20):4141-4146 (1993)). The substitution was determined to be 0.60 mmol/gram. The total mmoles on the resin was 2.64 mmoles.

Coupling of Fmoc-Asn(Trt)-OH

The resin was washed with DMF (1×40 mL×5 mins.) and then treated as described above to remove the Fmoc group. To a solution of Fmoc-Asn(Trt)-OH (3.17 g, 5.31 mmole) and HCTU (2.63 g, 6.36 mmole) in NMP (18 mL) was added DIEA (1.68 g, 13.0 mmole). The resulting solution was briefly vortexed and added to the deprotected resin. DCM (6 mL) was added to the reactor and the whole was mixed for 4 hours and then washed successively with DMF and DCM (both 4×30 mL×1 minute). A Kaiser ninhydrin test of the peptide-resin was negative.

Coupling of Fmoc-Lys(Boc)-OH

The Fmoc group was removed as described above. To a solution of Fmoc-Lys(Boc)-OH (2.50 g, 5.34 mmole) and HCTU (2.66 g, 6.43 mmole) in NMP (18 mL) was added DIEA (1.68 g, 13.0 mmole). The resulting solution was briefly vortexed and added to the deprotected resin. DCM (6 mL) was added to the reactor and the mixture was mixed for a total of three hours. The peptide-resin was then washed successively with DMF and DCM (both 4×30 mL×1 minute). The peptide-resin was treated with 10% acetic anhydride in DCM for 20 minutes and then washed with DCM (6×30 mL×1 min.).

Coupling Fmoc-Val-OH

The peptide-resin was washed with DMF (1×30 mL×5 mins.) and the Fmoc group was removed as described above. To a solution of Fmoc-Val-OH (1.81 g, 5.33 mmole) and HCTU (2.64 g, 6.38 mmole) in NMP (18 mL) was added DIEA (1.63 g, 12.6 mmole). The resulting solution was briefly vortexed and added to the deprotected resin. DCM (6 mL) was added to the reactor and the mixture was mixed for 4 hours, and then washed successively with DMF and DCM (both 4×30 mL×1 minute).

Coupling of Fmoc-Leu-OH

The peptide-resin was washed with DMF (1×30 mL×5 mins.) and the Fmoc group was removed as described above. To a solution of Fmoc-Leu-OH (1.87 g, 5.29 mmole) and HCTU (2.66 g, 6.43 mmole) in NMP (18 mL) was added DIEA (1.71 g, 13.2 mmole). The resulting solution was briefly vortexed and added to the deprotected resin. DCM (6 mL) was added to the reactor and the mixture was mixed for 2.5 hours and then washed successively with DMF and DCM (both 4×30 mL×1 minute).

Coupling of Fmoc-Trp(Boc)-OH

The Fmoc group was removed as described above. To a solution of Fmoc-Trp(Boc)-OH (2.80 g, 5.32 mmole) and HCTU (2.66 g, 6.43) in NMP (18 mL) was added DIEA (1.67 g, 12.92 mmole). The resulting solution was briefly vortexed and added to the deprotected resin. DCM (6 mL) was added to the reactor and the mixture was mixed for 1 hour. A sample of resin was submitted twice to a Kaiser ninhydrin test and the result was positive in both cases. The peptide-resin was then washed successively with DMF and DCM (both 4×30 mL×1 minute). A sample (~4 mg) of the peptide-resin was cleaved/deprotected using TFA/TIS/$H_2O$ 96:2:2 (1 mL) for 1 hour. The isolated product indicated that the coupling was largely incomplete.

To a solution of Fmoc-Trp(Boc)-OH (7.00 g, 13.29 mmole) and 6-Cl-HOBt (2.21 g, 13.03 mmole) in NMP (30 mL) was added DIC (1.69 g, 13.39 mmole). The resulting solution was briefly vortexed and then added to the deprotected resin. DCM (10 mL) was added to the reactor and the whole was mixed for 16 hours, then washed successively with DMF and DCM (both 4×30 mL×1 minute). A sample of the peptide-resin gave a negative Kaiser ninhydrin test, suggesting coupling completion.

Coupling of Fmoc-Gly-OH

The Fmoc group was removed as described above. To a solution of Fmoc-Gly-OH (1.60 g, 5.38 mmole) and HCTU (2.66 g, 6.43 mmole) was added DIEA (1.65 g, 12.77 mmole). The resulting solution was briefly vortexed and then added to the deprotected resin. DCM (10 mL) was added to the reactor and the mixture was mixed for 4 hours then washed successively with DMF and DCM (both 4×30 mL×1 minute). A sample of the peptide-resin gave a positive Kaiser ninhydrin test.

To a solution of Fmoc-Gly-OH (2.36 g, 7.94 mmole) and 6-Cl-HOBt (1.36 g, 8.02 mmole) in NMP (18 mL) was added DIC (1.02 g, 8.08 mmole). The resulting solution was briefly vortexed and then added to the deprotected resin. DCM (6 mL) was added to the reactor and the mixture was mixed for 80 minutes. A sample of the peptide-resin gave a negative Kaiser ninhydrin test. The peptide-resin was washed with DMF (4×30 mL×1 minute).

Coupling of Fmoc-Pro-OH

The Fmoc group was removed as described above. To a solution of Fmoc-Pro-OH (2.71 g, 8.03 mmole) and 6-Cl-HOBt (1.37 g, 8.08 mmole) in NMP (18 mL) was added DIC (1.02 g, 8.08 mmole). The resulting solution was briefly vortexed and then added to the deprotected resin. DCM (6 mL) was added to the reactor, the mixture was mixed for 4 hours and was then washed successively with DMF and DCM (both 4×30 mL×1 minute). A sample of the peptide-resin gave a negative Kaiser ninhydrin test.

Coupling of Fmoc-Phe(4-F)—OH

The Fmoc group was removed as described above. To a solution of Fmoc-Phe(4-F)—OH (1.83 g, 4.51 mmole) and 6-Cl-HOBt (0.78 g, 4.60 mmole) in NMP (18 mL) was added DIC (0.57 g, 4.52 mmole). The resulting solution was briefly vortexed and then added to the deprotected resin. DCM (6 mL) was added to the reactor and the mixture was mixed for 20 hours. The peptide-resin was then washed successively with DMF and DCM (both 4×30 mL×1 minute). A sample of the peptide-resin (~4 mg) was treated with TFA/TIS/H$_2$O 96:2:2 (1 mL) for 1 hour. The isolated product indicated coupling completion.

Coupling of Boc-Ala-OH

The Fmoc group was removed as described above. To a solution of Boc-Ala-OH (1.50 g, 7.93 mmole) and 6-Cl-HOBt (1.34 g, 7.90 mmole) in NMP (18 mL) was added DIC (1.02 g, 8.08 mmole). The resulting solution was briefly vortexed and then added to the deprotected resin. DCM (6 mL) was added to the reactor and the mixture was mixed for 16 hours. The peptide-resin was then washed successively with DMF and DCM (both 4×30 mL×1 minute). A sample of the peptide-resin was submitted to the Kaiser ninhydrin test and gave a negative result, suggesting coupling completion.

Cleavage from the Resin and Deprotection

The peptide-resin was transferred from the ACT 90 reactor to 250 mL manual reactor using DMF. The peptide-resin was washed with DCM (6×40 mL×1 min.) and then treated with TFA/TIS/Water 96:2:2 (1×40 mL×20 mins. and 2×15 mL×20 mins.) and then with DCM (1×30 mL×20 mins.). The filtrates were successively collected, combined and then concentrated by reduced pressure. The resulting residue was triturated with diisopropyl ether (75 mL) and the precipitate was collected by filtration, washed with diisopropyl ether (2×10 mL) and dried in vacuo to yield the crude peptide (3.58 g). Analysis of the crude peptide showed the presence of the presence of Nim-COOH Trp. Therefore the peptide was dissolved in 2% acetic acid in water (50 mL) and the resulting solution was left to stand at room temperature for 1 hour. The peptide solution was filtered, frozen and lyophilized to yield the desired crude peptide (3.16 g).

Preparative HPLC

Preparative HPLC was carried out on a Waters Model 4000 preparative HPLC. The crude peptide was injected into a PHENOMENEX® Luna C18(2) 5 μm 250×30 mm column and eluted using a linear gradient from 10% B to 40% B over 60 min. at a flow rate of 15 mL/min with effluent UV detection at 217 nm. Buffer A was 0.1% TFA in water. Buffer B was 0.1% TFA in MeCN. The fractions containing the desired product from three preparative HPLC runs were pooled, concentrated by reduced pressure, frozen and lyophilized to give 1.68 g of purified peptide. Fractions containing the desired peptide but of insufficient purity were combined, concentrated, frozen and lyophilized. These were submitted to further purification as described and combined with the 1.68 g of purified peptide to yield 2.20 g of final peptide (99% pure by analytical HPLC).

Example DD

The procedures described above were used to synthesize the following peptides:

| SEQ ID NO. | 1 | 2 | 3 | 4 | 5 | 6 | 7 | 8 | 9 | 10 |
|---|---|---|---|---|---|---|---|---|---|---|
| 1 | A | Y | P | G | K | F | | | | |
| 2 | A | Y | P | G | W | L | V | K | N | G |
| 3 | A | Phe(4-F) | P | G | W | L | V | K | N | G |
| 4 | A | Phe(4-F) | P | G | W | L | V | K | N | |
| 5 | A | Phe(4-F) | P | G | W | L | V | K | | |
| 6 | A | Phe(4-F) | P | G | W | L | V | | | |
| 7 | A | Phe(4-F) | P | G | W | L | | | | |
| 8 | A | Phe(4-F) | P | G | W | | | | | |
| 9 | A | Phe(4-F) | P | G | | | | | | |
| 10 | A | Y | P | G | | | | | | |
| 11 | A | Y | P | G | Q | V | C | A | N | D |
| 12 | A | Phe(4-F) | P | G | Trp(5-OH) | L | V | | | |
| 13 | A | Phe(4-F) | P | G | (D, L)-Trp(5-Br) | L | V | | | |
| 14 | A | Phe(4-F) | P | G | D-Trp | L | V | | | |
| 15 | A | Phe(4-F) | P | G | Bzt | L | V | | | |
| 16 | A | Phe(4-F) | P | G | Tpi | L | V | | | |
| 17 | A | Phe(4-F) | P | G | H | L | V | | | |
| 18 | A | Phe(4-F) | P | G | Tza | L | V | | | |
| 19 | A | Phe(4-F) | P | G | 3-Thi | L | V | | | |
| 20 | A | Phe(4-F) | P | G | 3-Fur | L | V | | | |
| 21 | A | Phe(4-F) | P | G | His(Bzl) | L | V | | | |
| 22 | A | Phe(4-F) | P | G | F | L | V | | | |
| 23 | A | Phe(4-F) | P | G | Y | L | V | | | |
| 24 | A | Phe(4-F) | P | G | Phe(penta-F) | L | V | | | |
| 25 | A | Phe(4-F) | P | G | 2-Pya | L | V | | | |
| 26 | A | Phe(4-F) | P | G | 3-Pya | L | V | | | |
| 27 | A | Phe(4-F) | P | G | 4-Pya | L | V | | | |
| 28 | A | Phe(4-F) | P | G | Dpa | L | V | | | |
| 29 | A | Phe(4-F) | P | G | 3-Pya(4-Tolyl) | L | V | | | |
| 30 | A | Phe(4-F) | P | G | Bip(2-Methyl) | L | V | | | |
| 31 | A | Phe(4-F) | P | G | 1-Naphthyl-Ala | L | V | | | |
| 32 | A | Phe(4-F) | P | G | 2-Naphthyl-Ala | L | V | | | |
| 33 | A | Phe(4-F) | P | G | Tyr(Bzl) | L | V | | | |
| 34 | A | Phe(4-F) | P | G | Styryl-Ala | L | V | | | |

What is claimed is:

1. A protease activated receptor 4 (PAR4) agonist peptide comprising an amino acid sequence of Formula I, $$\text{Ala-Xaa}_1\text{-Pro-Gly-Xaa}_2\text{-Leu-Val} \quad \text{(Formula I)}$$

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus of the peptide is amidated.

2. The PAR4 agonist peptide of claim 1 wherein $X_{aa1}$ is Phe(4-F).

3. The PAR4 agonist peptide of claim 2 wherein $X_{aa2}$ is Trp.

4. A PAR4 agonist peptide comprising an amino acid sequence of SEQ ID NO: 3, wherein the amino terminus of the peptide is free and the C-terminus of the peptide is amidated.

5. The PAR4 agonist peptide of claim 1, further comprising Lys after Val.

6. The PAR4 agonist peptide of claim 1, further comprising Lys-Asn after Val.

7. The PAR4 agonist peptide of claim 1, further comprising Lys-Asn-Gly after Val.

8. A PAR4 agonist peptide comprising an amino acid sequence of Formula II, $$\text{Ala-Xaa}_1\text{-Pro-Gly-Xaa}_2\text{-Leu-Val-Lys} \quad \text{(Formula II)}$$

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus of the peptide is amidated.

9. The PAR4 agonist peptide of claim 8 wherein $X_{aa1}$ is Phe(4-F).

10. The PAR4 agonist peptide of claim 8 wherein $X_{aa2}$ is Trp.

11. A PAR4 agonist peptide comprising an amino acid sequence of Formula III, $$\text{Ala-Xaa}_1\text{-Pro-Gly-Xaa}_2\text{-Leu-Val-Lys-Asn} \quad \text{(Formula III)}$$

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus of the peptide is amidated.

12. The PAR4 agonist peptide of claim 11 wherein $X_{aa1}$ is Phe(4-F).

13. The PAR4 agonist peptide of claim 11 wherein $X_{aa2}$ is Trp.

14. A PAR4 agonist peptide comprising an amino acid sequence of Formula IV, $$\text{Ala-Xaa}_1\text{-Pro-Gly-Xaa}_2\text{-Leu-Val-Lys-Asn-Gly} \quad \text{(Formula IV)}$$

wherein,
the amino terminus of the peptide is free;
$X_{aa1}$ is selected from Tyr and Phe(4-F);
$X_{aa2}$ is selected from Trp(5-OH), (D,L)-Trp(5-Br), D-Trp, Trp, Bzt, Tpi, His, Tza, 3-Thi, 3-Fur, His(Bzl), Phe, Tyr, Phe(penta-F), 2-Pya, 3-Pya, 4-Pya, Dpa, 3-Pya(4-Tolyl), Bip(2-Methyl), 1-Naphthyl-Ala, 2-Naphthyl-Ala, Tyr(Bzl) and Styryl-Ala; and
the C-terminus of the peptide is amidated.

15. The PAR4 agonist peptide of claim 14 wherein $X_{aa1}$ is Phe(4-F).

16. The PAR4 agonist peptide of claim 14 wherein $X_{aa2}$ is Trp.

* * * * *